(12) United States Patent
Inoue et al.

(10) Patent No.: US 9,837,621 B2
(45) Date of Patent: Dec. 5, 2017

(54) COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Hiroki Suzuki, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 300 days.

(21) Appl. No.: 14/695,686

(22) Filed: Apr. 24, 2015

(65) Prior Publication Data

US 2015/0311454 A1    Oct. 29, 2015

(30) Foreign Application Priority Data

Apr. 25, 2014    (JP) .................. 2014-091164

(51) Int. Cl.
*H01L 51/00* (2006.01)
*C07D 409/10* (2006.01)
*H01L 51/50* (2006.01)

(52) U.S. Cl.
CPC ........ *H01L 51/0074* (2013.01); *C07D 409/10* (2013.01); *H01L 51/0059* (2013.01); *H01L 51/0072* (2013.01); *H01L 51/0085* (2013.01); *H01L 51/504* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| 6,723,445 | B2 | 4/2004 | Li et al. |
| 2011/0210316 | A1* | 9/2011 | Kadoma .............. C07D 403/10 257/40 |
| 2012/0193613 | A1 | 8/2012 | Kadoma et al. |
| 2012/0197020 | A1 | 8/2012 | Osaka et al. |

(Continued)

FOREIGN PATENT DOCUMENTS

| JP | 2007-189001 A | 7/2007 |
| WO | WO 03/058667 A1 | 7/2003 |

OTHER PUBLICATIONS

SciFinder sub-structure search (Mar. 24, 2017).*
STN structure search (Apr. 12, 2017).*

*Primary Examiner* — Vu A Nguyen
(74) *Attorney, Agent, or Firm* — Husch Blackwell LLP

(57) ABSTRACT

To provide a novel compound which can be used as a host material in which a light-emitting substance is dispersed. To provide a light-emitting element having a long lifetime. A compound represented by General Formula (G0). In the formula, A represents any one of a substituted or unsubstituted dibenzothiophenylene group and a substituted or unsubstituted dibenzofuranylene group, X represents a substituted or unsubstituted fluorenyl group, E represents a substituted or unsubstituted dibenzo[f,h]quinoxalinyl group, and Ar represents a substituted or unsubstituted arylene group having 6 to 30 carbon atoms.

E-Ar-A-X    (G0)

20 Claims, 32 Drawing Sheets

(56) References Cited

U.S. PATENT DOCUMENTS

2013/0082591 A1    4/2013   Seo et al.
2015/0060824 A1    3/2015   Ishiguro et al.
2015/0073147 A1    3/2015   Inoue et al.

* cited by examiner

COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a compound, a light-emitting element utilizing electroluminescence (EL) (the light-emitting element is also referred to as an EL element), a light-emitting device, an electronic device, and a lighting device.

Note that one embodiment of the present invention is not limited to the above technical field. One embodiment of the invention disclosed in this specification and the like relates to an object, a method, and a manufacturing method. Moreover, one embodiment of the present invention relates to a process, a machine, manufacture, or a composition of matter. Specifically, examples of the technical field of one embodiment of the present invention disclosed in this specification include a semiconductor device, a display device, a light-emitting device, a power storage device, a memory device, an electronic device, a lighting device, a method for driving any of them, and a method for manufacturing any of them.

2. Description of the Related Art

In recent years, a light-emitting element using an organic compound as a light-emitting substance (the light-emitting element is also referred to as an organic EL element) has been actively researched and developed. In a basic structure of the light-emitting element, a layer containing a light-emitting substance is provided between a pair of electrodes. Voltage application to this element causes the light-emitting substance to emit light.

The light-emitting element is a self-luminous element and thus has advantages over a liquid crystal display, such as high visibility of the pixels and no need of backlight, and is considered to be suitable as a flat panel display element. Another major advantage of the light-emitting element is that it can be fabricated to be thin and lightweight. Besides, the light-emitting element has an advantage of quite high response speed.

Since the light-emitting element can be formed in a film form, planar light emission can be provided; thus, a large-area element can be easily formed. This feature is difficult to obtain with point light sources typified by incandescent lamps and LEDs or linear light sources typified by fluorescent lamps. Thus, the light-emitting element also has great potential as a planar light source applicable to a lighting device and the like.

In the case of a light-emitting element in which a layer containing an organic compound used as a light-emitting substance is provided between a pair of electrodes, by applying a voltage to the element, electrons from a cathode and holes from an anode are injected into the layer containing the organic compound and thus a current flows. The injected electrons and holes then lead the organic compound to its excited state, so that light emission is provided from the excited organic compound.

The excited state formed by an organic compound can be a singlet excited state or a triplet excited state. Light emission from the singlet excited state (S*) is called fluorescence, and light emission from the triplet excited state (T*) is called phosphorescence. The statistical generation ratio thereof in the light-emitting element is considered to be $S^*:T^*=1:3$.

At room temperature, a compound capable of converting a singlet excited state into light emission (hereinafter, referred to as a fluorescent compound) exhibits only light emission from the singlet excited state (fluorescence), and light emission from the triplet excited state (phosphorescence) cannot be observed. Accordingly, the internal quantum efficiency (the ratio of the number of generated photons to the number of injected carriers) of a light-emitting element including a fluorescent compound is assumed to have a theoretical limit of 25%, on the basis of $S^*:T^*=1:3$.

In contrast, a compound capable of converting a triplet excited state into light emission (hereinafter, referred to as a phosphorescent compound) exhibits light emission from the triplet excited state (phosphorescence). Furthermore, since intersystem crossing (i.e., transition from a singlet excited state to a triplet excited state) easily occurs in a phosphorescent compound, the internal quantum efficiency can be theoretically increased to 100%. That is, higher emission efficiency can be achieved than using a fluorescent compound. For this reason, light-emitting elements using a phosphorescent compound have been under active development recently so that high-efficiency light-emitting elements can be achieved.

When a light-emitting layer of a light-emitting element is limited using the phosphorescent compound described above, in order to inhibit concentration quenching or quenching due to triplet-triplet annihilation of the phosphorescent compound, the light-emitting layer is usually formed such that the phosphorescent compound is dispersed in a matrix of another compound. Here, the compound serving as the matrix is called host material, and the compound dispersed in the matrix, such as a phosphorescent compound, is called guest material.

When a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Thus, the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] PCT International Publication No. 03/058667
[Patent Document 2] Japanese Published Patent Application No. 2007-189001

SUMMARY OF THE INVENTION

In improving element characteristics of a light-emitting element, there are many problems which depend on a substance. Therefore, improvement in an element structure, development of a substance, and the like have been carried out in order to solve the problems. Development of light-emitting elements leaves room for improvement in terms of emission efficiency, reliability, cost, and the like.

For practical use of a display or lighting which uses a light-emitting element, a long lifetime of the light-emitting element has been required.

In view of the above, an object of one embodiment of the present invention is to provide a novel compound. An object of one embodiment of the present invention is to provide a novel compound which can be used in a light-emitting element as a host material in which a light-emitting substance is dispersed. An object of one embodiment of the present invention is to provide a compound having high triplet excitation energy. An object of one embodiment of the present invention is to provide a compound with high solubility. An object of one embodiment of the present invention is to provide a compound with high heat resistance.

An object of one embodiment of the present invention is to provide a light-emitting element with high emission efficiency. An object of one embodiment of the present invention is to provide a light-emitting element with a low drive voltage. An object of one embodiment of the present invention is to provide a light-emitting element having a long lifetime. An object of one embodiment of the present invention is to provide a light-emitting element with high heat resistance. An object of one embodiment of the present invention is to provide a novel light-emitting element.

An object of one embodiment of the present invention is to provide a highly reliable light-emitting device, a highly reliable electronic device, or a highly reliable lighting device using the light-emitting element. An object of one embodiment of the present invention is to provide a light-emitting device, an electronic device, or a lighting device with low power consumption using the light-emitting element.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a compound represented by General Formula (G0).

E-Ar-A-X  (G0)

In General Formula (G0), A represents any one of a substituted or unsubstituted dibenzothiophenylene group and a substituted or unsubstituted dibenzofuranylene group, X represents a substituted or unsubstituted fluorenyl group, E represents a substituted or unsubstituted dibenzo[f,h]quinoxalinyl group, and Ar represents a substituted or unsubstituted arylene group having 6 to 30 carbon atoms.

One embodiment of the present invention is a compound represented by General Formula (G1).

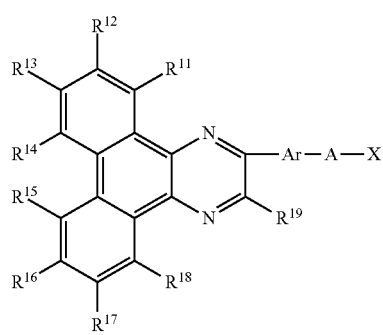

(G1)

In General Formula (G1), A represents any one of a substituted or unsubstituted dibenzothiophenylene group and a substituted or unsubstituted dibenzofuranylene group, X represents a substituted or unsubstituted fluorenyl group, each of $R^{11}$ to $R^{19}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G2).

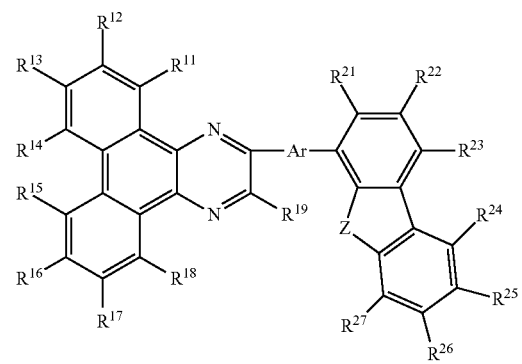

(G2)

In General Formula (G2), Z represents any one of oxygen and sulfur, each of $R^{11}$ to $R^{19}$ independently represents any one of hydrogen, an alkyl group having 1 to 4 carbon atoms, and a substituted or unsubstituted aryl group having 6 to 13 carbon atoms, at least one of $R^{21}$ to $R^{27}$ represents a substituted or unsubstituted fluorenyl group, each of the others of $R^{21}$ to $R^{27}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G3).

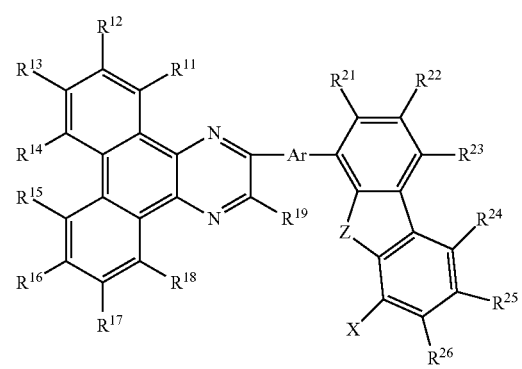

(G3)

In General Formula (G3), Z represents any one of oxygen and sulfur, X represents a substituted or unsubstituted fluorenyl group, each of $R^{11}$ to $R^{19}$ and $R^{21}$ to $R^{26}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G4).

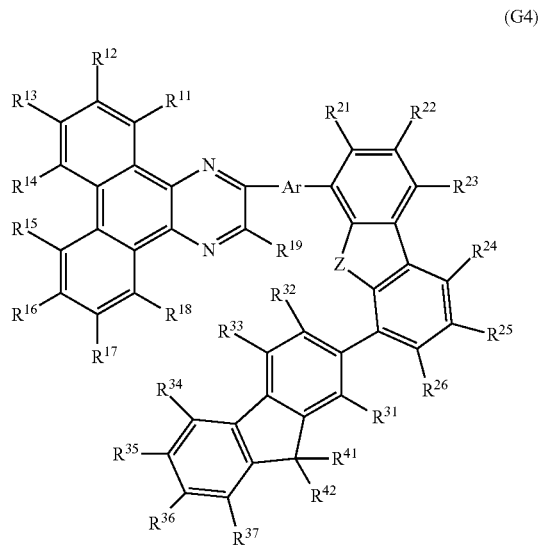

(G4)

In General Formula (G4), Z represents any one of oxygen and sulfur, each of $R^{11}$ to $R^{19}$, $R^{21}$ to $R^{26}$, and $R^{31}$ to $R^{37}$ independently represents any one of hydrogen, an alkyl group having 1 to 6 carbon atoms, and a substituted or unsubstituted aryl group having 6 to 13 carbon atoms, each of $R^{41}$ and $R^{42}$ independently represents any one of hydrogen and an alkyl group having 1 to 6 carbon atoms, and Ar represents a substituted or unsubstituted arylene group having 6 to 30 carbon atoms.

In General Formula (G4), $R^{41}$ and $R^{42}$ each preferably represent a methyl group.

In any of the above structures, X preferably represents a substituted or unsubstituted 9,9-dialkylfluorenyl group.

In any of the above structures, Ar preferably represents any one of a substituted or unsubstituted phenylene group and a substituted or unsubstituted biphenyldiyl group.

One embodiment of the present invention is a light-emitting element including a layer containing a light-emitting organic compound between a pair of electrodes. The layer containing the light-emitting organic compound contains the compound with any one of the above structures.

One embodiment of the present invention is a light-emitting element including a layer containing a light-emitting organic compound between a pair of electrodes. The layer containing the light-emitting organic compound contains a light-emitting substance and the compound with any one of the above structures.

One embodiment of the present invention is a light-emitting device including the above-described light-emitting element in a light-emitting portion. For example, a light-emitting device of one embodiment of the present invention may include the above light-emitting element and a transistor or a substrate. One embodiment of the present invention is an electronic device including the light-emitting device in a display portion. For example, an electronic device of one embodiment of the present invention may include the above light-emitting device and a microphone, a speaker, or an external connection terminal. One embodiment of the present invention is a lighting device including the light-emitting device in a light-emitting portion. For example, a lighting device of one embodiment of the present invention may include the above light-emitting device and a support, a housing, or a cover.

Note that the light-emitting device in this specification includes, in its category, a display device using a light-emitting element. Furthermore, the light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may be included in lighting equipment or the like.

One embodiment of the present invention makes it possible to provide a novel compound. One embodiment of the present invention makes it possible to provide a novel compound which can be used in a light-emitting element as a host material in which a light-emitting substance is dispersed. One embodiment of the present invention makes it possible to provide a compound having high triplet excitation energy. One embodiment of the present invention makes it possible to provide a compound with high solubility. One embodiment of the present invention makes it possible to provide a compound with high heat resistance.

One embodiment of the present invention makes it possible to provide a light-emitting element with high emission efficiency. One embodiment of the present invention makes it possible to provide a light-emitting element with a low drive voltage. One embodiment of the present invention makes it possible to provide a light-emitting element having a long lifetime. One embodiment of the present invention makes it possible to provide a light-emitting element with high heat resistance. One embodiment of the present invention makes it possible to provide a novel light-emitting element.

One embodiment of the present invention makes it possible to provide a highly reliable light-emitting device, a highly reliable electronic device, or a highly reliable lighting device using the light-emitting element. One embodiment of the present invention makes it possible to provide a light-emitting device, an electronic device, or a lighting device with low power consumption using the light-emitting element.

Note that the description of these effects does not disturb the existence of other effects. One embodiment of the present invention does not necessarily achieve all the above effects. Other effects will be apparent from and can be derived from the description of the specification, the drawings, the claims, and the like.

DETAILED DESCRIPTION OF THE INVENTION

Figure 1A:
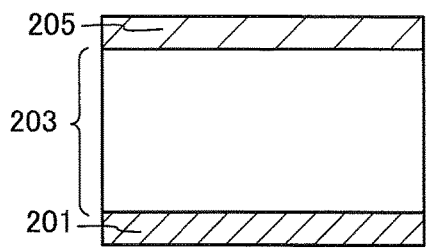
FIGS. 1A to 1D each illustrate an example of a light-emitting element of one embodiment of the present invention.

Embodiments of the present invention will be described in detail with reference to the drawings. Note that the present invention is not limited to the following description, and it is easily understood by those skilled in the art that various changes for embodiments and details can be made without departing from the spirit and scope of the invention. Therefore, the present invention should not be construed as being limited to the description in the following embodiments.

Note that in the structures of the invention described below, the same portions or portions having similar functions are denoted by the same reference numerals in different drawings, and description of such portions is not repeated. Furthermore, the same hatching pattern is applied to portions having similar functions, and the portions are not especially denoted by reference numerals in some cases.

In addition, the position, size, range, or the like of each structure illustrated in drawings and the like is not accurately represented in some cases for easy understanding. Therefore, the disclosed invention is not necessarily limited to the position, the size, the range, or the like disclosed in the drawings and the like.

(Embodiment 1)

In this embodiment, a compound of one embodiment of the present invention is described.

One embodiment of the present invention is a compound in which a dibenzo[f,h]quinoxaline skeleton and a dibenzothiophene skeleton or a dibenzofuran skeleton are bonded through an arylene skeleton. The dibenzothiophene skeleton or dibenzofuran skeleton has a fluorenyl group as a substituent.

A dibenzo[f,h]quinoxaline skeleton has a planar structure. An organic compound having a planar structure is easily crystallized. A light-emitting element using an organic compound that is easily crystallized has a short lifetime. However, the compound of one embodiment of the present invention has a sterically bulky structure since a dibenzothiophene skeleton or a dibenzofuran skeleton is bonded to a dibenzo[f,h]quinoxaline skeleton through an arylene skeleton. The compound of one embodiment of the present invention is not easily crystallized, which can inhibit a reduction in lifetime of a light-emitting element. Because the dibenzothiophene skeleton or dibenzofuran skeleton has a fluorenyl group as a substituent, the compound of one embodiment of the present invention has extremely high heat resistance, and when the compound is used in a light-emitting element, the light-emitting element can have high heat resistance and a long lifetime.

In addition, the compound of one embodiment of the present invention has high solubility. A compound in which a dibenzo[f,h]quinoxaline skeleton and a dibenzothiophene skeleton or a dibenzofuran skeleton are combined in itself has a low solubility in a solvent. However, the present inventors have found that the solubility is dramatically increased when a fluorenyl group (e.g., a 9,9-dialkylfluorenyl group) is bonded to a dibenzothiophene skeleton or a dibenzofuran skeleton as in the compound of one embodiment of the present invention. A compound with high solubility can be easily purified and impurities thereof can be easily eliminated. Accordingly, by including the compound of one embodiment of the present invention, a light-emitting element can have suppressed initial deterioration and high reliability.

When a compound that cannot easily accept electrons or holes is used as a host material in a light-emitting layer, the regions of electron-hole recombination concentrate on an interface between the light-emitting layer and a different layer, leading to a reduction in lifetime of a light-emitting element. Here, the compound of one embodiment of the present invention can easily accept electrons and holes since the compound has a dibenzo[f,h]quinoxaline skeleton as an electron-transport skeleton and a dibenzothiophene or dibenzofuran skeleton as a hole-transport skeleton. Accordingly, by the use of the compound of one embodiment of the present invention as the host material of the light-emitting layer, electrons and holes presumably recombine in a wide region of the light-emitting layer and it is possible to inhibit a reduction in lifetime of the light-emitting element.

As compared to extension of a conjugated system in a compound in which a dibenzo[f,h]quinoxaline skeleton and a hole-transport skeleton are directly bonded, extension of a conjugated system in the compound of one embodiment of the present invention in which the two skeletons are bonded through an arylene group is small; accordingly, reductions in band gap and triplet excitation energy can be prevented. The compound of one embodiment of the present invention is also advantageous in that its heat resistance and film quality are high.

The compound of one embodiment of the present invention has a wide band gap. Accordingly, the compound can be favorably used as a host material, in which a light-emitting substance is dispersed, of a light-emitting layer in a light-emitting element. It is particularly preferable that the compound of one embodiment of the present invention be used as a host material in which a phosphorescent compound emitting light in a wavelength range from red to green is dispersed.

Furthermore, since the compound of one embodiment of the present invention has a high electron-transport property, the compound can be suitably used as a material for an electron-transport layer in a light-emitting element.

Thus, the compound of one embodiment of the present invention can be suitably used as a material for an organic device such as a light-emitting element or an organic transistor.

One embodiment of the present invention is a compound represented by General Formula (G0). The compound, in which a dibenzothiophene skeleton or a dibenzofuran skeleton has a fluorenyl group as a substituent, has higher heat resistance and solubility than a compound without the substituent.

E-Ar-A-X     (G0)

In General Formula (G0), A represents any one of a substituted or unsubstituted dibenzothiophenylene group and a substituted or unsubstituted dibenzofuranylene group, X represents a substituted or unsubstituted fluorenyl group, E represents a substituted or unsubstituted dibenzo[f,h]quinoxalinyl group, and Ar represents a substituted or unsubstituted arylene group having 6 to 30 carbon atoms.

In the compound represented by General Formula (G0), Ar is preferably bonded to the 2-position, the 6-position, or the 7-position of the dibenzo[f,h]quinoxaline skeleton for easier synthesis, higher purity, a higher $T_1$ level, and the like. Preferably, Ar is bonded to the 2-position because the compound can be more easily synthesized and have high purity more easily and thus can be provided at lower cost than in the case where Ar is bonded to the 6-position or the 7-position. Preferably, Ar is bonded to the 6-position because a $T_1$ level can be higher than in the case where Ar is bonded to the 2-position or the 7-position. Preferably, Ar is bonded to the 7-position because a $T_1$ level can be higher than in the case where Ar is bonded to the 2-position.

One embodiment of the present invention is a compound represented by General Formula (G1).

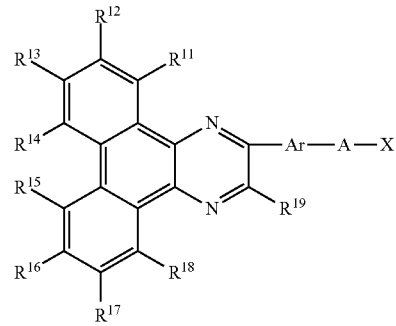

(G1)

In General Formula (G1), A represents any one of a substituted or unsubstituted dibenzothiophenylene group and a substituted or unsubstituted dibenzofuranylene group, X represents a substituted or unsubstituted fluorenyl group, each of $R^{11}$ to $R^{19}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G2). Preferably, Ar is bonded to the 4-position of the dibenzothiophenylene group or the dibenzofuranylene group for easier synthesis.

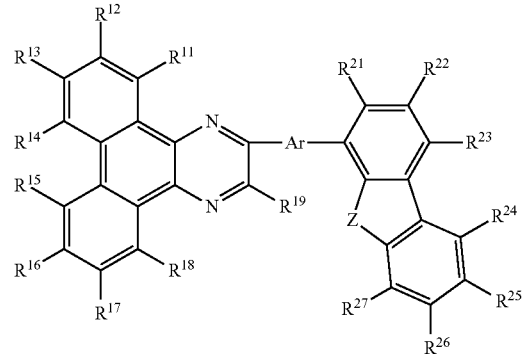

(G2)

In General Formula (G2), Z represents any one of oxygen and sulfur, each of $R^{11}$ to $R^{19}$ independently represents any one of hydrogen, an alkyl group having 1 to 4 carbon atoms, and a substituted or unsubstituted aryl group having 6 to 13 carbon atoms, at least one of $R^{21}$ to $R^{27}$ represents a substituted or unsubstituted fluorenyl group, each of the others of $R^{21}$ to $R^{27}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G3). A 4,6-dibenzothiophenediyl group and a 4,6-dibenzofurandiyl group each having a fluorenyl group as a substituent are preferable for easier synthesis.

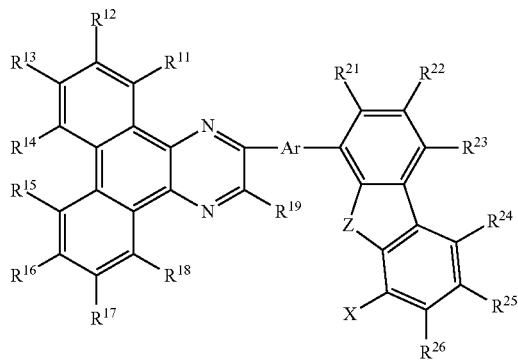

(G3)

In General Formula (G3), Z represents any one of oxygen and sulfur, X represents a substituted or unsubstituted fluorenyl group, each of $R^{11}$ to $R^{19}$ and $R^{21}$ to $R^{26}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

One embodiment of the present invention is a compound represented by General Formula (G4). A dibenzothiophenylene group or a dibenzofuranylene group is preferably bonded to the 2-position of a fluorenyl group for easier synthesis.

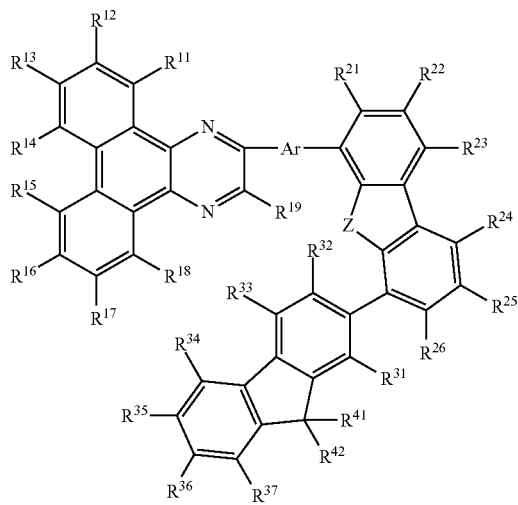

(G4)

In General Formula (G4), Z represents any one of oxygen and sulfur, each of $R^{11}$ to $R^{19}$, $R^{21}$ to $R^{26}$, and $R^{31}$ to $R^{37}$ independently represents any one of hydrogen, an alkyl group having 1 to 6 carbon atoms, and a substituted or unsubstituted aryl group having 6 to 13 carbon atoms, each of $R^{41}$ and $R^{42}$ independently represents any one of hydrogen and an alkyl group having 1 to 6 carbon atoms, and Ar represents a substituted or unsubstituted arylene group having 6 to 30 carbon atoms.

For a higher triplet excitation energy level ($T_1$ level), Ar in General Formulae above preferably represents an arylene group having 6 to 13 carbon atoms. In that case, the arylene group may have one or more substituents and the substituents may be bonded to each other to form a ring.

For a higher triplet excitation energy level ($T_1$ level), it is preferable that Ar in General Formulae above not be an anthrylene group or a pyrenylene group.

Specific examples of the structure of Ar in General Formulae above include substituents represented by Structural Formulae (1-1) to (1-24). For a higher triplet excitation energy level ($T_1$ level), higher heat resistance, easier synthesis, and the like, it is particularly preferable that Ar represent any one of a substituted or unsubstituted phenylene group and a substituted or unsubstituted biphenyldiyl group. Note that Ar may further have, as a substituent, any one of an alkyl group having 1 to 4 carbon atoms and an aryl group having 6 to 13 carbon atoms. As examples of the aryl group having 6 to 13 carbon atoms, a phenyl group, a naphthyl group, and a fluorenyl group can be given.

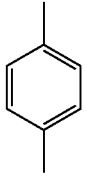

(1-1)

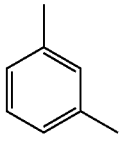

(1-2)

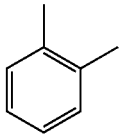

(1-3)

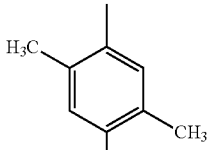

(1-4)

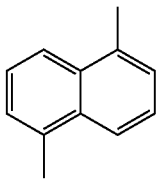

(1-5)

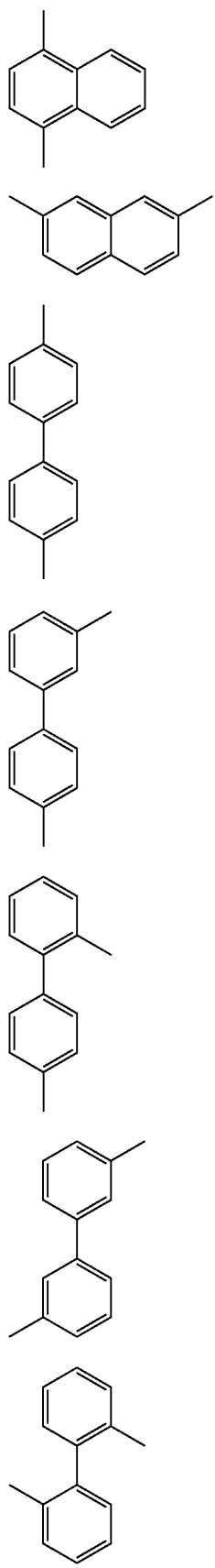
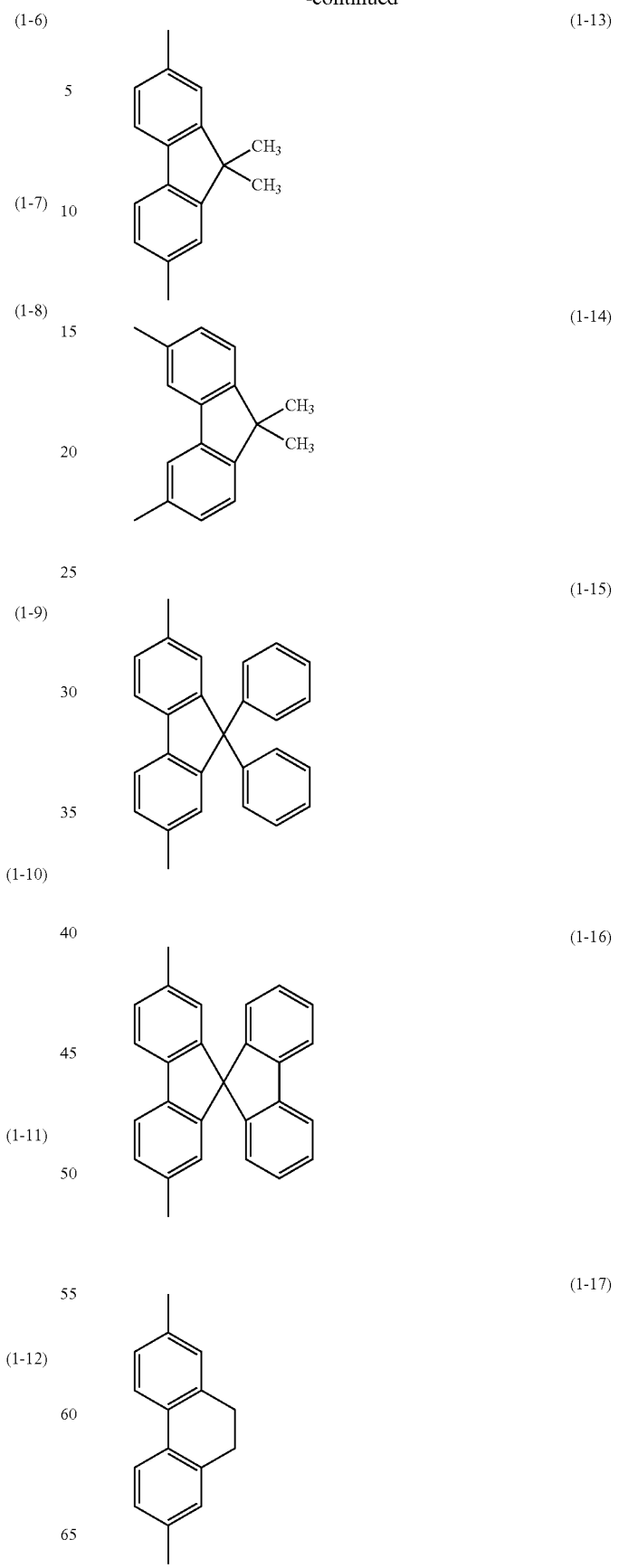

-continued

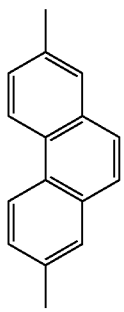
(1-18)

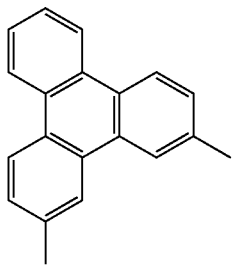
(1-19)

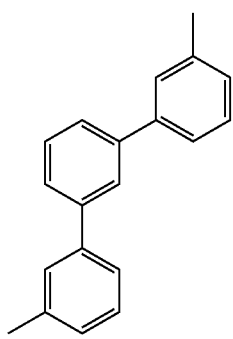
(1-20)

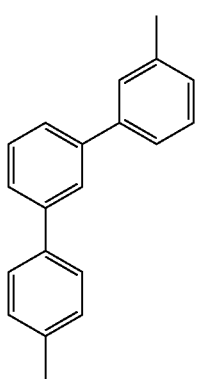
(1-21)

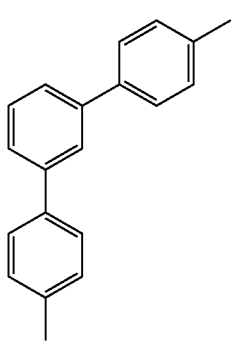
(1-21)

-continued

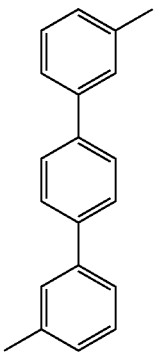
(1-22)

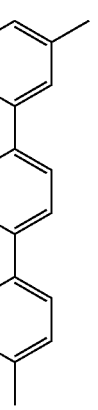
(1-23)

(1-24)

Specific examples of $R^{11}$ to $R^{19}$, $R^{21}$ to $R^{27}$, and $R^{31}$ to $R^{37}$ in General Formulae above include substituents represented by Structural Formulae (2-1) to (2-22). When $R^{11}$ to $R^{19}$, $R^{21}$ to $R^{27}$, and $R^{31}$ to $R^{37}$ represent aryl groups, $R^{11}$ to $R^{19}$, $R^{21}$ to $R^{27}$, and $R^{31}$ to $R^{37}$ may further have, as a substituent, any one of an alkyl group having 1 to 6 carbon atoms and an aryl group having 6 to 13 carbon atoms. As examples of the aryl group having 6 to 13 carbon atoms, a phenyl group, a naphthyl group, and a fluorenyl group can be given. Specific examples of the aryl group having a substituent are illustrated by Structural Formulae (2-13) to (2-22). Note that $R^{11}$ to $R^{19}$, $R^{21}$ to $R^{27}$, and $R^{31}$ to $R^{37}$ each having a substituent are not limited to these examples.

(2-1)

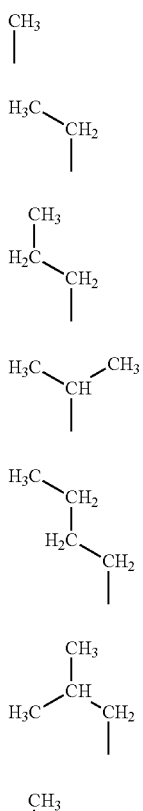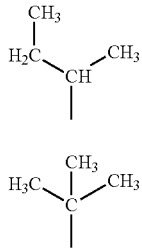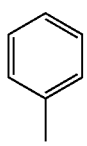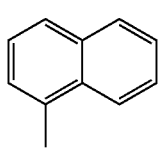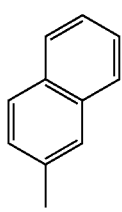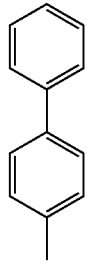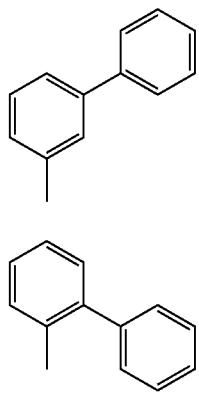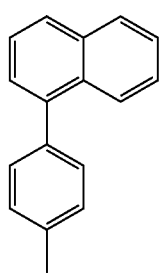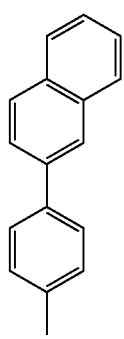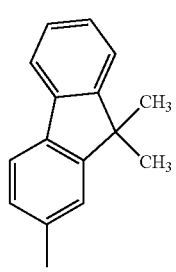

(2-19)

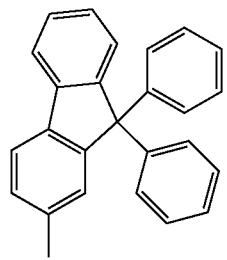

(2-20)

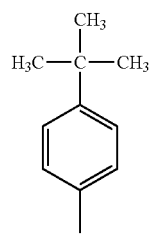

(2-21)

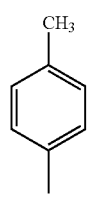

(2-22)

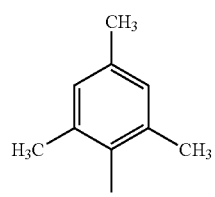

Specific examples of $R^{41}$ and $R^{42}$ in General Formula (G4) above include the substituents represented by Structural Formulae (2-1) to (2-9) above. It is particularly preferable that $R^{41}$ and $R^{42}$ each represent a methyl group in teats of easiness of synthesis and cost.

Specific examples of the compound of one embodiment of the present invention include compounds represented by Structural Formulae (100) to (148). However, the present invention is not limited to these structural formulae.

(101)

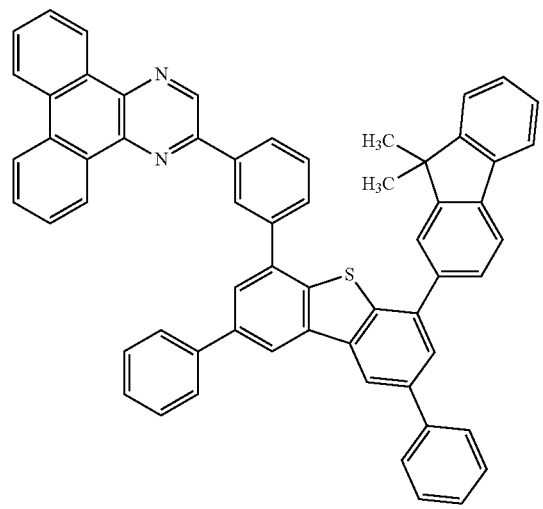

(102)

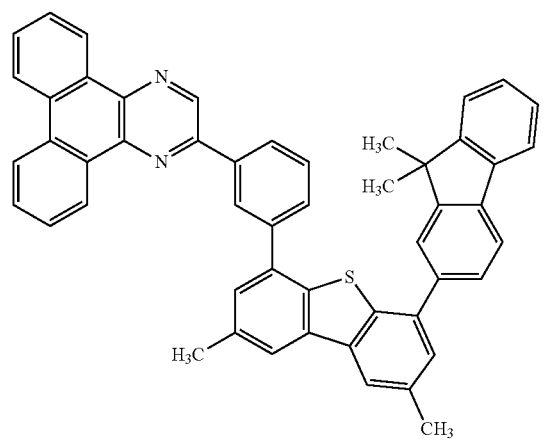

(100)

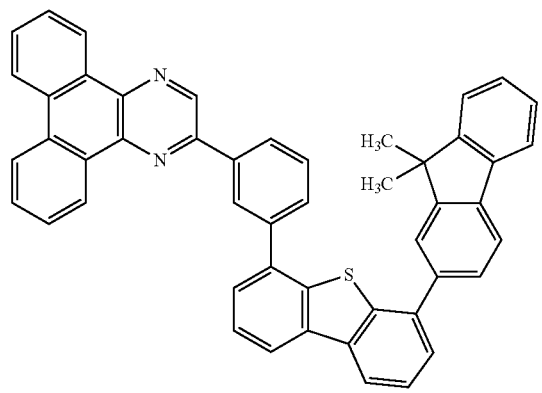

(103)

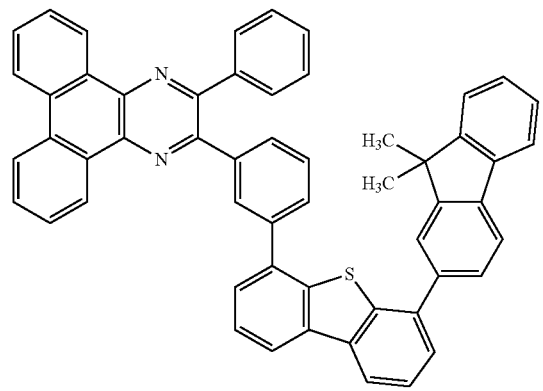

(104)
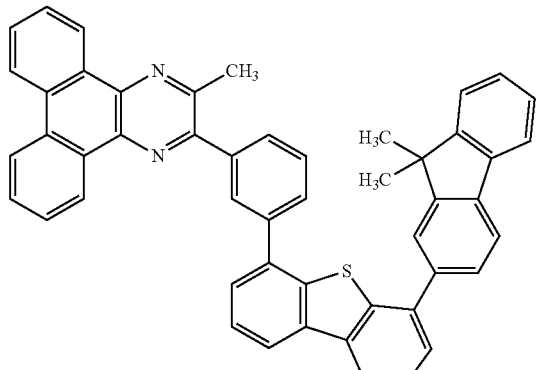
(105)
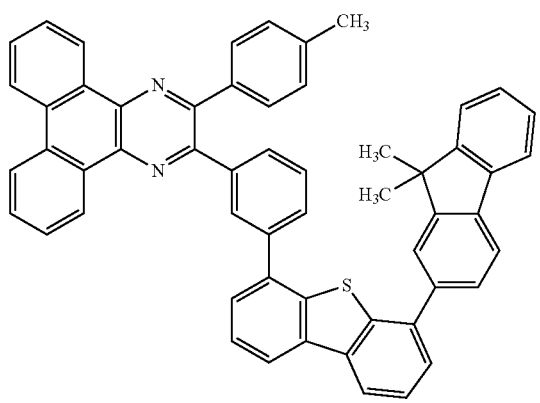
(106)
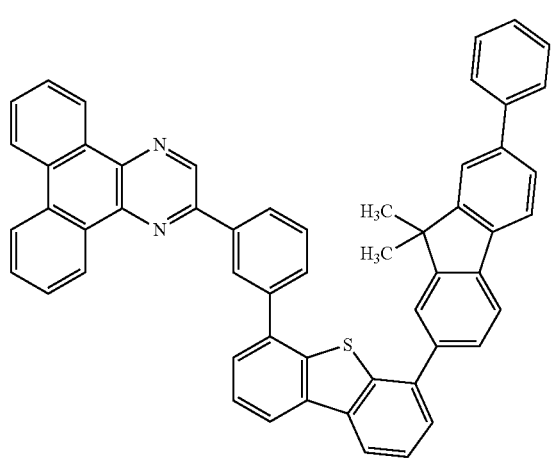
(107)
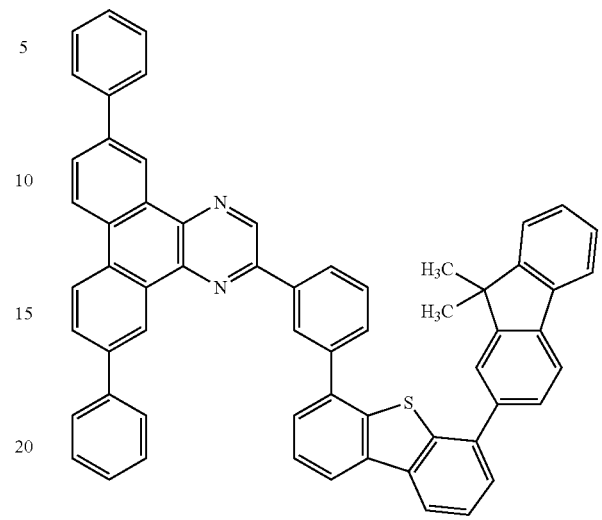
(108)
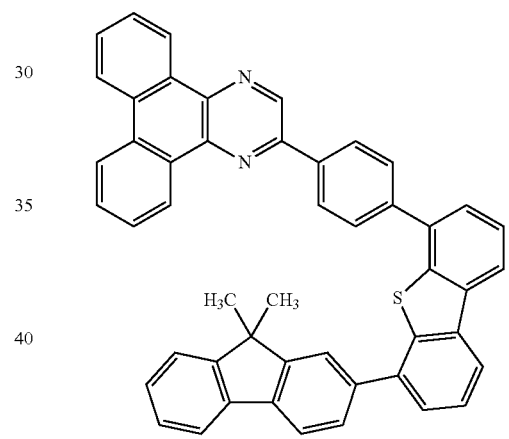
(109)
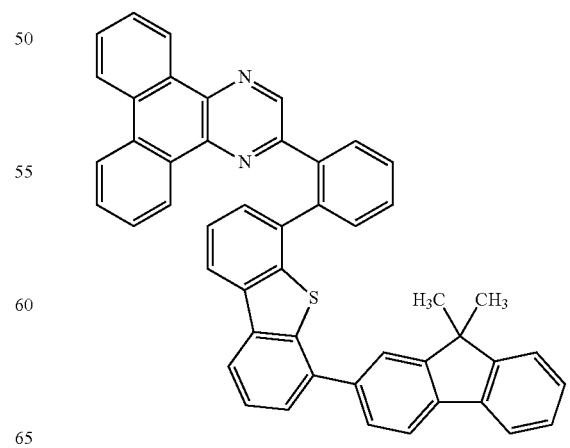

(110) 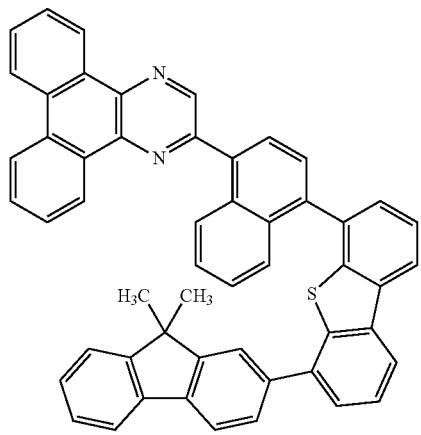
(111) 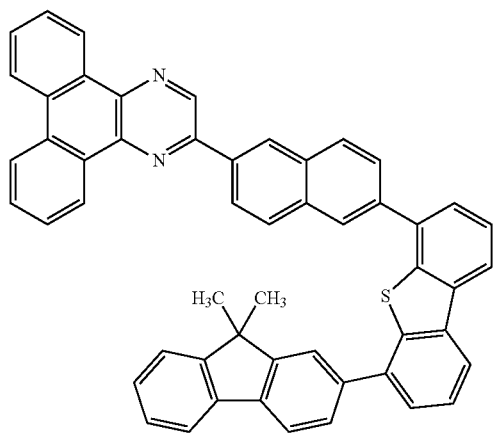
(112) 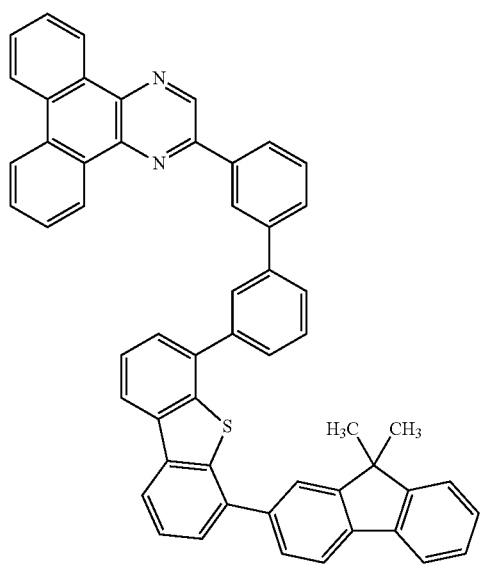
(113) 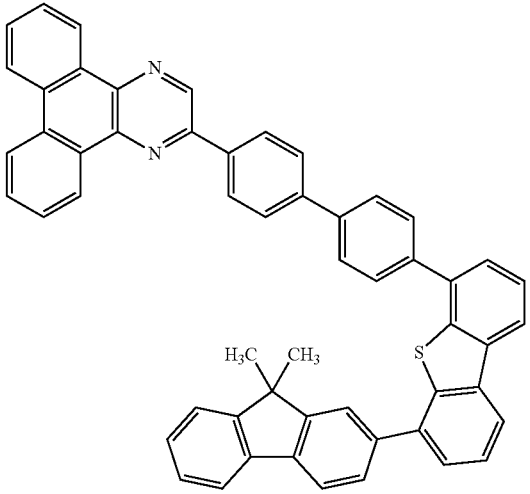
(114) 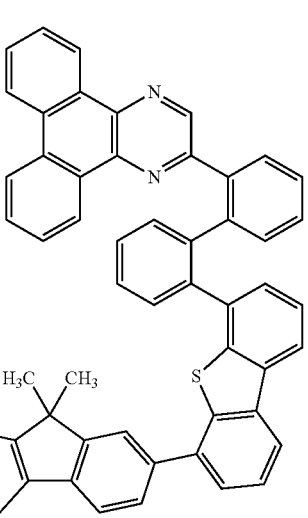
(115) 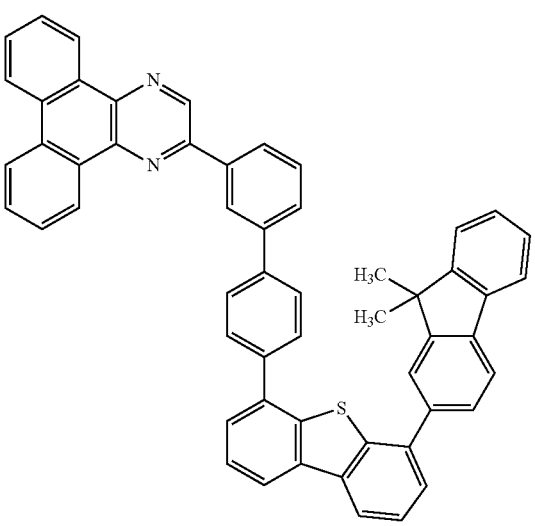

(116)
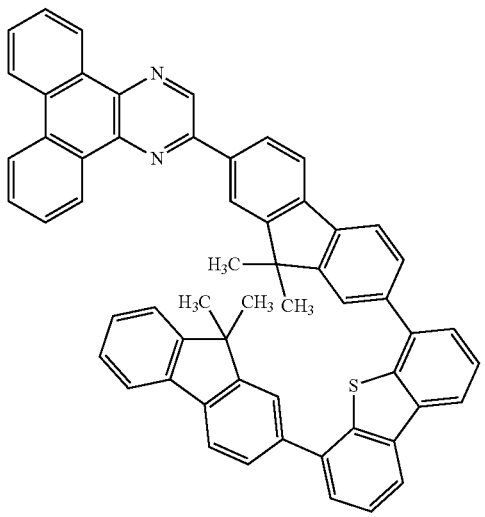
(117)
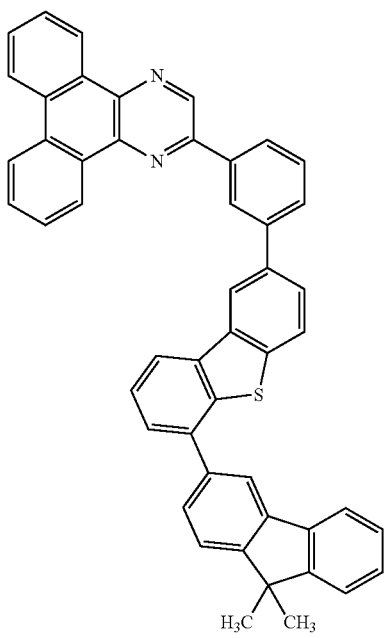
(118)
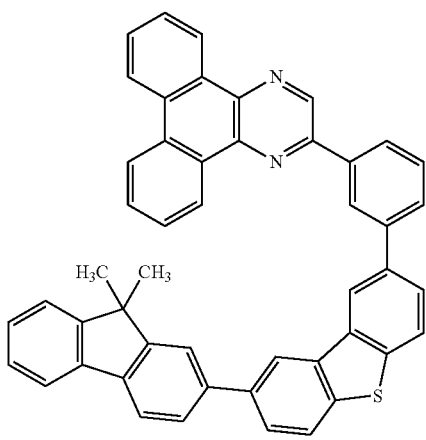
(119)
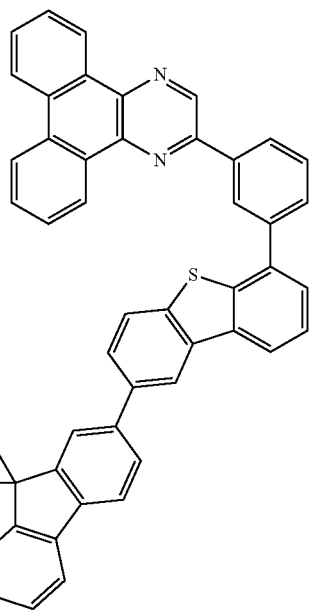
(120)
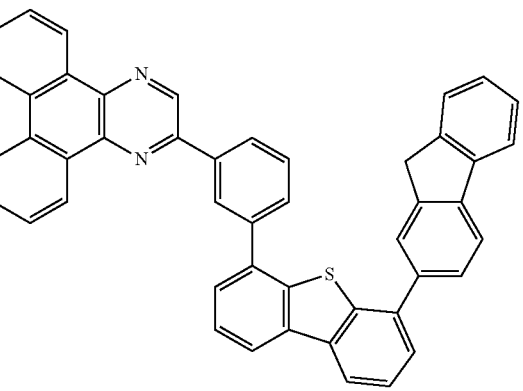
(121)

-continued
(122)
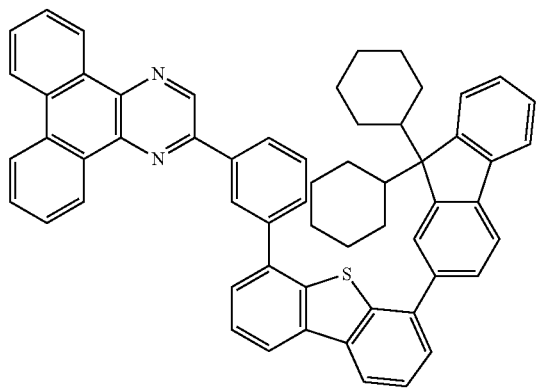
(123)
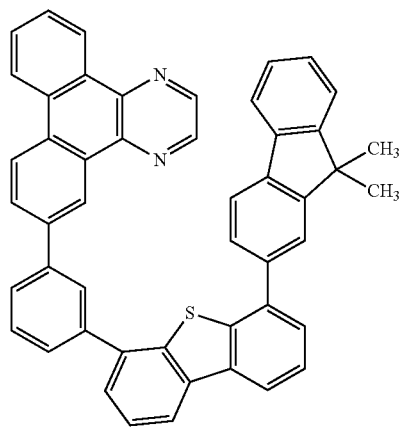
(124)
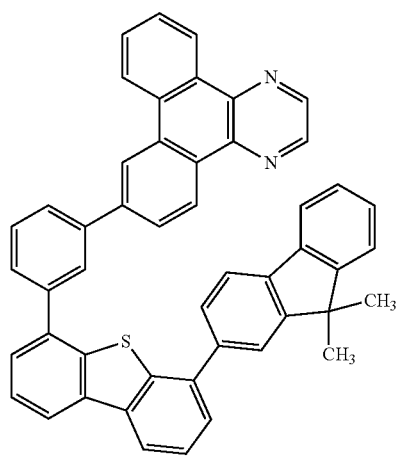
-continued
(125)
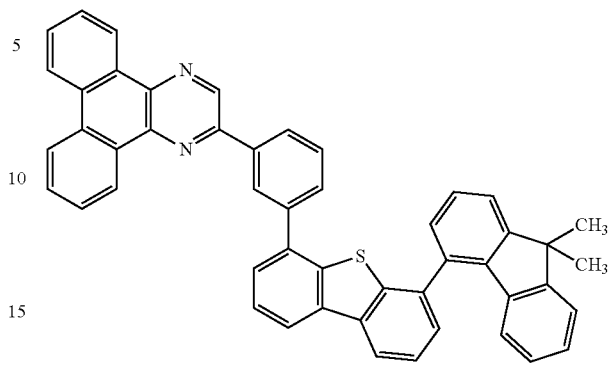
(126)
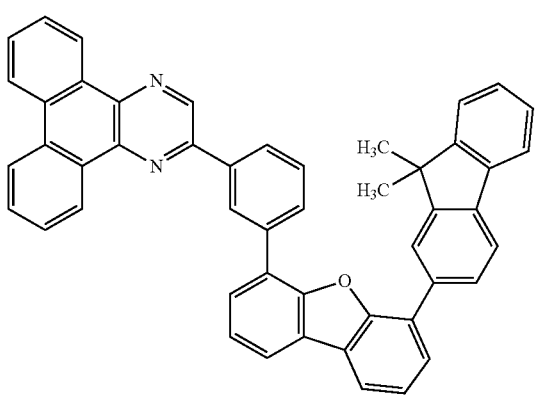
(127)
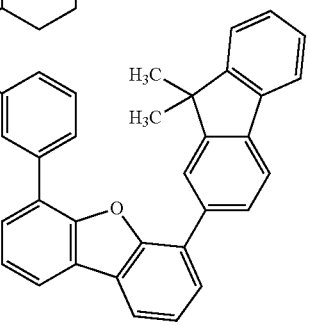

(128)
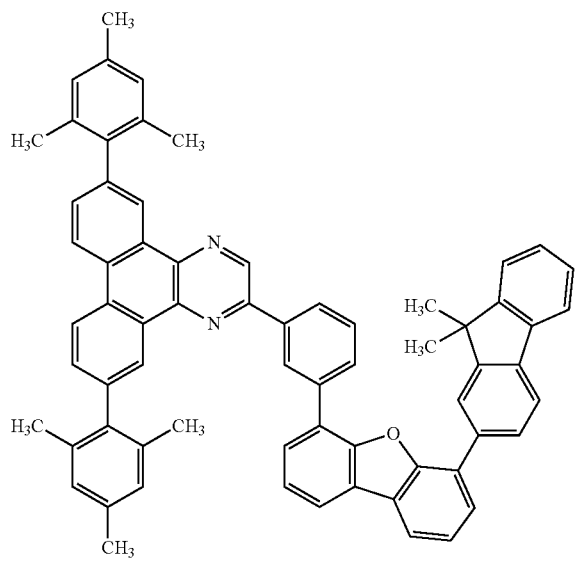
(129)
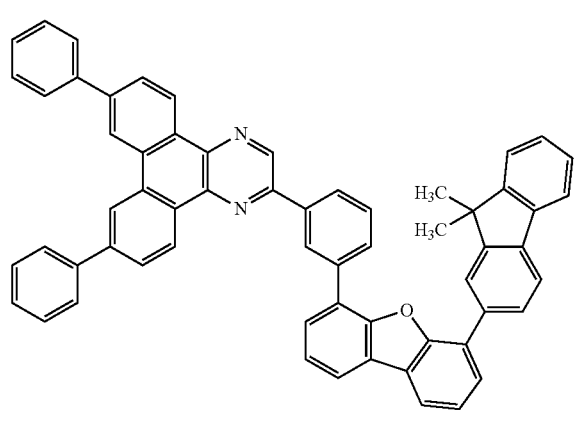
(130)
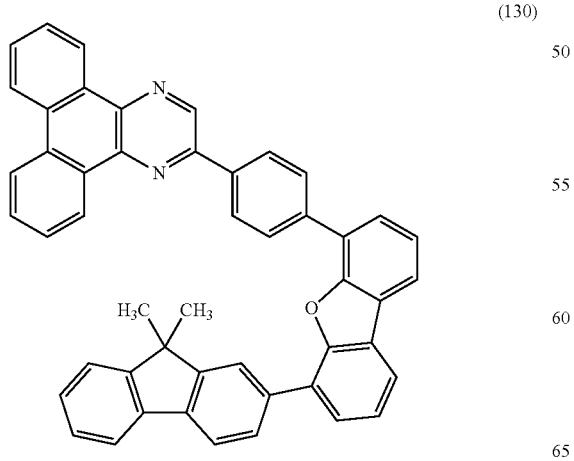
(131)
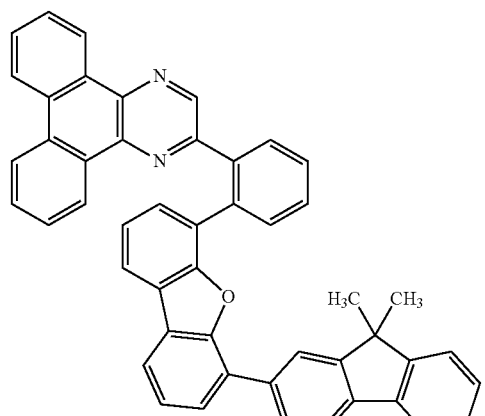
(132)
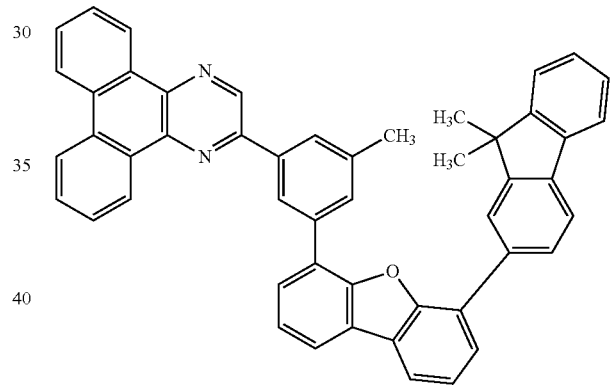
(133)
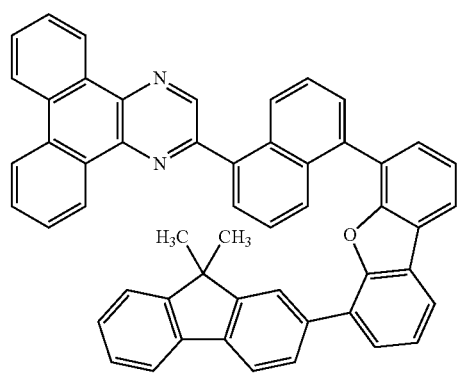

-continued
(134)
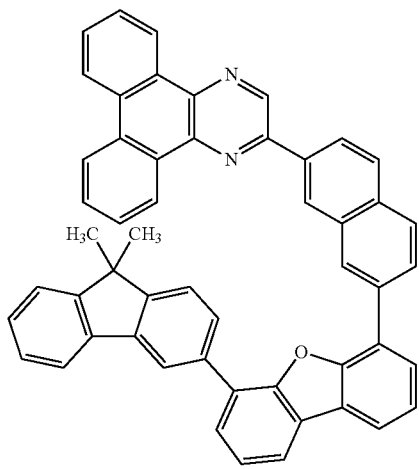
(135)
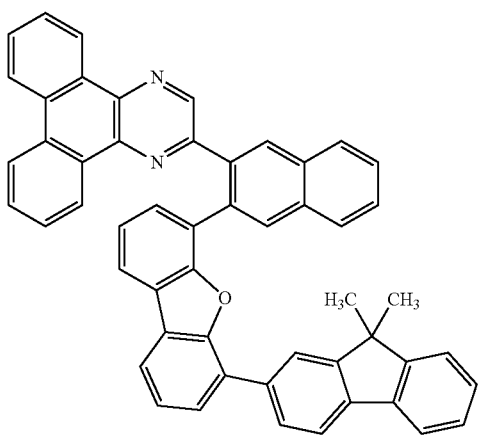
(136)
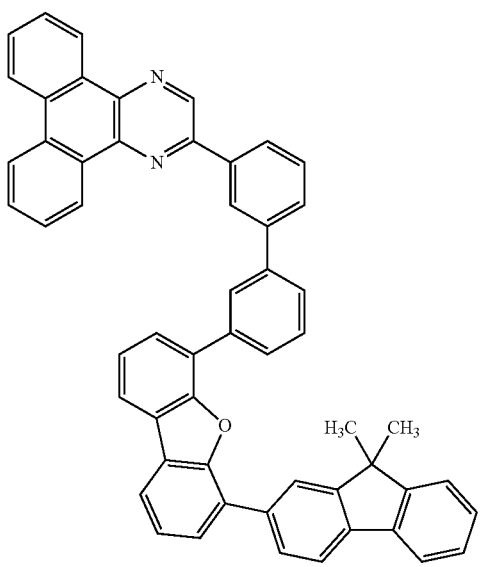
-continued
(137)
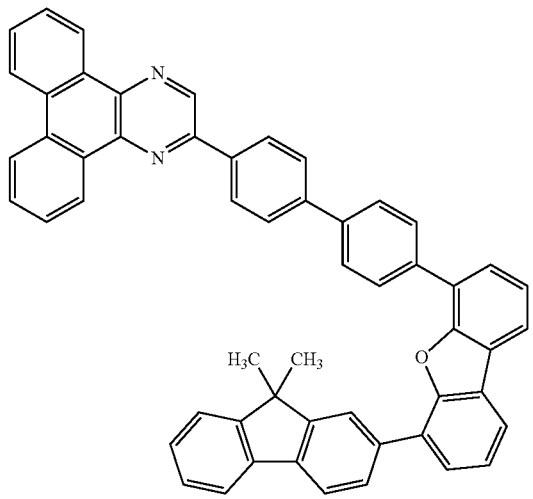
(138)
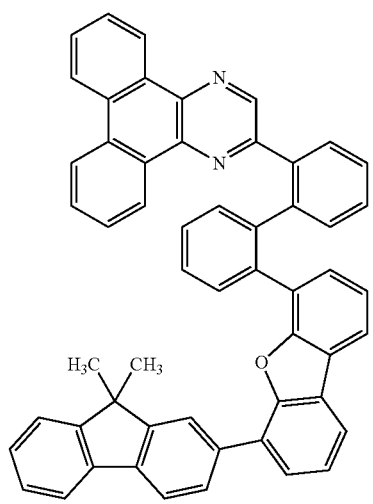
(139)
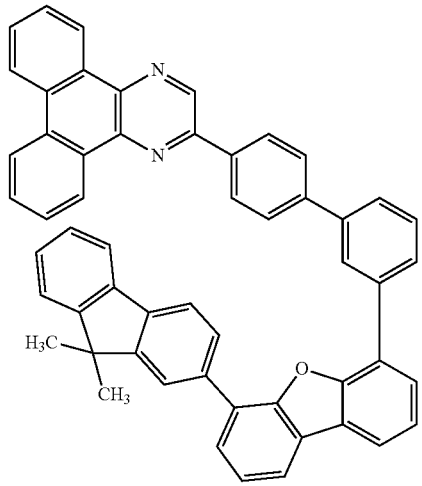

(140)
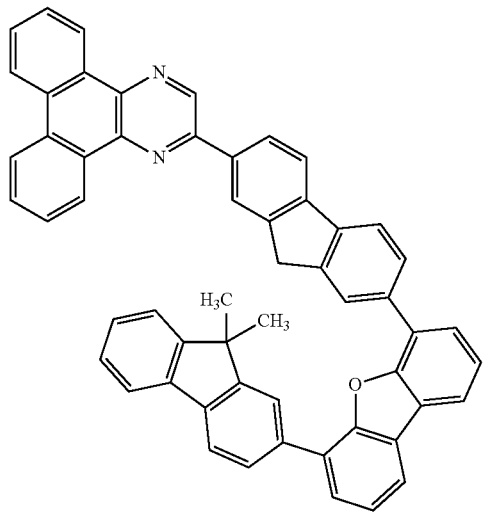
(143)
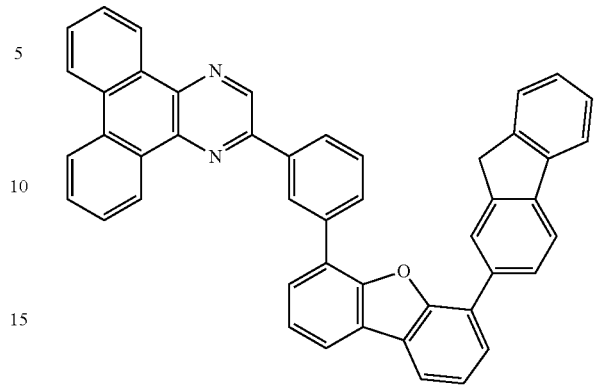
(144)
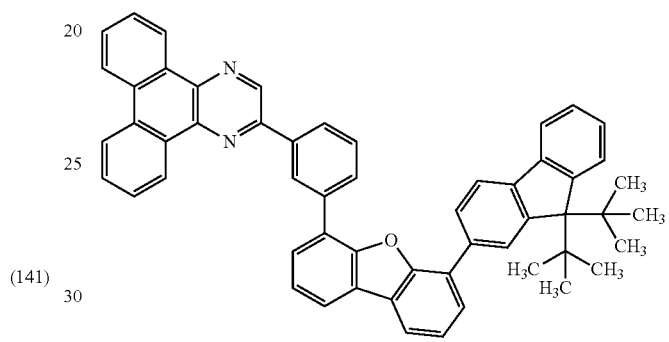
(141)
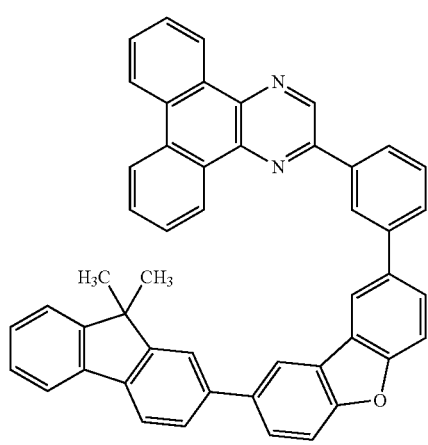
(145)
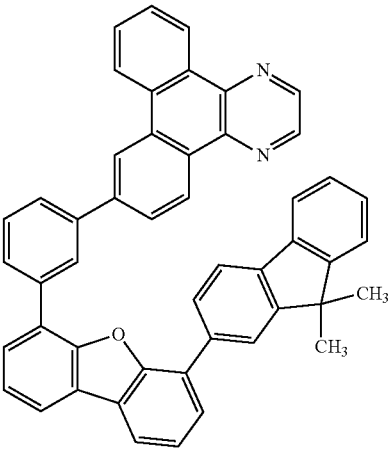
(142)
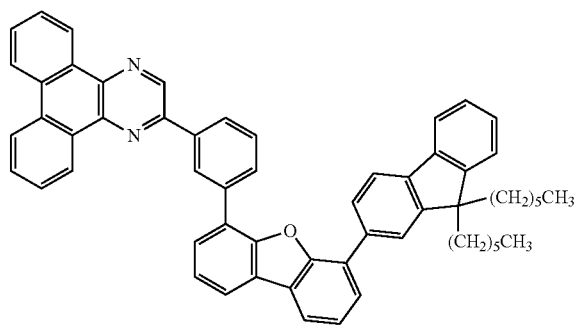
(146)
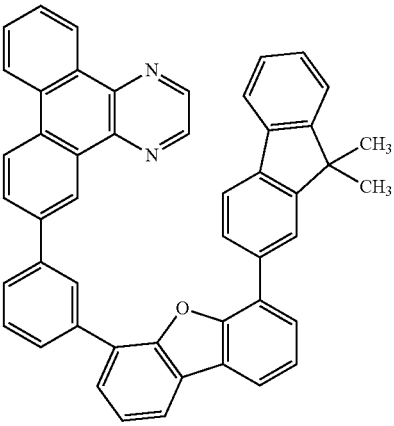

-continued

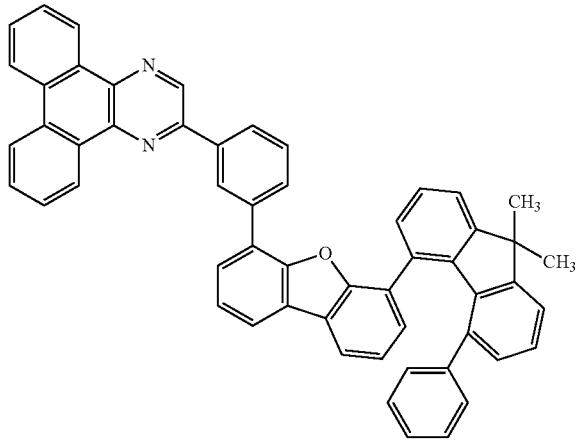

(147)

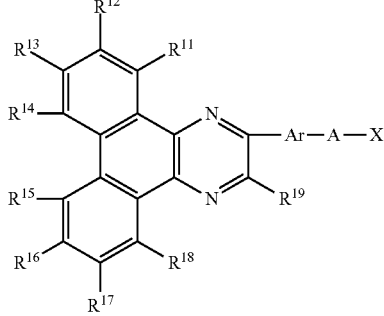

(G1)

In Synthesis Scheme (A-1), A represents any one of a substituted or unsubstituted dibenzothiophenylene group and a substituted or unsubstituted dibenzofuranylene group, X represents a substituted or unsubstituted fluorenyl group, each of $R^{11}$ to $R^{19}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

In Synthesis Scheme (A-1), Y represents any one of a halogen and a triflate group. When Y represents a halogen, chlorine, bromine, or iodine is particularly preferable as the halogen.

In Synthesis Scheme (A-1), when the compound (a2) is a boronic acid, $R^{43}$ and $R^{44}$ represent hydrogen. The compound (a2) may be an organoboron compound, in which, for example, a boronic acid is protected with ethylene glycol or the like. When the compound (a2) is an organoboron compound, each of $R^{43}$ and $R^{44}$ independently represents an alkyl group having 1 to 6 carbon atoms. In that case, $R^{43}$ and $R^{44}$ may be the same or different and may be bonded to each other to form a ring.

Examples of the palladium catalyst that can be used in Synthesis Scheme (A-1) include palladium(II) acetate and tetrakis(triphenylphosphine)palladium(0). Examples of a ligand of the palladium catalyst which can be used in Synthesis Scheme (A-1) include tri(ortho-tolyl)phosphine, triphenylphosphine, and tricyclohexylphosphine. In addition, examples of the base that can be used include organic bases such as sodium tert-butoxide, and inorganic bases such as potassium carbonate and sodium carbonate. Examples of solvents that can be used are as follows: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. The mixed solvent of toluene and water or the mixed solvent of toluene, ethanol, and water is preferable. The reagents that can be used in the reaction are not limited thereto.

Alternatively, an organoboron compound or a boronic acid of a dibenzo[f,h]quinoxaline derivative (specifically, the compound (a1) in which Y represents an organoboron group or a boronic acid group) may be coupled with a halogen compound of an aryl derivative having a dibenzo- A variety of reactions can be applied to a method for synthesizing the compound of one embodiment of the present invention. For example, synthesis reactions described below enable the synthesis of the compound of one embodiment of the present invention represented by General Formula (G1). Note that the methods for synthesizing the compound of one embodiment of the present invention are not limited to the synthesis methods below.

<Synthesis Method 1 of Compound Represented by General Formula (G1)>

The compound represented by General Formula (G1) can be synthesized under Synthesis Scheme (A-1). That is, a halogen compound of a dibenzo[f,h]quinoxaline derivative or a dibenzo[f,h]quinoxaline derivative having a triflate group (a1) is coupled with a boronic acid or an organoboron compound of an aryl derivative having a dibenzothiophenylene or dibenzofuranylene group to which a fluorenyl group (a2) is bonded, by the Suzuki-Miyaura reaction using a palladium catalyst, so that the compound represented by General Formula (G1) can be obtained.

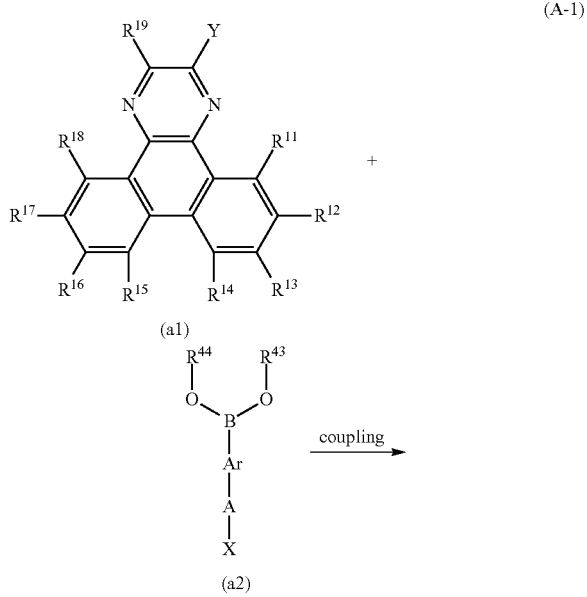

(A-1)

thiophenylene or dibenzofuranylene group to which a fluorenyl group is bonded or an aryl derivative having a triflate group and a dibenzothiophenylene or dibenzofuranylene group to which a fluorenyl group is bonded (specifically, the compound (a2) in which the group bonded to Ar is not an organoboron group or a boronic acid group but a halogen or a triflate group) by the Suzuki-Miyaura reaction.

<Synthesis Method 2 of Compound Represented by General Formula (G1)>

The compound represented by General Formula (G1) can also be synthesized under Synthesis Scheme (A-2). That is, a halogen compound of an aryl derivative to which a dibenzo[f,h]quinoxalinyl group is bonded or an aryl derivative to which a dibenzo[f,h]quinoxalinyl group is bonded and which has a triflate group (a3) is coupled with a boronic acid or an organoboron compound of a dibenzothiophene or dibenzofuran derivative to which a fluorenyl group is bonded (a4) by the Suzuki-Miyaura reaction using a palladium catalyst, so that the compound represented by General Formula (G1) can be obtained.

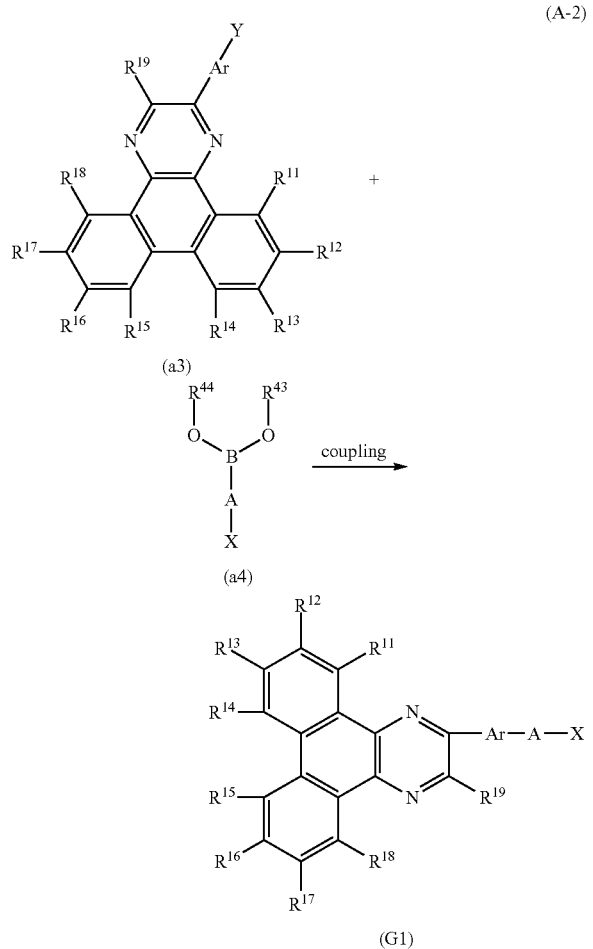

In Synthesis Scheme (A-2), A represents any one of a substituted or unsubstituted dibenzothiophenylene group and a substituted or unsubstituted dibenzofuranylene group, X represents a substituted or unsubstituted fluorenyl group, each of $R^{11}$ to $R^{19}$ independently represents any one of hydrogen, an alkyl group having 1 to 6 carbon atoms, and a substituted or unsubstituted aryl group having 6 to 13 carbon atoms, and Ar represents a substituted or unsubstituted arylene group having 6 to 30 carbon atoms.

In Synthesis Scheme (A-2), Y represents any one of a halogen and a triflate group. When Y represents a halogen, chlorine, bromine, or iodine is particularly preferable as the halogen.

In Synthesis Scheme (A-2), when the compound (a4) is a boronic acid, $R^{43}$ and $R^{44}$ represent hydrogen. The compound (a4) may be an organoboron compound, in which, for example, a boronic acid is protected with ethylene glycol or the like. When the compound (a4) is an organoboron compound, each of $R^{43}$ and $R^{44}$ independently represents an alkyl group having 1 to 6 carbon atoms. In that case, $R^{43}$ and $R^{44}$ may be the same or different and may be bonded to each other to form a ring.

Examples of the palladium catalyst that can be used in Synthesis Scheme (A-2) include palladium(II) acetate and tetrakis(triphenylphosphine)palladium(0). Examples of a ligand of the palladium catalyst which can be used in Synthesis Scheme (A-2) include tri(ortho-tolyl)phosphine, triphenylphosphine, and tricyclohexylphosphine. In addition, examples of the base that can be used include organic bases such as sodium tert-butoxide, and inorganic bases such as potassium carbonate and sodium carbonate. Examples of solvents that can be used are as follows: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. The mixed solvent of toluene and water or the mixed solvent of toluene, ethanol, and water is preferable. The reagents that can be used in the reaction are not limited thereto.

Alternatively, an organoboron compound or a boronic acid of an aryl derivative to which a dibenzo[f,h]quinoxalinyl group is bonded (specifically, the compound (a3) in which Y represents an organoboron group or a boronic acid group) may be coupled with a halogen compound of a dibenzothiophene or dibenzofuran derivative to which a fluorenyl group is bonded or a dibenzothiophene or dibenzofuran derivative to which a fluorenyl group is bonded and which has a triflate group (specifically, the compound (a4) in which the group bonded to Ar is not an organoboron group or a boronic acid group but a halogen or a triflate group) by the Suzuki-Miyaura reaction.

Thus, the compound of this embodiment can be synthesized.

In a light-emitting element, the compound of this embodiment can be favorably used as a host material of a light-emitting layer, in which a light-emitting substance is dispersed, or a material of an electron-transport layer. By the use of the compound of this embodiment, a light-emitting element with a long lifetime can be provided. In addition, a light-emitting element with high reliability can be provided by the use of the compound of this embodiment.

This embodiment can be combined with any other embodiment as appropriate.

(Embodiment 2)

In this embodiment, light-emitting elements of embodiments of the present invention will be described with reference to FIGS. 1A to 1D.

A light-emitting element of one embodiment of the present invention has a layer containing the compound described in Embodiment 1 between a pair of electrodes.

The compound included in the light-emitting element of one embodiment of the present invention is sterically bulky and highly resistant to heat. Accordingly, the use of the compound enables a light-emitting element to have a long lifetime. In addition, the compound has high solubility. By including the compound of one embodiment of the present invention from which impurities are sufficiently removed, a light-emitting element can have suppressed initial deterioration and high reliability.

Furthermore, the compound can accept electrons and holes since the compound has a dibenzo[f,h]quinoxaline skeleton as an electron-transport skeleton and a dibenzothiophene or dibenzofuran skeleton as a hole-transport skeleton. Accordingly, by the use of the compound as a host material of a light-emitting layer, electrons and holes recombine in the light-emitting layer and it is possible to inhibit a reduction in lifetime of the light-emitting element. That is, a preferred embodiment of the present invention is a light-emitting element including, between a pair of electrodes, a light-emitting layer containing a light-emitting substance (guest material) and the above compound serving as a host material in which the light-emitting substance is dispersed.

The light-emitting element of this embodiment includes a layer (EL layer) containing a light-emitting organic compound between a pair of electrodes (a first electrode and a second electrode). One of the first electrode and the second electrode functions as an anode, and the other functions as a cathode. In this embodiment, the EL layer contains the compound of one embodiment of the present invention which is described in Embodiment 1.

<<Structural Example of Light-emitting Element>>

A light-emitting element illustrated in FIG. 1A includes an EL layer 203 between a first electrode 201 and a second electrode 205. In this embodiment, the first electrode 201 serves as an anode and the second electrode 205 serves as a cathode.

When a voltage higher than the threshold voltage of the light-emitting element is applied between the first electrode 201 and the second electrode 205, holes are injected from the first electrode 201 side to the EL layer 203 and electrons are injected from the second electrode 205 side to the EL layer 203. The injected electrons and holes recombine in the EL layer 203 and a light-emitting substance contained in the EL layer 203 emits light.

The EL layer 203 includes at least a light-emitting layer 303 containing a light-emitting substance.

Furthermore, when a plurality of light-emitting layers are provided in the EL layer and emission colors of the layers are made different, light emission of a desired color can be provided from the light-emitting element as a whole. For example, the emission colors of first and second light-emitting layers are complementary in a light-emitting element having the two light-emitting layers, so that the light-emitting element can be made to emit white light as a whole. Note that "complementary colors" refer to colors that can produce an achromatic color when mixed. In other words, when light components obtained from substances that emit light of complementary colors are mixed, white emission can be obtained. Furthermore, the same applies to a light-emitting element having three or more light-emitting layers.

In addition to the light-emitting layer, the EL layer 203 may further include a layer containing a substance with a high hole-injection property, a substance with a high hole-transport property, a substance with a high electron-transport property, a substance with a high electron-injection property, a substance with a bipolar property (a substance with a high electron-transport property and a high hole-transport property), or the like. Either a low molecular compound or a high molecular compound can be used for the EL layer 203, and an inorganic compound may be used.

Figure 1B:
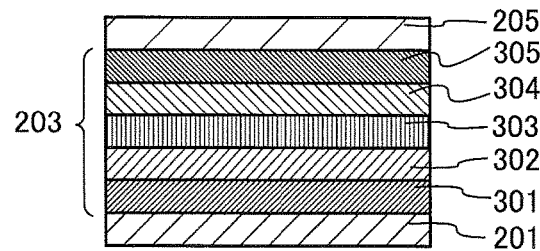

A light-emitting element illustrated in FIG. 1B includes the EL layer 203 between the first electrode 201 and the second electrode 205, and in the EL layer 203, a hole-injection layer 301, a hole-transport layer 302, the light-emitting layer 303, an electron-transport layer 304, and an electron-injection layer 305 are stacked in that order from the first electrode 201 side.

The compound of one embodiment of the present invention is preferably used for the light-emitting layer 303 or the electron-transport layer 304. In this embodiment, an example is described in which the compound of one embodiment of the present invention is used as the host material in the light-emitting layer 303.

Figure 1C:
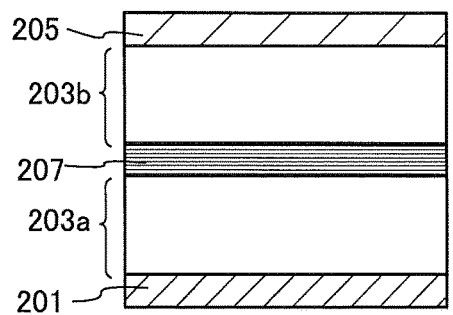
Figure 1D:
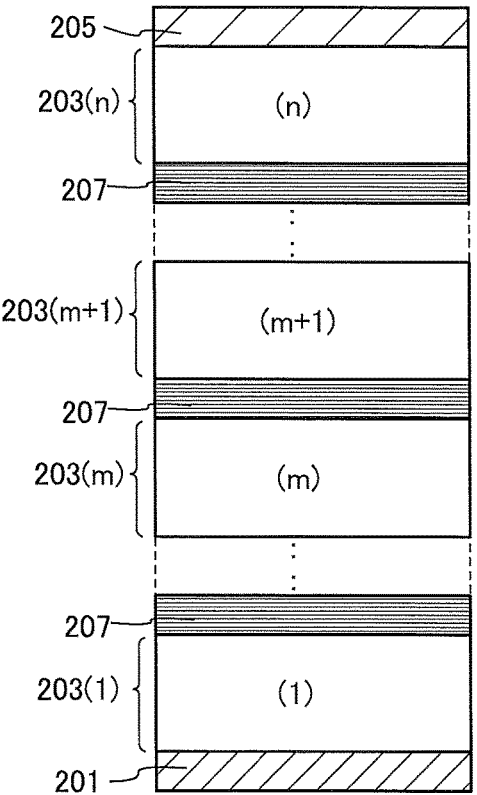

As in light-emitting elements illustrated in FIGS. 1C and 1D, a plurality of EL layers may be stacked between the first electrode 201 and the second electrode 205. In this case, an intermediate layer 207 is preferably provided between the stacked EL layers. The intermediate layer 207 includes at least a charge-generation region.

For example, the light-emitting element illustrated in FIG. 1C includes the intermediate layer 207 between a first EL layer 203a and a second EL layer 203b. The light-emitting element illustrated in FIG. 1D includes n EL layers (n is a natural number of 2 or more), and the intermediate layers 207 between the EL layers.

The behaviors of electrons and holes in the intermediate layer 207 provided between the EL layer 203($m$) and the EL layer 203($m$+1) will be described. When a voltage higher than the threshold voltage of the light-emitting element is applied between the first electrode 201 and the second electrode 205, holes and electrons are generated in the intermediate layer 207, and the holes move into the EL layer 203($m$+1) provided on the second electrode 205 side and the electrons move into the EL layer 203($m$) provided on the first electrode 201 side. The holes injected into the EL layer 203($m$+1) recombine with electrons injected from the second electrode 205 side, so that a light-emitting substance contained in the EL layer 203($m$+1) emits light. Furthermore, the electrons injected into the EL layer 203($m$) recombine with holes injected from the first electrode 201 side, so that a light-emitting substance contained in the EL layer 203($m$) emits light. Thus, the holes and electrons generated in the intermediate layer 207 cause light emission in different EL layers.

Note that the EL layers can be provided in contact with each other with no intermediate layer interposed therebetween when these EL layers allow the same structure as the intermediate layer to be formed therebetween. For example, when the charge-generation region is formed over one surface of an EL layer, another EL layer can be provided in contact with the surface.

Furthermore, when emission colors of the EL layers are made different, light emission of a desired color can be provided from the light-emitting element as a whole. For example, the emission colors of the first and second EL layers are complementary in a light-emitting element having the two EL layers, so that the light-emitting element can be made to emit white light as a whole. The same applies to a light-emitting element having three or more EL layers.

<<Materials of Light-emitting Element>>

Examples of materials which can be used for each layer will be given below. Note that each layer is not limited to a single layer, and may be a stack including two or more layers.

<Anode>

The electrode serving as the anode (the first electrode 201 in this embodiment) can be formed using one or more kinds of conductive metals, conductive alloys, conductive compounds, and the like. In particular, it is preferable to use a material with a high work function (4.0 eV or more). The examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, titanium, and a nitride of a metal material (e.g., titanium nitride).

When the anode is in contact with the charge-generation region, any of a variety of conductive materials can be used regardless of their work functions; for example, aluminum, silver, an alloy containing aluminum, or the like can be used.

<Cathode>

The electrode serving as the cathode (the second electrode 205 in this embodiment) can be formed using one or more kinds of conductive metals, conductive alloys, conductive compounds, and the like. In particular, it is preferable to use a material with a low work function (3.8 eV or less). The examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

Note that when the cathode is in contact with the charge-generation region, any of a variety of conductive materials can be used regardless of its work function. For example, ITO or indium tin oxide containing silicon or silicon oxide can be used.

The electrodes may be formed separately by a vacuum evaporation method or a sputtering method. Alternatively, when a silver paste or the like is used, a coating method or an inkjet method may be used.

<Light-emitting Layer>

The light-emitting layer 303 contains a light-emitting substance. In an example described in this embodiment, the light-emitting layer 303 contains a guest material and a host material in which the guest material is dispersed and the compound of one embodiment of the present invention is used as the host material. The compound of one embodiment of the present invention can be favorably used as a host material in a light-emitting layer when a light-emitting substance is a phosphorescent compound emitting light in a wavelength range from red to green or a fluorescent compound.

When the light-emitting layer has the structure in which the guest material is dispersed in the host material, the crystallization of the light-emitting layer can be inhibited. Furthermore, it is possible to inhibit concentration quenching due to high concentration of the guest material; thus, the light-emitting element can have higher emission efficiency.

In addition to the guest material and the host material, the light-emitting layer may contain another compound. Furthermore, in addition to the light-emitting layer containing the compound of one embodiment of the present invention, the light-emitting element of one embodiment of the present invention may include another light-emitting layer. In that case, a fluorescent compound, a phosphorescent compound, or a substance emitting thermally activated delayed fluorescence can be used as the light-emitting substance, and a compound to be described below which easily accepts electrons or a compound to be described below which easily accepts holes can be used as the host material.

Note that it is preferable that the $T_1$ level of the host material (or a material other than the guest material in the light-emitting layer) be higher than the $T_1$ level of the guest material. This is because, when the $T_1$ level of the host material is lower than that of the guest material, the triplet excitation energy of the guest material, which is to contribute to light emission, is quenched by the host material and accordingly the emission efficiency is reduced.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) have a large overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because the phosphorescence spectrum of the host material is located on the longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For this reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, it is preferable that in a light-emitting layer of a light-emitting element which uses a phosphorescent compound as a guest material, a third substance be contained in addition to the phosphorescent compound and the host material (which are respectively regarded as a first substance and a second substance contained in the light-emitting layer), and the host material forms an exciplex (also referred to as excited complex) in combination with the third substance. In that case, the host material and the third substance form an exciplex at the time of recombination of carriers (electrons and holes) in the light-emitting layer. Thus, in the light-emitting layer, fluorescence spectra of the host material and the third substance are converted into an emission spectrum of the exciplex which is located on a longer wavelength side. Moreover, when the host material and the third substance are selected such that the emission spectrum of the exciplex has a large overlap with the absorption spectrum of the guest material, energy transfer from a singlet excited state can be maximized. Note that also in the case of a triplet excited state, energy transfer from the exciplex, not the host material, is considered to occur. In one embodiment of the present invention to which such a structure is applied, energy transfer efficiency can be improved owing to energy transfer utilizing an overlap between an emission spectrum of an exciplex and an absorption spectrum of a phosphorescent compound; accordingly, a light-emitting element with high external quantum efficiency can be provided.

As the guest material, a phosphorescent compound to be described below can be used. Although any combination of the host material and the third substance can be used as long as an exciplex is formed, a compound which easily accepts electrons (a compound having an electron-trapping property) and a compound which easily accepts holes (a compound having a hole-trapping property) are preferably combined. The compound of one embodiment of the present invention can be used as a compound having an electron-trapping property.

Thus, the light-emitting element of one embodiment of the present invention includes, between a pair of electrodes, a light-emitting layer containing a phosphorescent compound emitting light in a wavelength range from red to green, the compound of one embodiment of the present invention, and a compound which easily accepts holes.

Examples of a compound which easily accepts holes and which can be used as the host material or the third substance are a π-electron rich heteroaromatic compound (e.g., a carbazole derivative or an indole derivative) and an aromatic amine compound.

Specifically, the following examples can be given: N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 3-[N-(1-naphthyl)-N-(9-phenyl-carbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), and 3,6-bis[N-(4-diphenylaminophenyl)-N-(1-naphthyl)amino]-9-phenylcarbazole (abbreviation: PCzTPN2).

The following examples can also be given: aromatic amine compounds such as 4,4'-bis[N-(1-naphthyl)-N-phenylamino]biphenyl (abbreviation: NPB or α-NPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4,4',4"-tris(N-carbazolyl)triphenylamine (abbreviation: TCTA), 4-phenyl-4'-(9-phenylfluoren-9-yl)triphenylamine (abbreviation: BPAFLP), and 4,4'-bis[N-(9,9-dimethylfluoren-2-yl)-N-phenylamino]biphenyl (abbreviation: DFLDPBi); and carbazole derivatives such as 4,4'-di(N-carbazolyl)biphenyl (abbreviation: CBP), 9-[4-(10-phenyl-9-anthracenyl)phenyl]-9H-carbazole (abbreviation: CzPA), and 9-phenyl-3-[4-(10-phenyl-9-anthryl)phenyl]-9H-carbazole (abbreviation: PCzPA). In addition, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}-phenyl)methacrylamide] (abbreviation: PTPDMA), and poly[N,N'-bis(4-butylphenyl)-N,N'-bis(phenyl)benzidine] (abbreviation: Poly-TPD) can be given.

Examples of the compound which easily accepts electrons and which can be used as the host material or the third substance include the compound of one embodiment of the present invention, a π-electron deficient heteroaromatic compound such as a nitrogen-containing heteroaromatic compound, a metal complex having a quinoline skeleton or a benzoquinoline skeleton, and a metal complex having an oxazole-based ligand or a thiazole-based ligand.

Specific examples include the following: metal complexes such as bis(10-hydroxybenzo[h]quinolinato)beryllium (abbreviation: BeBq$_2$), bis(2-methyl-8-quinolinolato)(4-phenylphenolato)aluminum (abbreviation: BAlq), bis(8-quinolinolato)zinc(II) (abbreviation: Znq), bis[2-(2-hydroxyphenyl)benzoxazolato]zinc (abbreviation: Zn(BOX)$_2$), and bis[2-(2-hydroxyphenyl)benzothiazolato]zinc (abbreviation: Zn(BTZ)$_2$); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 3,5DCzPPy), 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above materials, heterocyclic compounds having quinoxaline skeletons or dibenzoquinoxaline skeletons, heterocyclic compounds having diazine skeletons, and heterocyclic compounds having pyridine skeletons are preferable because of their high reliability.

The following examples can also be given: metal complexes having quinoline skeletons or benzoquinoline skeletons, such as tris(8-quinolinolato)aluminum (abbreviation: Alq) and tris(4-methyl-8-quinolinolato)aluminum (abbreviation: Almq$_3$); and heteroaromatic compounds such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), and 4,4'-bis(5-methylbenzoxazol-2-yl)stilbene (abbreviation: BzOs). In addition, high molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be given.

The materials which can be used as the host material or the third substance are not limited to the above materials as long as the material used as the host material forms an exciplex in combination with the material used as the third substance, an emission spectrum of the exciplex overlaps with an absorption spectrum of the guest material, and a peak of the emission spectrum of the exciplex is located on a longer wavelength side than a peak of the absorption spectrum of the guest material.

Note that when a compound which easily accepts electrons and a compound which easily accepts holes are used for the host material and the third substance, carrier balance can be controlled by the mixture ratio of the compounds. Specifically, the ratio of the host material to the third substance is preferably from 1:9 to 9:1.

Furthermore, the exciplex may be formed at the interface between two layers. For example, when a layer containing the compound which easily accepts electrons and a layer containing the compound which easily accepts holes are stacked, the exciplex is formed in the vicinity of the interface thereof. These two layers may be used as the light-emitting layer in the light-emitting element of one embodiment of the present invention. In that case, the phosphorescent compound may be added to the vicinity of the interface. The phosphorescent compound may be added to one of the two layers or both.

<<Guest Material>>

Examples of fluorescent compounds that can be used for the light-emitting layer 303 are given. Examples of materials that emit blue light are as follows: N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis(dibenzofuran-4-yl)-N,N'-diphenylpyrene-1,6-diamine (abbreviation: 1,6FrAPm-II), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA). Examples of materials that emit green light are as follows: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA). Examples of materials that emit yellow light are as follows: rubrene and 5,12-bis(1,1'-biphenyl-4-yl)-6,11-diphenyltetracene (abbreviation: BPT). Examples of materials that emit red light are as follows: N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-α]fluoranthene-3,10-diamine (abbreviation: p-mPhAFD).

Examples of phosphorescent compounds that can be used for the light-emitting layer 303 are given. For example, a phosphorescent compound having an emission peak at 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptzl-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N, C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). Among the materials given above, the organometallic iridium complexes having 4H-triazole skeletons have high reliability and high emission efficiency and are thus especially preferable.

Examples of the phosphorescent compound having an emission peak at 520 nm to 600 nm include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium(III) (endo- and exo-mixture) (abbreviation: [Ir(nbppm)$_2$(acac)]), (acetylacetonato)bis[5-methyl-6-(2-methylphenyl)-4-phenylpyrimidinato]iridium (III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). Among the above materials, the organometallic iridium complexes having pyrimidine skeletons are particularly preferable because of their distinctively high reliability and emission efficiency.

Examples of the phosphorescent compound having an emission peak at 600 nm to 700 nm include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); a platinum complex such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the materials given above, the organometallic iridium complexes having pyrimidine skeletons have distinctively high reliability and emission efficiency and are thus especially preferable. Furthermore, the organometallic iridium complexes having pyrazine skeletons can provide red light emission with favorable chromaticity.

Alternatively, a high molecular compound can be used for the light-emitting layer 303. Examples of the materials that emit blue light include poly(9,9-dioctylfluorene-2,7-diyl) (abbreviation: POF), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH). Examples of the materials that emit green light include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]. Examples of the materials that emit orange to red light include poly[2-methoxy-5-(2-ethylhexoxy)-1,4-phenylenevinylene] (abbreviation: MEH-PPV), poly(3-butylthiophene-2,5-diyl), poly{[9,9-dihexyl-2,7-bis(1-cyanovinylene)fluorenylene]-alt-co-[2,5-bis(N,N'-diphenylamino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

<Hole-Transport Layer>

The hole-transport layer 302 contains a substance with a high hole-transport property.

The substance with a high hole-transport property is a substance having a hole-transport property higher than an electron-transport property, and is especially preferably a substance with a hole mobility of 10$^{-6}$ cm$^2$/Vs or more.

For the hole-transport layer 302, it is possible to use any of the compounds which easily accept holes and are described as examples of the substance applicable to the light-emitting layer 303.

It is also possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

<Electron-Transport Layer>

The electron-transport layer 304 contains a substance with a high electron-transport property.

The substance with a high electron-transport property is an organic compound having an electron-transport property higher than a hole-transport property, and is especially preferably a substance with an electron mobility of 10$^{-6}$ cm$^2$/Vs or more.

For the electron-transport layer 304, it is possible to use any of the compounds which easily accept electrons and are described as examples of the substance applicable to the light-emitting layer 303.

<Hole-Injection Layer>

The hole-injection layer 301 contains a substance with a high hole-injection property.

Examples of the substance with a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Alternatively, it is possible to use a phthalocyanine-based compound such as phthalocyanine (abbreviation: H$_2$Pc) or copper(II) phthalocyanine (abbreviation: CuPc).

Further alternatively, it is possible to use an aromatic amine compound which is a low molecular organic compound, such as TDATA, MTDATA, DPAB, DNTPD, 1,3,5-tris[N-(4-diphenylaminophenyl)-N-phenylamino]benzene (abbreviation: DPA3B), PCzPCA1, PCzPCA2, or PCzPCN1.

Further alternatively, it is possible to use a high molecular compound such as PVK, PV IPA, PTPDMA, or Poly-TPD, or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, any of a variety of conductive materials can be used for the anode regardless of their work functions. Materials contained in the charge-generation region will be described later.

<Electron-injection Layer>

The electron-injection layer 305 contains a substance with a high electron-injection property.

Examples of the substance with a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride. Electride can also be used. As an example of electride, a substance in which electrons are added at high concentration to an oxide containing calcium and aluminum can be given.

The electron-injection layer 305 may serve as the charge-generation region. When the electron-injection layer 305 in contact with the cathode serves as the charge-generation region, any of a variety of conductive materials can be used for the cathode regardless of their work functions. Materials contained in the charge-generation region will be described later.

<Charge-generation Region>

The charge-generation region may have either a structure in which an electron acceptor (acceptor) is added to an organic compound with a high hole-transport property or a structure in which an electron donor (donor) is added to an organic compound with a high electron-transport property. Alternatively, these structures may be stacked.

As examples of an organic compound with a high hole-transport property, the above materials which can be used for the hole-transport layer can be given, and as examples of an organic compound with a high electron-transport property, the above materials which can be used for the electron-transport layer can be given.

Furthermore, as the electron acceptor, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air, has a low hygroscopic property, and is easy to handle.

Furthermore, as the electron donor, it is possible to use an alkali metal, an alkaline earth metal, a rare earth metal, a metal belonging to Group 2 or Group 13 of the periodic table, or an oxide or a carbonate thereof. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

The above-described layers included in the EL layer 203 and the intermediate layer 207 can be formed separately by any of the following methods: an evaporation method (including a vacuum evaporation method), a transfer method, a printing method, an inkjet method, a coating method, and the like.

This embodiment can be freely combined with any of other embodiments.

(Embodiment 3)

In this embodiment, light-emitting devices of embodiments of the present invention will be described with reference to FIGS. 2A and 2B and FIGS. 3A to 3C.

Light-emitting devices including the light-emitting element of one embodiment of the present invention are described in this embodiment as examples. Since the light-emitting element has a long lifetime, light-emitting devices having high reliability can be provided.

Note that one embodiment of the present invention is not limited to these examples, and the light-emitting element of one embodiment of the present invention and the compound of one embodiment of the present invention are not necessarily included.

Figure 2A:
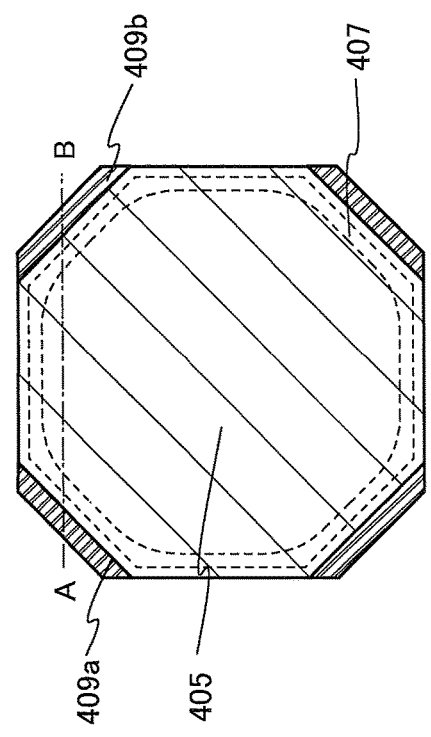
FIGS. 2A and 2B illustrate an example of a light-emitting device of one embodiment of the present invention.
Figure 2B:
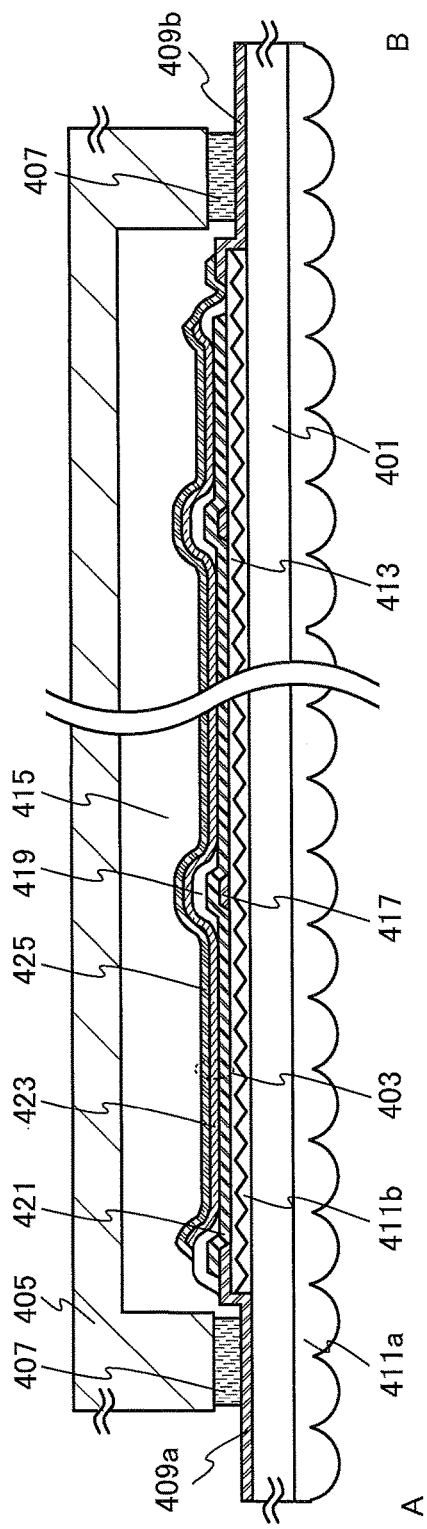

FIG. 2A is a plan view of a light-emitting device of one embodiment of the present invention, and FIG. 2B is a cross-sectional view taken along dashed-dotted line A-B in FIG. 2A.

In the light-emitting device of this embodiment, a light-emitting element 403 is provided in a space 415 surrounded by a support substrate 401, a sealing substrate 405, and a sealing material 407. The light-emitting element 403 is an organic EL element having a bottom-emission structure; specifically, a first electrode 421 which transmits visible light is provided over the support substrate 401, an EL layer 423 is provided over the first electrode 421, and a second electrode 425 which reflects visible light is provided over the EL layer 423. The EL layer 423 contains the compound of one embodiment of the present invention which is described in Embodiment 1.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

A light extraction structure 411a is preferably provided at the interface between the support substrate 401 and the atmosphere. When provided at the interface between the support substrate 401 and the atmosphere, the light extraction structure 411a can reduce light that cannot be extracted to the atmosphere because of total reflection, resulting in an increase in the light extraction efficiency of the light-emitting device.

In addition, a light extraction structure 411b is preferably provided at the interface between the light-emitting element 403 and the support substrate 401. When the light extraction structure 411b has unevenness, a planarization layer 413 is preferably provided between the light extraction structure 411b and the first electrode 421. Accordingly, the first electrode 421 can be a flat film, and generation of leakage current in the EL layer 423 due to the unevenness of the first electrode 421 can be prevented. Furthermore, because of the light extraction structure 411b at the interface between the planarization layer 413 and the support substrate 401, light that cannot be extracted to the atmosphere because of total reflection can be reduced, so that the light extraction efficiency of the light-emitting device can be increased.

As a material of the light extraction structure 411a and the light extraction structure 411b, a resin can be used, for example. Alternatively, for the light extraction structure 411a and the light extraction structure 411b, a hemispherical lens, a micro lens array, a film provided with an uneven structure, a light diffusing film, or the like can be used. For example, the light extraction structure 411a and the light extraction structure 411b can be formed by attaching the lens or film to the support substrate 401 with an adhesive or the like which has substantially the same refractive index as the support substrate 401 or the lens or film.

The surface of the planarization layer 413 which is in contact with the first electrode 421 is flatter than the surface of the planarization layer 413 which is in contact with the light extraction structure 411b. As a material of the planarization layer 413, glass, liquid, a resin, or the like having a light-transmitting property and a high refractive index can be used.

Figure 3A:
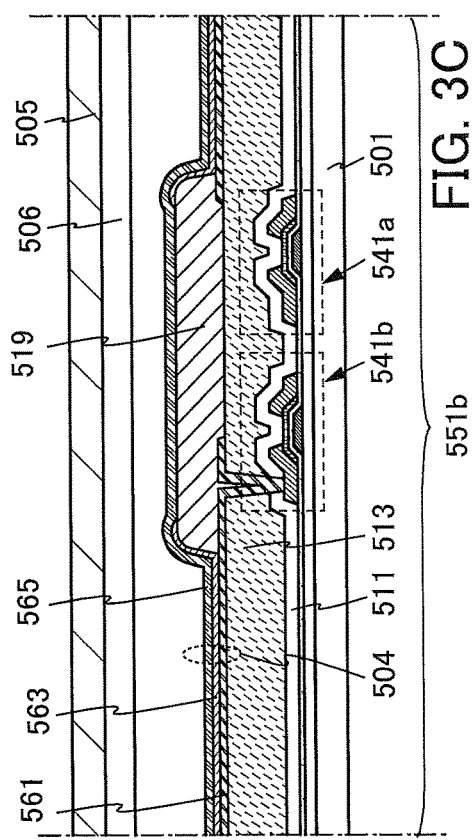
FIGS. 3A to 3C illustrate examples of a light-emitting device of one embodiment of the present invention.
Figure 3C:
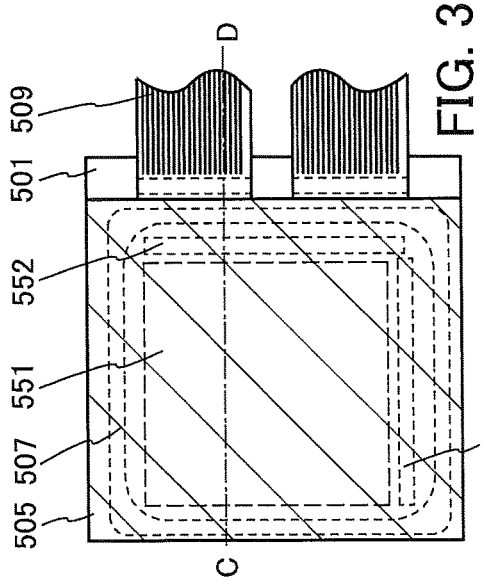
Figure 3B:
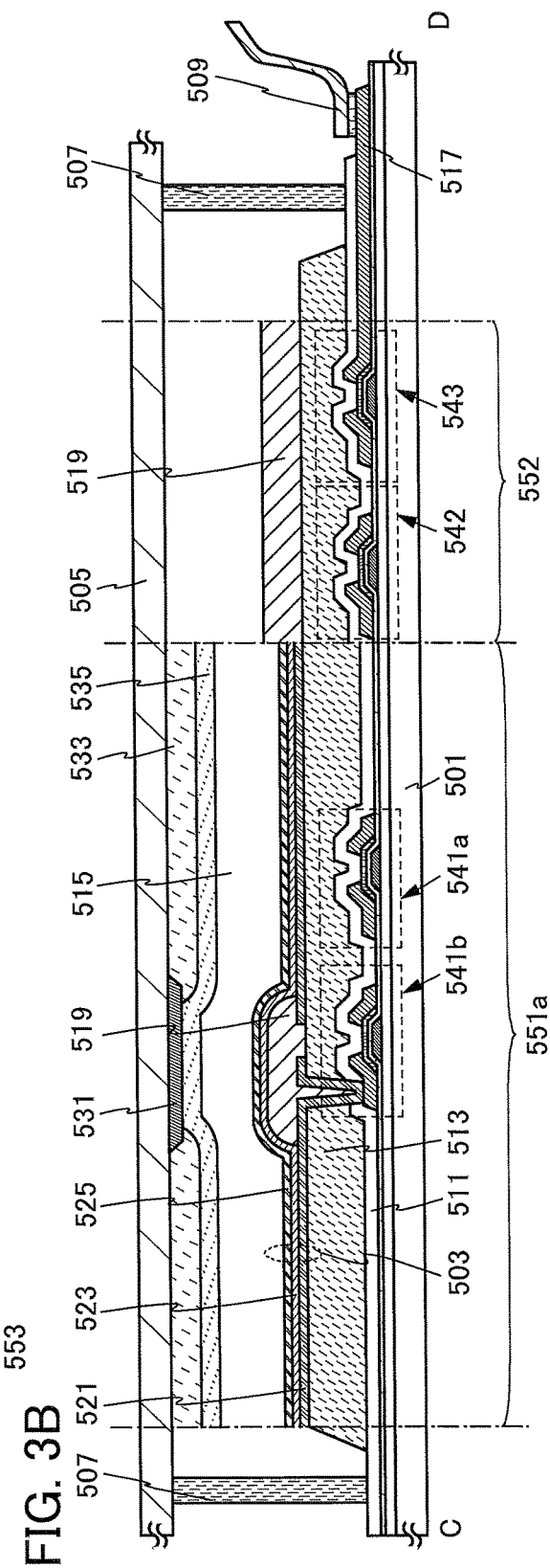

FIG. 3A is a plan view of a light-emitting device of one embodiment of the present invention, FIG. 3B is a cross-sectional view taken along dashed-dotted line C-D in FIG. 3A, and FIG. 3C is a cross-sectional view illustrating a modified example of the light-emitting portion.

An active matrix light-emitting device of this embodiment includes, over a support substrate 501, a light-emitting portion 551 (the cross section of which is illustrated in FIG. 3B and FIG. 3C as a light-emitting portion 551a and a light-emitting portion 551b, respectively), a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, a sealing substrate 505, and the sealing material 507.

Any of a separate coloring method, a color filter method, and a color conversion method can be applied to the light-emitting device of one embodiment of the present invention. The light-emitting portion 551a fabricated by a color filter method is illustrated in FIG. 3B, and the light-emitting portion 551b fabricated by a separate coloring method is illustrated in FIG. 3C.

Each of the light-emitting portion 551a and the light-emitting portion 551b includes a plurality of light-emitting units each including a switching transistor 541a, a current control transistor 541b, and a second electrode 525 electrically connected to a wiring (a source electrode or a drain electrode) of the current control transistor 541b.

A light-emitting element 503 included in the light-emitting portion 551a has a bottom-emission structure and includes a first electrode 521 which transmits visible light, an EL layer 523, and the second electrode 525. Furthermore, a partition 519 is formed so as to cover an end portion of the first electrode 521.

A light-emitting element 504 included in the light-emitting portion 551b has a top-emission structure and includes a first electrode 561, an EL layer 563, and the second electrode 565 which transmits visible light. Furthermore, the partition 519 is formed so as to cover an end portion of the first electrode 561. In the EL layer 563, at least layers (e.g., light-emitting layers) which contain different materials depending on the light-emitting element are colored separately.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal.

The driver circuit portions 552 and 553 include a plurality of transistors. FIG. 3B illustrates two of the transistors in the driver circuit portion 552 (transistors 542 and 543).

To prevent an increase in the number of manufacturing steps, the lead wiring 517 is preferably formed using the same material and the same step(s) as those of the electrode or the wiring in the light-emitting portion or the driver circuit portion. Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 3B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. As examples of the inorganic insulating film, oxide films of metals and semiconductors, nitride films of metals and semiconductors, and oxynitride films of metals and semiconductors are given, and specifically, a silicon oxide film, a silicon nitride film, a silicon oxynitride film, a silicon nitride oxide film, an aluminum oxide film, a titanium oxide film, and the like can be given.

The first insulating layer 511 has an effect of preventing diffusion of impurities into a semiconductor included in the transistor. As the second insulating layer 513, an insulating film having a planarization function is preferably selected in order to reduce surface unevenness due to the transistor.

There is no particular limitation on the structure and materials of the transistor used in the light-emitting device of one embodiment of the present invention. A top-gate transistor may be used, or a bottom-gate transistor such as an inverted staggered transistor may be used. The transistor may be a channel-etched transistor or a channel-protective transistor. An n-channel transistor may be used and a p-channel transistor may also be used.

A semiconductor layer can be formed using silicon or an oxide semiconductor. It is preferable that the transistor be formed using an oxide semiconductor which is an In—Ga—Zn-based metal oxide for a semiconductor layer so as to have low off-state current because an off-state leakage current of the light-emitting element can be reduced.

The sealing substrate 505 illustrated in FIG. 3B is provided with a color filter 533 as a coloring layer at a position overlapping with the light-emitting element 503 (a light-emitting region thereof), and is also provided with a black matrix 531 at a position overlapping with the partition 519. Furthermore, an overcoat layer 535 is provided so as to cover the color filter 533 and the black matrix 531. The sealing substrate 505 illustrated in FIG. 3C is provided with a desiccant 506.

This embodiment can be combined with any other embodiment as appropriate.

(Embodiment 4)

In this embodiment, examples of electronic devices and lighting devices of embodiments of the present invention will be described with reference to FIGS. 4A to 4E and FIGS. 6A and 6B.

Electronic devices of this embodiment each include the light-emitting device of one embodiment of the present invention in a display portion. Lighting devices of this embodiment each include the light-emitting device of one embodiment of the present invention in a light-emitting portion (a lighting portion). Highly reliable electronic devices and highly reliable lighting devices can be provided by adopting the light-emitting device of one embodiment of the present invention.

Note that one embodiment of the present invention is not limited to these examples, and the light-emitting device of one embodiment of the present invention is not necessarily included.

Examples of electronic devices to which the light-emitting device is applied are television devices (also referred to as TV or television receivers), monitors for computers and the like, cameras such as digital cameras and digital video cameras, digital photo frames, cellular phones (also referred to as mobile phones or portable telephone devices), portable game machines, portable information terminals, audio playback devices, large game machines such as pin-ball machines, and the like. Specific examples of these electronic devices and lighting devices are illustrated in FIGS. 4A to 4E and FIGS. 6A and 6B.

The electronic device and lighting device of embodiments of the present invention may have flexibility. The electronic device and lighting device can be incorporated along a curved inside/outside wall surface of a house or a building or a curved interior/exterior surface of a car.

Figure 4A:
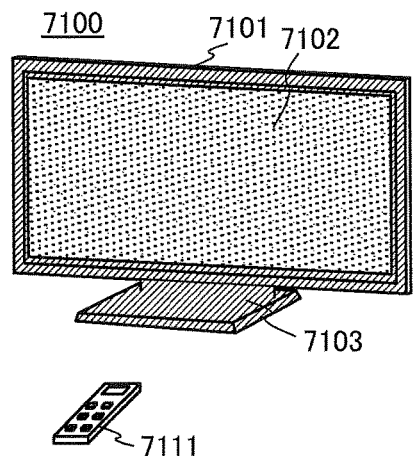
FIGS. 4A to 4E illustrate examples of an electronic device.

FIG. 4A illustrates an example of a television device. In a television device 7100, a display portion 7102 is incorporated in a housing 7101. The display portion 7102 is capable of displaying images. The light-emitting device of one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) data communication can be performed.

Figure 4B:
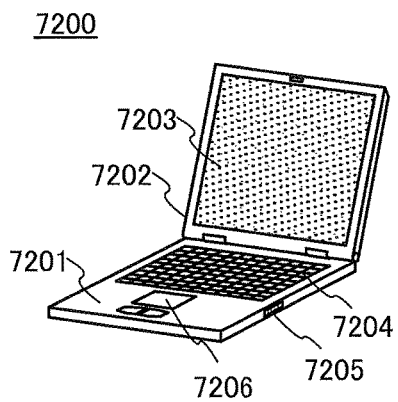

FIG. 4B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

Figure 4C:
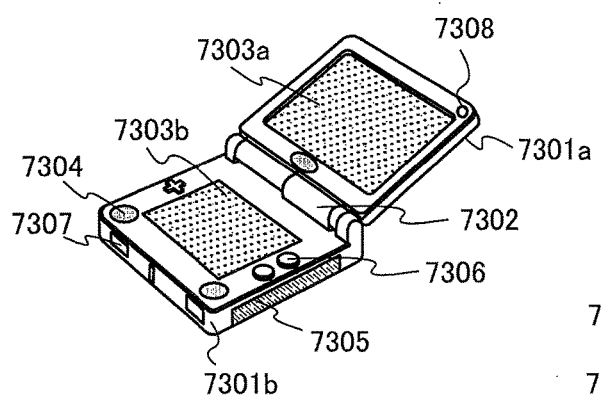

FIG. 4C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 4C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303a or the display portion 7303b, or both, and may include other accessories as appropriate. The portable game machine illustrated in FIG. 4C has a function of reading out a program or data stored in a recoding medium to display it on the display portion, and a function of sharing data with another portable game machine by wireless communication. Note that functions of the portable game machine illustrated in FIG. 4C are not limited to them, and the portable game machine can have various functions.

Figure 4D:
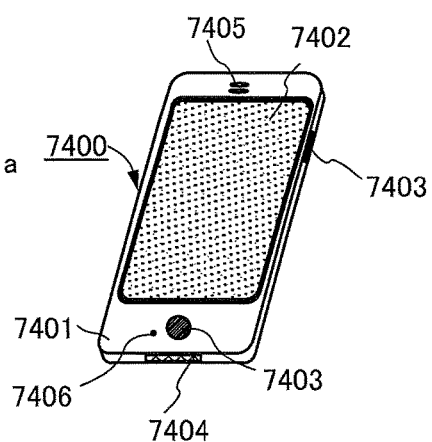

FIG. 4D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is manufactured by using the light-emitting device of one embodiment of the present invention for the display portion 7402.

When the display portion 7402 of the cellular phone 7400 illustrated in FIG. 4D is touched with a finger or the like, data can be input into the cellular phone. Furthermore, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a text input mode mainly for inputting text is selected for the display portion 7402 so that text displayed on the screen can be input.

When a sensing device including a sensor such as a gyroscope sensor or an acceleration sensor for detecting inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, a signal detected by an optical sensor in the display portion 7402 can be detected, whereby the screen mode may be controlled so as to be switched from the input mode to the display mode in the case where input by touching the display portion 7402 is not performed for a specified period.

The display portion 7402 may function as an image sensor. For example, an image of a palm print, a fingerprint, or the like is taken by touch on the display portion 7402 with the palm or the finger, whereby personal authentication can be performed. Furthermore, when a backlight or a sensing light source which emits near-infrared light is provided in the display portion, an image of a finger vein, a palm vein, or the like can be taken.

Figure 4E:
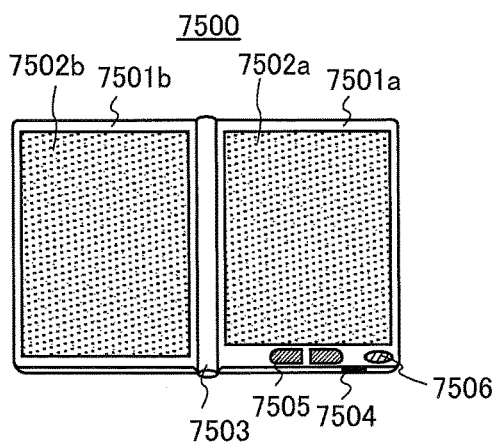

FIG. 4E illustrates an example of a foldable tablet terminal (in an open state). A tablet terminal 7500 includes a housing 7501a, a housing 7501b, a display portion 7502a, and a display portion 7502b. The housing 7501a and the housing 7501b are connected by a hinge 7503 and can be opened and closed using the hinge 7503 as an axis. The housing 7501a includes a power switch 7504, operation keys 7505, a speaker 7506, and the like. Note that the tablet terminal 7500 is manufactured by using the light-emitting device of one embodiment of the present invention for either the display portion 7502a or the display portion 7502b, or both.

Part of the display portion 7502a or the display portion 7502b can be used as a touch panel region, where data can be input by touching displayed operation keys. For example, a keyboard can be displayed on the entire region of the display portion 7502a so that the display portion 7502a is used as a touch panel, and the display portion 7502b can be used as a display screen.

The electronic device of one embodiment of the present invention may include an input/output device (also referred to as a touch panel) and a secondary battery. It is preferable that the secondary battery is capable of being charged by contactless power transmission. The input/output device includes a display portion and an input portion. For the display portion, the light-emitting device of one embodiment of the present invention can be used. For the input portion, an input device including a sensor element or the like (also referred to as a touch sensor) can be used.

As examples of the secondary battery, a lithium ion secondary battery such as a lithium polymer battery (lithium ion polymer battery) using a gel electrolyte, a nickel-hydride battery, a nickel-cadmium battery, an organic radical battery, a lead-acid battery, an air secondary battery, a nickel-zinc battery, and a silver-zinc battery can be given.

The electronic device of one embodiment of the present invention may include a touch panel and an antenna. When a signal is received by the antenna, the electronic device can display an image, data, or the like on a display portion. When the electronic device includes a secondary battery, the antenna may be used for contactless power transmission.

Figure 5A:
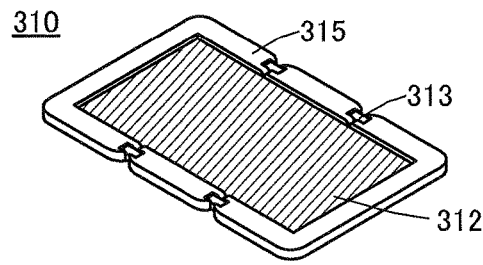
FIGS. 5A to 5I illustrate examples of an electronic device.
Figure 5B:
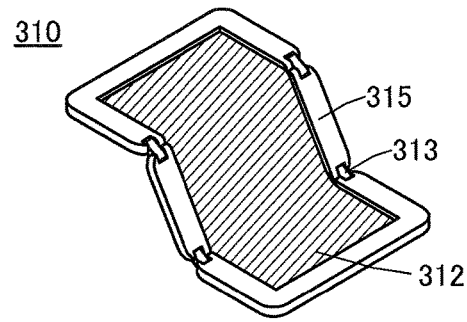
Figure 5C:
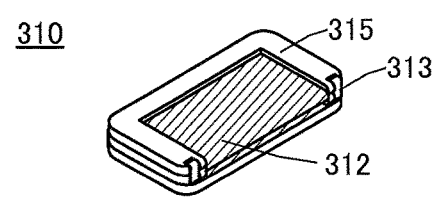

FIGS. 5A to 5C illustrate a foldable portable information terminal 310. FIG. 5A illustrates the portable information terminal 310 that is opened. FIG. 5B illustrates the portable information terminal 310 that is being opened or being folded. FIG. 5C illustrates the portable information terminal 310 that is folded. The portable information terminal 310 is highly portable when folded. When the portable information terminal 310 is opened, a seamless large display region is highly browsable.

A display panel 312 is supported by three housings 315 joined together by hinges 313. By folding the portable information terminal 310 at a connection portion between two housings 315 with the hinges 313, the portable information terminal 310 can be reversibly changed in shape from an opened state to a folded state. The light-emitting device (or display device) of one embodiment of the present invention can be used for the display panel 312. For example, a display device that can be bent with a radius of curvature of greater than or equal to 1 mm and less than or equal to 150 mm can be used.

Figure 5D:
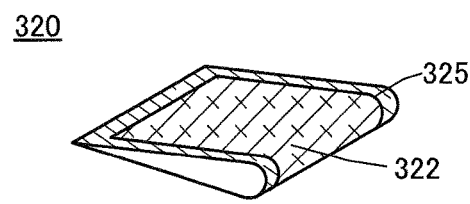
Figure 5E:
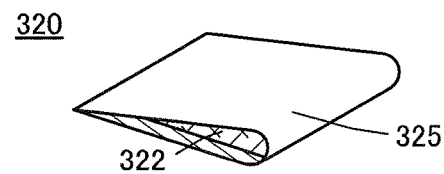

FIGS. 5D and 5E illustrate a foldable portable information terminal 320. FIG. 5D illustrates the portable information terminal 320 that is folded so that a display portion 322 is on the outside. FIG. 5E illustrates the portable information terminal 320 that is folded so that the display portion 322 is on the inside. When the portable information terminal 320 is not used, the portable information terminal 320 is folded so that a non-display portion 325 faces the outside, whereby the display portion 322 can be prevented from being contaminated or damaged. The light-emitting device (or display device) of one embodiment of the present invention can be used for the display portion 322.

Figure 5F:
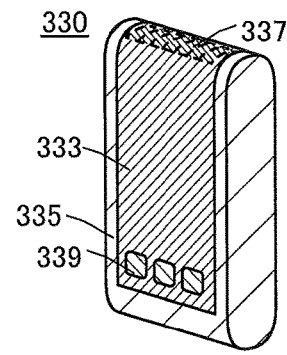
Figure 5G:
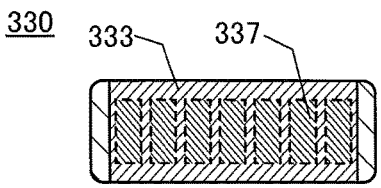
Figure 5H:
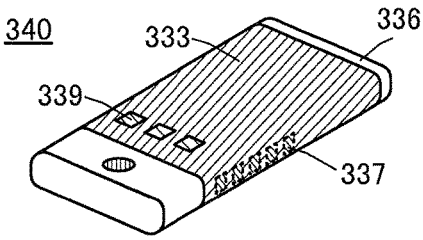

FIG. 5F is a perspective view illustrating an external shape of the portable information terminal 330. FIG. 5G is a top view of the portable information terminal 330. FIG. 5H is a perspective view illustrating an external shape of a portable information terminal 340.

The portable information terminals 330 and 340 each function as, for example, one or more of a telephone set, a notebook, and an information browsing system. Specifically, the portable information terminals 330 and 340 each can be used as a smartphone.

The portable information terminals 330 and 340 can display characters and image data on its plurality of surfaces. For example, three operation buttons 339 can be displayed on one surface (FIGS. 5F and 5H). In addition, data 337 indicated by dashed rectangles can be displayed on another surface (FIGS. 5G and 5H). Examples of the data 337 include notification from a social networking service (SNS), display indicating reception of e-mail or an incoming call, the title of e-mail or the like, the sender of e-mail or the like, the date, the time, remaining battery, and the reception strength of an antenna. Alternatively, the operation buttons 339, an icon, or the like may be displayed in place of the data 337. Although FIGS. 5F and 5G illustrate an example in which the data 337 is displayed at the top, one embodiment of the present invention is not limited thereto. The data may be displayed, for example, on the side as in the portable information terminal 340 illustrated in FIG. 5H.

The light-emitting device (or display device) of one embodiment of the present invention can be used for a display portion 333 mounted in each of a housing 335 of the portable information terminal 330 and a housing 336 of the portable information terminal 340.

Figure 5I:
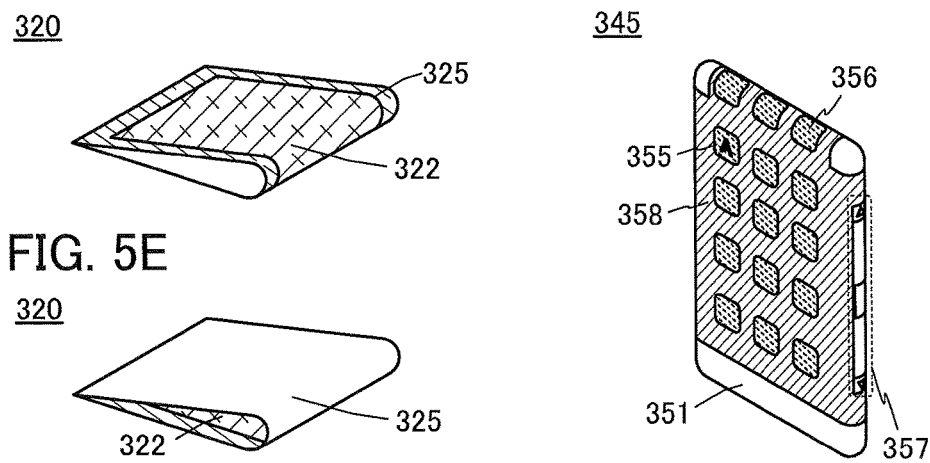

As in a portable information terminal 345 illustrated in FIG. 5I, data may be displayed on three or more surfaces. Here, data 355, data 356, and data 357 are displayed on different surfaces. The light-emitting device (or display device) of one embodiment of the present invention can be used for a display portion 358 included in a housing 351 of the portable information terminal 345.

Figure 6A:
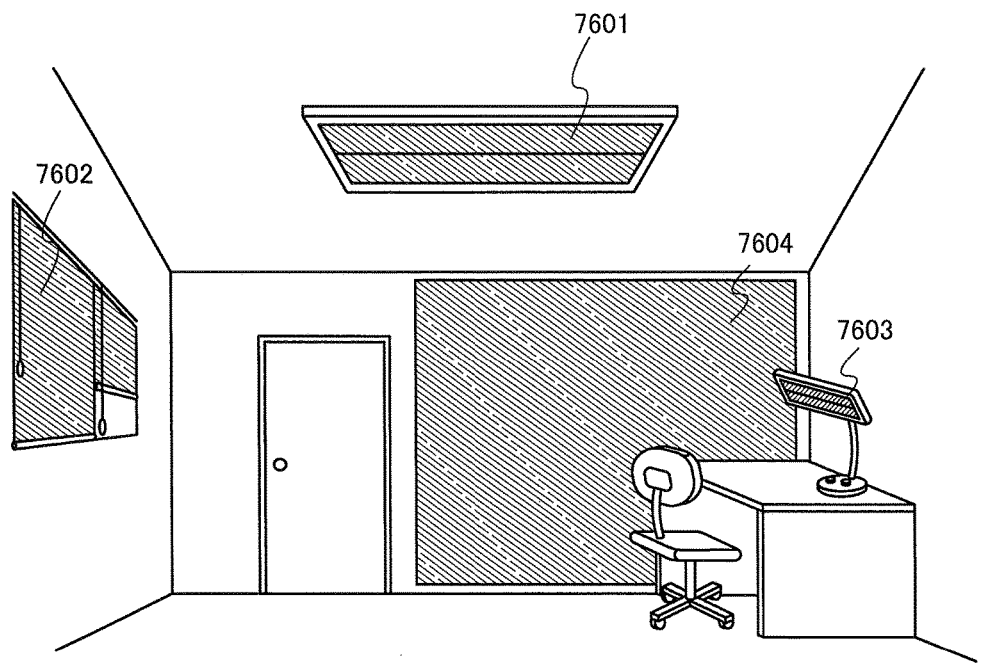
FIGS. 6A and 6B illustrate examples of a lighting device.

An indoor lighting device 7601, a roll-type lighting device 7602, a desk lamp 7603, and a planar lighting device 7604 illustrated in FIG. 6A are each an example of a lighting device which includes the light-emitting device of one embodiment of the present invention. Since the light-emitting device of one embodiment of the present invention can have a larger area, it can be used as a large-area lighting device. Furthermore, since the light-emitting device is thin, the light-emitting device can be mounted on a wall.

Figure 6B:
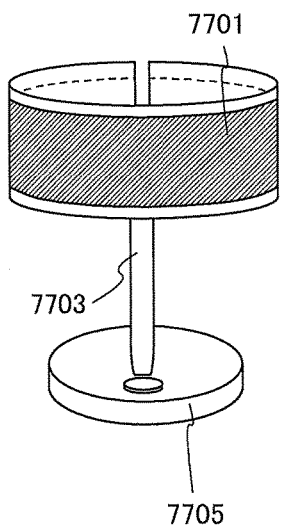

A desk lamp illustrated in FIG. 6B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. Such use of a flexible light-emitting device for a lighting device enables a place having a curved surface, such as the ceiling or dashboard of a motor vehicle, to be provided with the lighting device, as well as increases the degree of freedom in design of the lighting device. The lighting device of one embodiment of the present invention may include a housing or a cover.

This embodiment can be combined with any other embodiment as appropriate.

EXAMPLE 1

Synthesis Example 1

This example describes a method for synthesizing 2-{3-[6-(9,9-dimethylfluoren-2-yl)dibenzothiophen-4-yl]phenyl}dibenzo[f,h]quinoxalin e (abbreviation: 2mFDBtP-DBq) represented by Structural Formula (100).

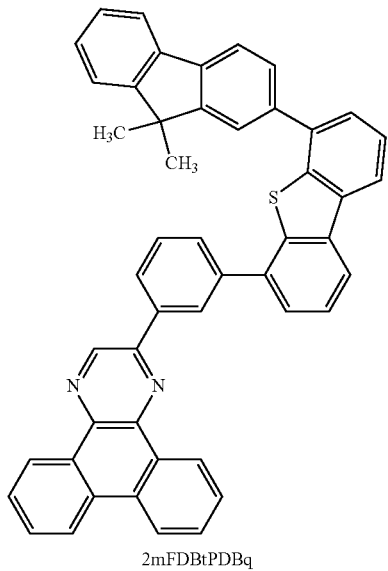

(100)

2mFDBtPDBq

First, Synthesis Scheme (B-1) is shown.

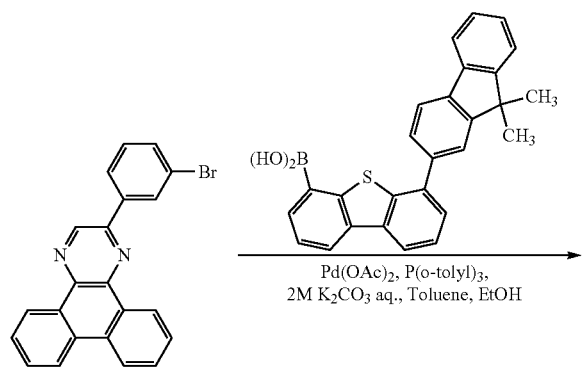

(B-1)

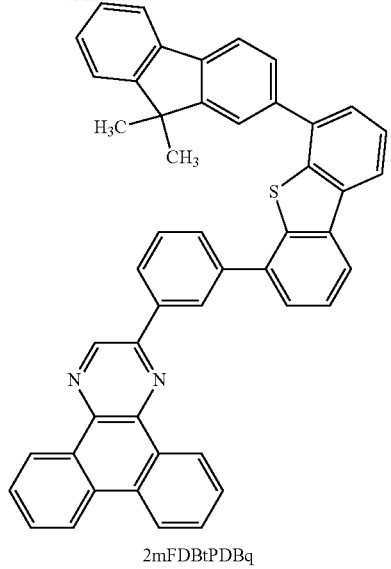

2mFDBtPDBq

Into a 200 mL three-neck flask were put 3.1 g (8.0 mmol) of 2-(3-bromophenyl)dibenzo[f,h]quinoxaline, 3.4 g (8.4 mmol) of 6-(9,9-dimethylfluoren-2-yl)dibenzothiophen-4-ylboronic acid, and 49 mg (0.16 mmol) of tri(ortho-tolyl)phosphine, and the air in the flask was replaced with nitrogen. To this mixture, 30 mL of toluene, 10 mL of ethanol, and 8.0 mL of an aqueous solution of potassium carbonate (2.0 mol/L) were added. This mixture was degassed by being stirred while the pressure was reduced. To this mixture was added 18 mg (0.080 mmol) of palladium(II) acetate, and the resulting mixture was stirred at 80° C. under a nitrogen stream for 6 hours. After the stirring, the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the resulting filtrate was purified by silica gel column chromatography (a developing solvent of hexane:toluene=3:1) to give a pale yellow oily substance. The obtained oily substance was recrystallized with a mixed solvent of toluene and hexane, so that 3.8 g of a white solid of a target substance was obtained in a yield of 71%.

By a train sublimation method, 3.8 g of the obtained white solid was purified. In the sublimation purification, the white solid was heated at 335° C. under a pressure of 10 Pa with a flow rate of an argon gas of 5.0 mL/min. After the sublimation purification, 2.1 g of a pale yellow glassy solid of a target substance was obtained at a collection rate of 55%.

This compound was identified as 2mFDBtPDBq, which was the target substance, by nuclear magnetic resonance (NMR) spectroscopy.

$^1$H NMR data of the obtained substance are as follows:
$^1$H NMR (DMSO-$d_6$, 500 MHz): δ=1.27 (s, 6H), 7.24-7.30 (m, 2H), 7.36 (dd, $J_1$=6.5 Hz, $J_2$=1.0 Hz, 1H), 7.66-7.95 (m, 15H), 8.50 (dd, $J_1$=8.0 Hz, $J_1$=1.5 Hz, 1H), 8.53 (dd, $J_1$=7.5 Hz, $J_1$=1.0 Hz, 1H), 8.82 (d, $J_1$=8.5 Hz, 1H), 8.85 (d, $J_1$=8.0 Hz, 1H), 8.90 (st, $J_1$=2.0 Hz, 1H), 9.13 (dd, $J_1$=8.0 Hz, $J_1$=1.0 Hz, 1H), 9.25 (dd, $J_1$=8.0 Hz, $J_2$=1.0 Hz, 1H), 9.73 (s, 1H).

Figure 7A:
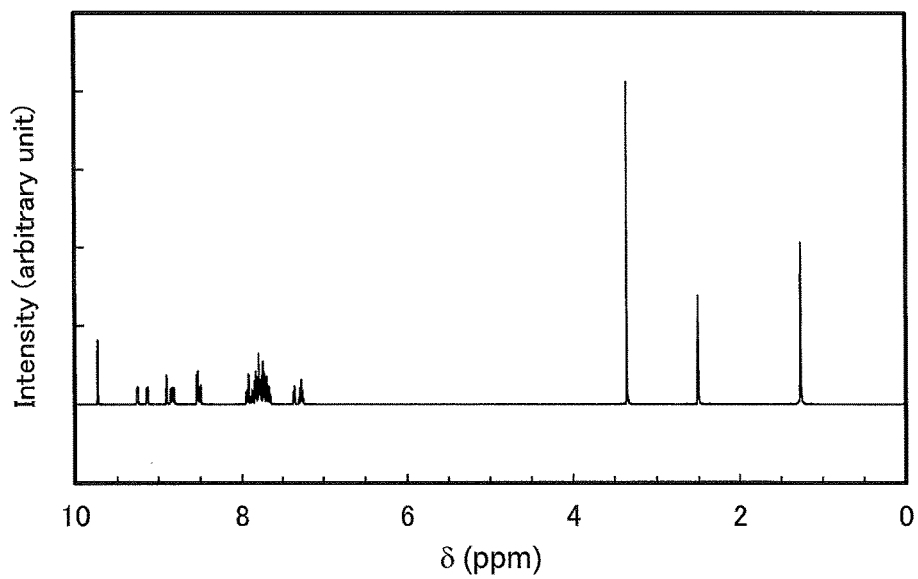
FIGS. 7A and 7B show $^1$H NMR charts of 2-{3-[6-(9,9-dimethylfluoren-2-yl)dibenzothiophen-4-yl]phenyl}dibenzo[f,h]quinoxaline (abbreviation: 2mFDBtP-DBq).
Figure 7B:
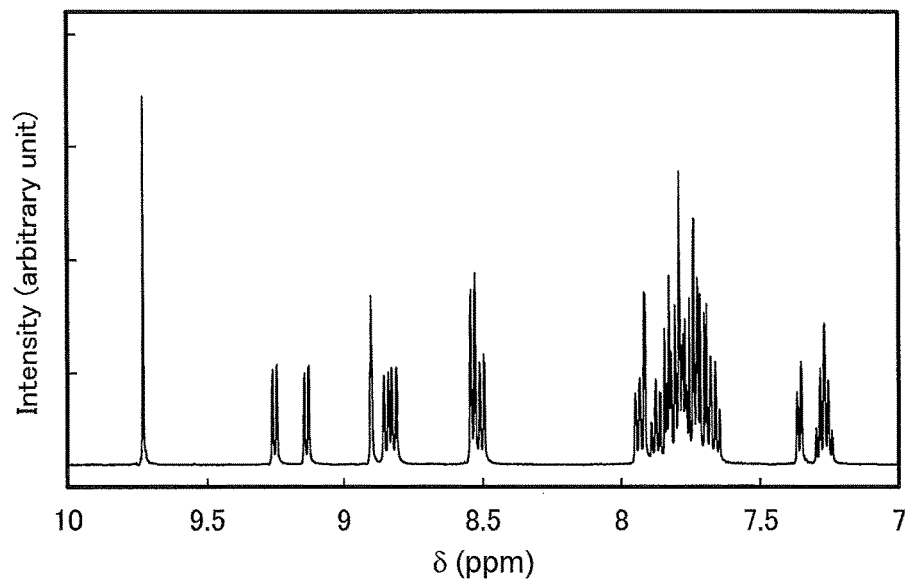

In addition, FIGS. 7A and 7B show $^1$H NMR charts. Note that FIG. 7B is a chart showing an enlarged part of FIG. 7A in the range of 7.00 ppm to 10.0 ppm. The charts reveal that 2mFDBtPDBq, which is a compound of one embodiment of the present invention represented by Structural Formula (100), was obtained.

Furthermore, 2mFDBtPDBq was analyzed by liquid chromatography mass spectrometry (LC/NIS).

The analysis by LC/MS was carried out with Acquity UPLC (manufactured by Waters Corporation), and Xevo G2 Tof MS (manufactured by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above conditions was collided with an argon gas in a collision cell to dissociate into product ions. Energy (collision energy) for the collision with argon was 70 eV. A mass range for the measurement was m/z=100-1200.

Figure 8:
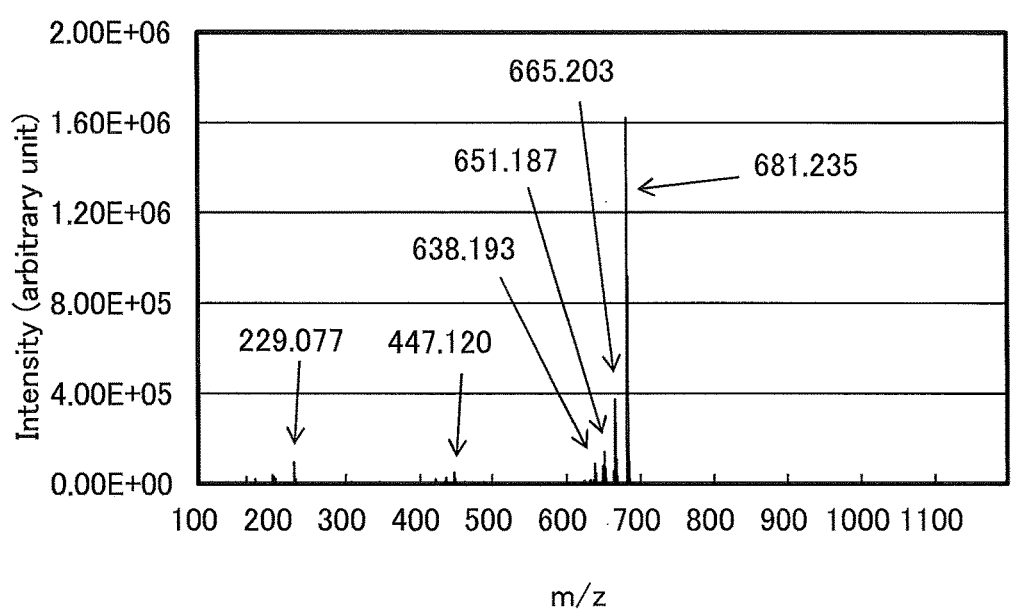
FIG. 8 shows results of LC/MS analysis of 2mFDBtP-DBq.

The measurement results are shown in FIG. 8. The results in FIG. 8 demonstrate that product ions of 2mFDBtPDBq, which is a compound of one embodiment of the present invention represented by Structural Formula (100), are detected mainly around m/z=681, m/z=665, m/z=651, m/z=638, m/z=447, and m/z=229. Note that the results in FIG. 8 show characteristics derived from 2mFDBtPDBq and thus can be regarded as important data for identifying 2mFDBtPDBq contained in a mixture.

When a C—C bond between a dibenzo[f,h]quinoxaline ring and a phenylene group is cut, electric charge remains on the dibenzo[f,h]quinoxaline ring side. The product ion detected around m/z=229 is useful data suggesting a state where the C—C bond between the dibenzo[f,h]quinoxaline ring and the phenylene group of the compound represented by Structural Formula (100) is cut. The product ions around m/z=651 and m/z=665 are respectively presumed to be a product ion formed by dissociation of two methyl groups from a dimethylfluorene ring and a product ion formed by dissociation of one methyl group from a dimethylfluorene ring. Thus, the measurement results suggest that 2mFDBtPDBq, which is a compound of one embodiment of the present invention, includes a dibenzoquinoxaline ring and a dimethylfluorene ring.

Thermogravimetry-differential thermal analysis (TG-DTA) was performed on 2mFDBtPDBq. The measurement was conducted by using a high vacuum differential type differential thermal balance (TG/DTA 2410SA, manufactured by Bruker AXS K.K.). The measurement was conducted under a nitrogen stream (flow rate: 200 mL/min) at normal pressure at a temperature rising rate of 10° C./min. It was found from the relationship between weight and temperature (thermogravimetry) that the 5% weight loss temperature of 2mFDBtPDBq was 495° C. This indicates that 2mFDBtPDBq has high heat resistance.

Figure 9A:
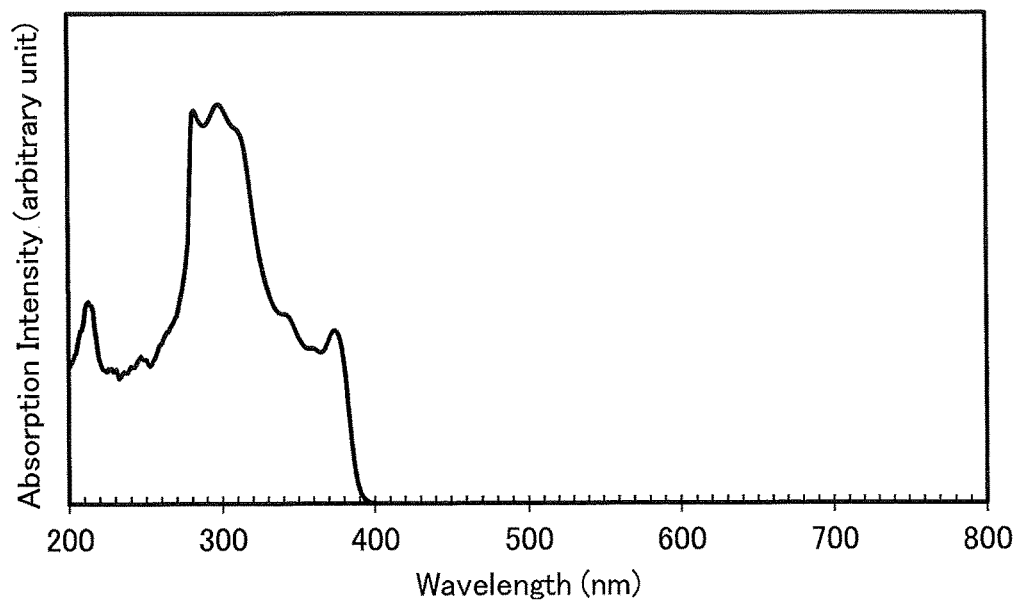
FIGS. 9A and 9B show an absorption spectrum and an emission spectrum of a toluene solution of 2mFDBtPDBq.
Figure 9B:
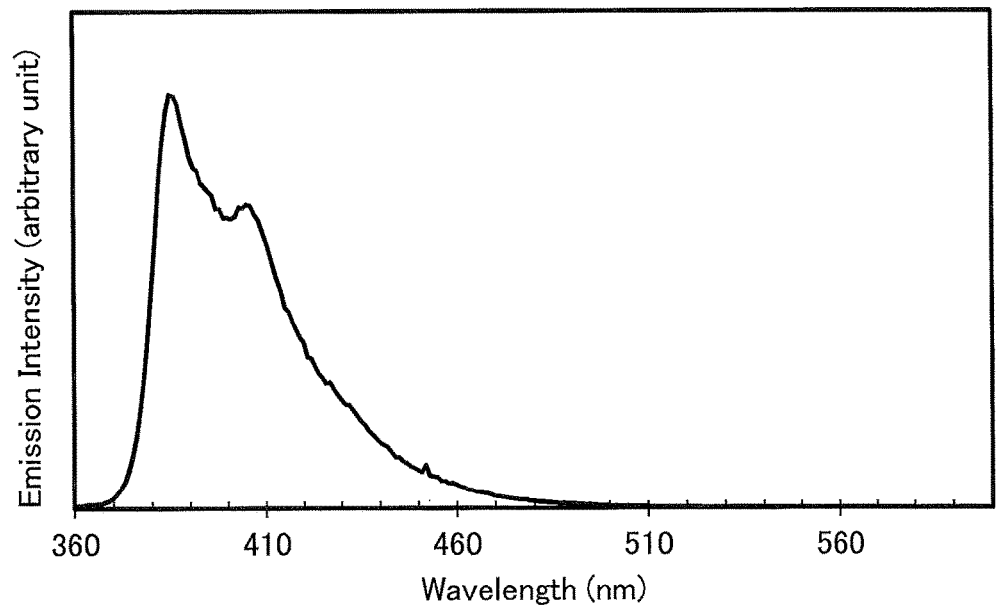
Figure 10A:
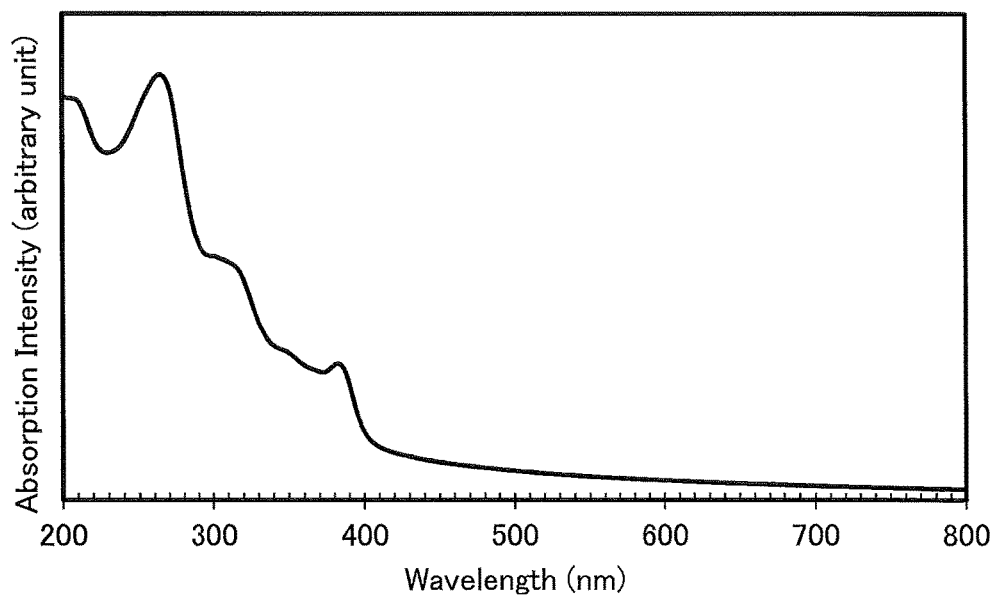
FIGS. 10A and 10B show an absorption spectrum and an emission spectrum of a thin film of 2mFDBtPDBq.
Figure 10B:
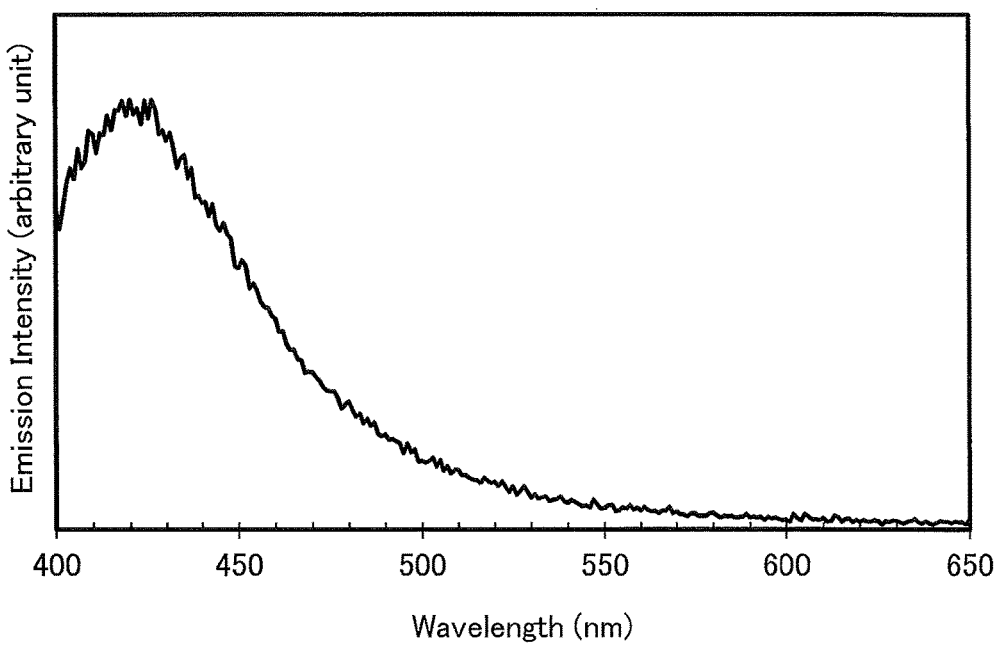

FIG. 9A shows an ultraviolet-visible absorption spectrum (hereinafter, simply referred to as "absorption spectrum") of a toluene solution of 2mFDBtPDBq and FIG. 9B shows an emission spectrum thereof. FIG. 10A shows an absorption spectrum of a thin film of 2mFDBtPDBq and FIG. 10B shows an emission spectrum thereof. The thin film was formed over a quartz substrate by a vacuum evaporation method. The absorption spectra were measured with an ultraviolet-visible light spectrophotometer (V550 type manufactured by JASCO Corporation). The emission spectra were measured with a fluorescence spectrophotometer (FS920 manufactured by Hamamatsu Photonics K.K.). In each of the graphs showing the absorption spectra and emission spectra, the horizontal axis indicates wavelength (nm) and the vertical axis indicates absorption intensity or emission intensity (arbitrary unit). According to FIGS. 9A and 9B, the absorption peaks of the toluene solution of 2mFDBtPDBq are observed around 282 nm, 298 nm, 342 nm, 360 nm, and 375 nm, and the emission wavelength peaks are observed at 385 nm and 405 nm (excitation wavelength: 344 nm). According to FIGS. 10A and 10B, the absorption peaks of the thin film of 2mFDBtPDBq are observed around 208 nm, 264 nm, 301 nm, 315 nm, 347 nm, 366 nm, and 383 nm, and the emission wavelength peak is observed at 420 nm (excitation wavelength: 350 nm).

The ionization potential of 2mFDBtPDBq in a thin film state was measured by a photoelectron spectrometer (AC-3, manufactured by Riken Keiki, Co., Ltd.) in the air. The obtained value of the ionization potential was converted into a negative value, so that the HOMO level of 2mFDBtPDBq was −6.25 eV. From the data of the absorption spectrum of the thin film in FIG. 10A, the absorption edge of 2mFDBtPDBq, which was obtained from Tauc plot with an assumption of direct transition, was 3.09 eV. Thus, the optical energy gap of 2mFDBtPDBq in the solid state was estimated at 3.09 eV; from the values of the HOMO level obtained above and this energy gap, the LUMO level of 2mFDBtPDBq can be estimated at −3.16 eV. This reveals that 2mFDBtPDBq in the solid state has an energy gap as wide as 3.09 eV.

Another example of a method for synthesizing 2mFDBtPDBq is described.

Step 1: Synthesis of 6-Iodo-4-(9,9-dimethylfluoren-2-yl)dibenzothiophene

A synthesis scheme of Step 1 is shown in (C-1).

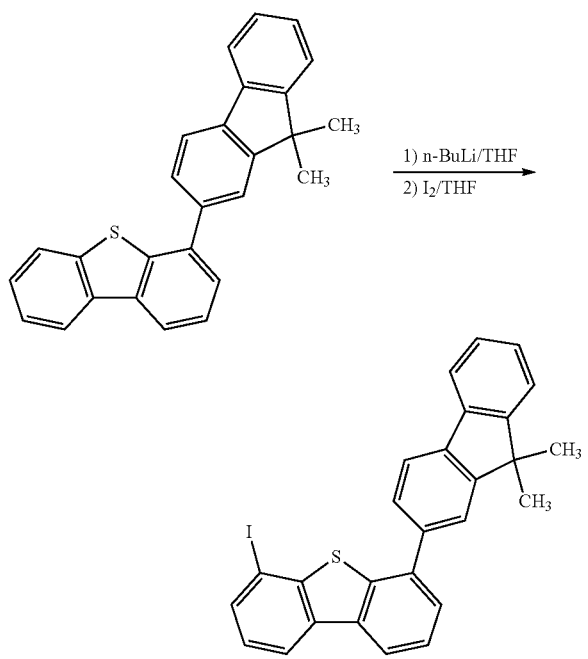

(C-1)

Into a 200 mL three-neck flask was put 4.0 g (10 mmol) of 4-(9,9-dimethylfluoren-2-yl)dibenzothiophene, and the air in the flask was replaced with nitrogen. To this flask was added 30 mL of tetrahydrofuran (THF), and this solution was cooled down to −80° C. Then, 7.5 mL (12 mmol) of n-butyllithium (a 1.6 mol/L hexane solution) was dripped into this solution with a syringe. After the dripping, this solution was stirred for 2 hours while its temperature was returned to room temperature. After the stirring, this solution was again cooled to −80° C., and 0.90 mL (8.0 mmol) of trimethyl borate was added to this solution, followed by stirring for 2 hours while its temperature was returned to room temperature. Then, a solution in which 3.6 g (14 mmol) of iodine had been dissolved in 20 mL of THF was dripped into this solution with a dripping funnel, and the mixture was stirred for 18 hours while its temperature was returned to room temperature. After the stirring, 100 mL of an aqueous solution of sodium thiosulfate was added to the resulting solution, and the mixture was stirred for 2 hours. After the stirring, the aqueous layer of the mixture was subjected to extraction with ethyl acetate, and the solution of the extract and the organic layer were combined and washed with an aqueous solution of sodium thiosulfate and saturated brine. The organic layer was dried with magnesium sulfate, and this mixture was gravity-filtered. The obtained filtrate was concentrated to give a brown oily substance. Approximately 40 mL of hexane was added to this oily substance and irradiation with ultrasonic waves was performed, so that a pale brown solid was precipitated. The precipitated solid was collected by suction filtration to give 2.4 g of a white powder of a target substance in a yield of 45%.

Step 2: Synthesis of 2mFDBtPDBq

A synthesis scheme of Step 2 is shown in (C-2).

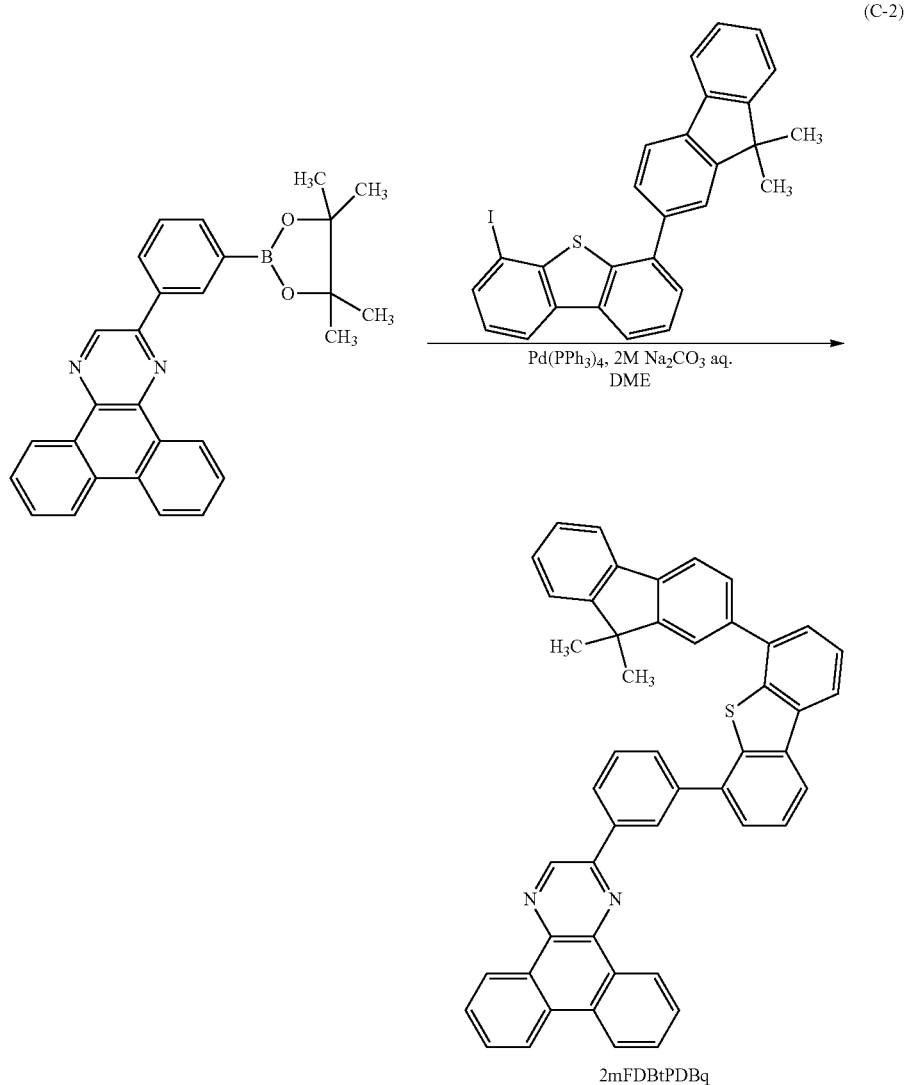

(C-2)

2mFDBtPDBq

Into a 200 mL three-neck flask were put 1.2 g (2.8 mmol) of 4,4,5,5-tetramethyl-2-[3-(dibenzo[f,h]quinoxalin-2-yl)phenyl]-1,3,2-dioxaborolane and 1.4 g (2.8 mmol) of 6-iodo-4-(9,9-dimethylfluoren-2-yl)dibenzothiophene, and the air in the flask was replaced with nitrogen. To this mixture, 15 mL of ethylene glycol dimethyl ether and 3.0 mL of an aqueous solution of potassium carbonate (2.0 mol/L) were added. This mixture was degassed by being stirred while the pressure was reduced. To this mixture was added 32 mg (0.028 mmol) of tetrakis(triphenylphosphine) palladium(0), and the resulting mixture was stirred under reflux under a nitrogen stream for 40 hours. After the stirring, 30 mL of toluene and 10 mL of water were added to this mixture, and the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the resulting filtrate was purified by silica gel column chromatography (a developing solvent of hexane:toluene=3:1) to give a pale brown oily substance. Ethyl acetate and hexane were added to the oily substance and irradiation with ultrasonic waves was performed, whereby a pale brown solid was precipitated. The precipitated solid was collected by suction filtration to give 1.2 g of a pale brown solid of a target substance in a yield of 61%.

By a train sublimation method, 1.1 g of the obtained pale yellow solid was purified. In the sublimation purification, the pale yellow solid was heated at 310° C. under a pressure of 10 Pa with a flow rate of an argon gas of 5.0 mL/min. After the sublimation purification, 0.95 g of a pale yellow glassy solid of a target substance was obtained at a collection rate of 79%.

EXAMPLE 2

Synthesis Example 2

This example describes a method for synthesizing 2-(3-{3-[6-(9,9-dimethylfluoren-2-yl)dibenzothiophen-4-yl]phenyl}phenyl)dibenzo[f,h]quinoxaline (abbreviation: 2mDBtBPDBq-VIII) represented by Structural Formula (112).

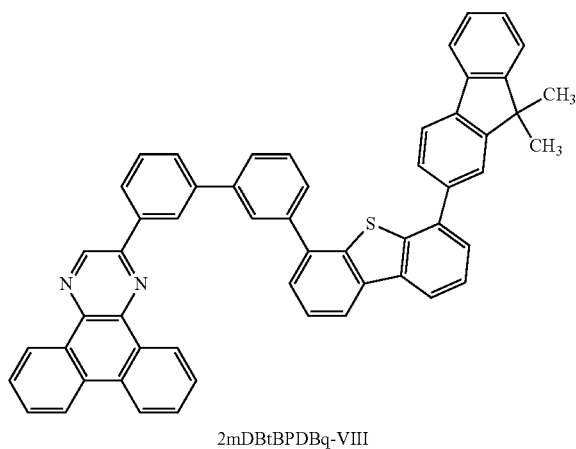

(112)

2mDBtBPDBq-VIII

Step 1: Synthesis of 4-(9,9-Dimethylfluoren-2-yl)dibenzothiophene

A synthesis scheme of Step 1 is shown in (D-1).

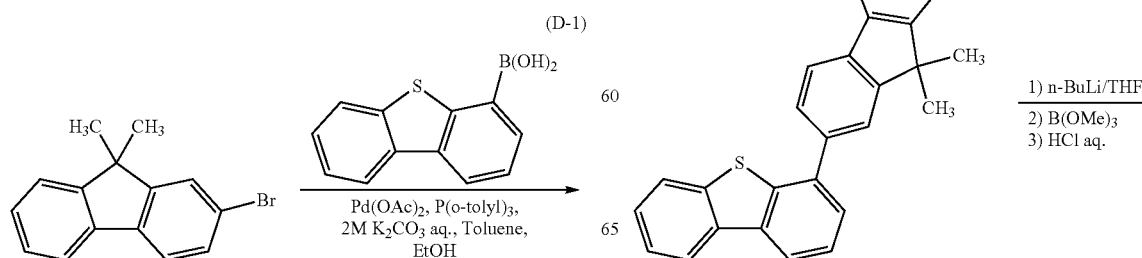

(D-1)

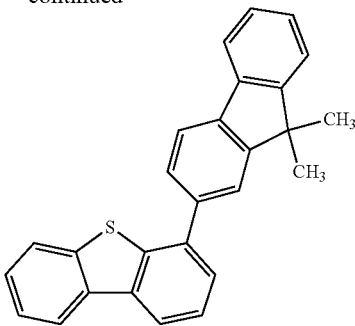

Into a 300 mL three-neck flask were put 5.0 g (18 mmol) of 2-bromo-9,9-dimethylfluorene, 4.2 g (18 mmol) of dibenzothiophen-4-ylboronic acid, and 0.11 g (0.36 mmol) of tri(ortho-tolyl)phosphine, and the air in the flask was replaced with nitrogen. To this mixture, 65 mL of toluene, 25 mL of ethanol, and 18 mL of an aqueous solution of potassium carbonate (2.0 mol/L) were added. This mixture was degassed by being stirred while the pressure was reduced. To this mixture was added 40 mg (0.18 mmol) of palladium(II) acetate, and the resulting mixture was stirred at 80° C. under a nitrogen stream for 3 hours. After the stirring, the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the resulting filtrate was dissolved in approximately 10 mL of toluene, and the resulting solution was purified by silica gel column chromatography (developing solvent: hexane) to give an oily substance. The obtained oily substance was recrystallized with hexane, so that 5.7 g of a white solid of a target substance was obtained in a yield of 84%.

Step 2: Synthesis of 6-(9,9-Dimethylfluoren-2-yl)dibenzothiophen-4-ylboronic acid A synthesis scheme of Step 2 is shown in (D-2).

(D-2)

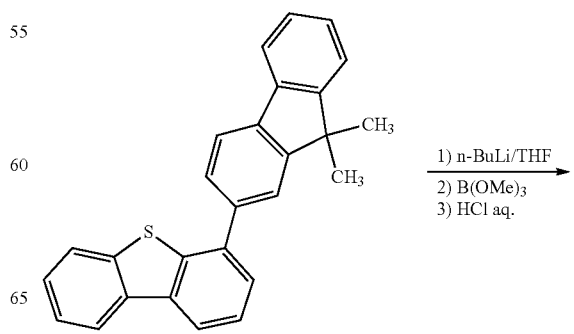

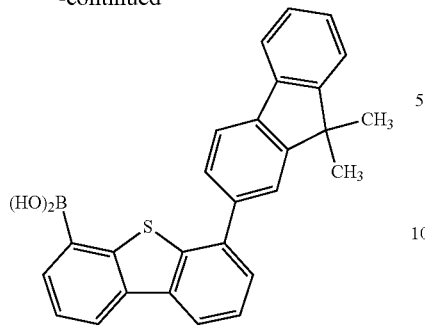

Into a 100 mL three-neck flask was put 2.7 g (7.1 mmol) of 4-(9,9-dimethylfluoren-2-yl)dibenzothiophene, and the air in the flask was replaced with nitrogen. To this flask was added 36 mL of tetrahydrofuran (THF), and this solution was cooled down to −80° C. Then, 4.9 mL (7.8 mmol) of n-butyllithium (a 1.6 mol/L hexane solution) was dripped into this solution with a syringe. After the dripping, this solution was stirred for 2 hours while its temperature was returned to room temperature. After the stirring, this solution was again cooled to −80° C., and 0.90 mL (8.0 mmol) of trimethyl borate was added to this solution, followed by stirring for 2 hours while its temperature was returned to room temperature. After the stirring, approximately 10 mL of dilute hydrochloric acid (1.0 mol/L) was added to the resulting solution, and the mixture was stirred for 1 hour. After the stirring, the aqueous layer of the mixture was subjected to extraction with ethyl acetate, and the solution of the extract and the organic layer were combined and washed with a saturated aqueous solution of sodium hydrogen carbonate and saturated brine. The organic layer was dried with magnesium sulfate, and this mixture was gravity-filtered. The obtained filtrate was concentrated to give a yellow oily substance. Approximately 5 mL of toluene and approximately 40 mL of hexane were added to this oily substance, followed by irradiation with ultrasonic waves to precipitate a white solid. The precipitated solid was collected by suction filtration, and approximately 10 mL of ethyl acetate and approximately 40 mL of hexane were added to the resulting solid; thus, 1.4 g of a white powder of a target substance was obtained in a yield of 48%.

Step 3: Synthesis of 6-(3-Bromophenyl)-4-(9,9-dimethylfluoren-2-yl)dibenzothiophene A synthesis scheme of Step 3 is shown in (D-3).

(D-3)

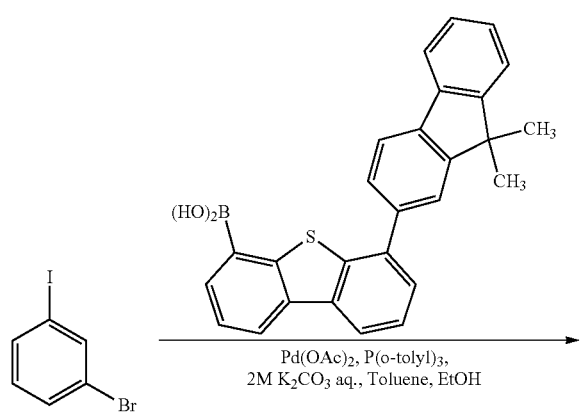

Into a 200 mL three-neck flask were put 1.0 g (3.6 mmol) of 3-bromoiodobenzene, 1.4 g (3.3 mmol) of 6-(9,9-dimethylfluoren-2-yl)dibenzothiophen-4-ylboronic acid, and 0.11 g (0.36 mmol) of tri(ortho-tolyl)phosphine, and the air in the flask was replaced with nitrogen. To this mixture, 14 mL of toluene, 4.0 mL of ethanol, and 4.0 mL of an aqueous solution of potassium carbonate (2.0 mol/L) were added. This mixture was degassed by being stirred while the pressure was reduced. To this mixture was added 40 mg (0.18 mmol) of palladium(II) acetate, and the resulting mixture was stirred at 80° C. under a nitrogen stream for 2 hours. After the stirring, the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the obtained filtrate was dissolved in approximately 10 mL of toluene. The resulting solution was filtered through Celite (Catalog No. 531-16855 produced by Wako Pure Chemical Industries, Ltd., the same applies to Celite described below and a repetitive description thereof is omitted), alumina, and Florisil (Catalog No. 540-00135 produced by Wako Pure Chemical Industries, Ltd., the same applies to Florisil described below and a repetitive description thereof is omitted) to give an oily substance. The oily substance was purified by silica gel column chromatography (a developing solvent of hexane:toluene=19:1) to give an oily substance. The oily substance was left standing for approximately 15 hours, so that a white solid was precipitated. The solid was washed with methanol and collected by suction filtration, so that 0.90 g of a white solid of a target substance was obtained in a yield of 51%.

Step 4: Synthesis of 3-[6-(9,9-Dimethylfluoren-2-yl)dibenzothiophen-4-yl]phenylboronic acid A synthesis scheme of Step 4 is shown in (D-4).

(D-4)

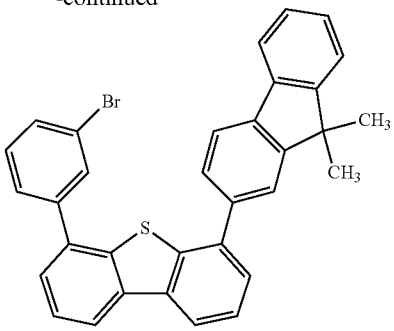

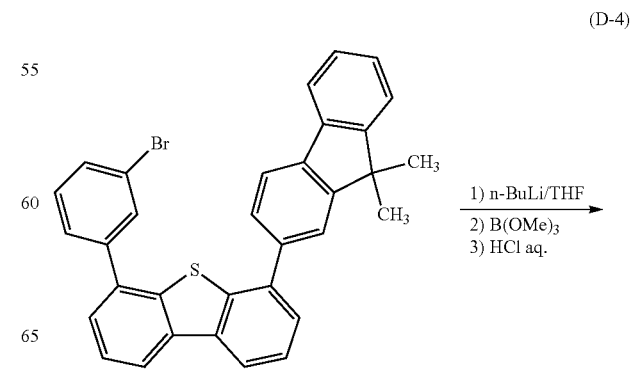

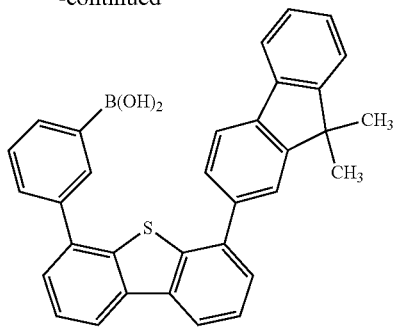

Into a 100 mL three-neck flask was put 2.4 g (4.5 mmol) of 6-(3-bromophenyl)-4-(9,9-dimethylfluoren-2-yl)dibenzothiophene, and the air in the flask was replaced with nitrogen. To this flask was added 57 mL of tetrahydrofuran (THF), and this solution was cooled down to −40° C. Then, 3.2 mL (5.0 mmol) of n-butyllithium (a 1.6 mol/L hexane solution) was dripped into this solution with a syringe. After the dripping, this solution was stirred at the same temperature for 2 hours. After the stirring, 0.67 mL (6.0 mmol) of trimethyl borate was added to this solution, followed by stirring for 22 hours while its temperature was returned to room temperature. After the stirring, approximately 10 mL of dilute hydrochloric acid (1.0 mol/L) was added to the resulting solution, and the mixture was stirred for 1 hour. After the stirring, the aqueous layer of the mixture was subjected to extraction with ethyl acetate, and the solution of the extract and the organic layer were combined and washed with a saturated aqueous solution of sodium hydrogen carbonate and saturated brine. The organic layer was dried with magnesium sulfate, and this mixture was gravity-filtered. The obtained filtrate was concentrated to give a brown oily substance. Approximately 5 mL of toluene and approximately 100 mL of hexane were added to this oily substance, followed by irradiation with ultrasonic waves to precipitate a solid. The precipitated solid was washed with hexane to give a pale brown solid. The solid was collected by suction filtration and recrystallized with a mixed solvent of ethyl acetate and hexane; thus, 1.3 g of a brown powder of a target substance was obtained in a yield of 58%.

Step 5: Synthesis of 2mDBtBPDBq-VIII

A synthesis scheme of Step 5 is shown in (D-5).

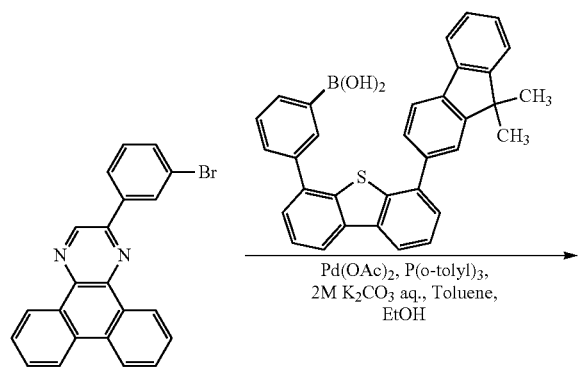

(D-5)

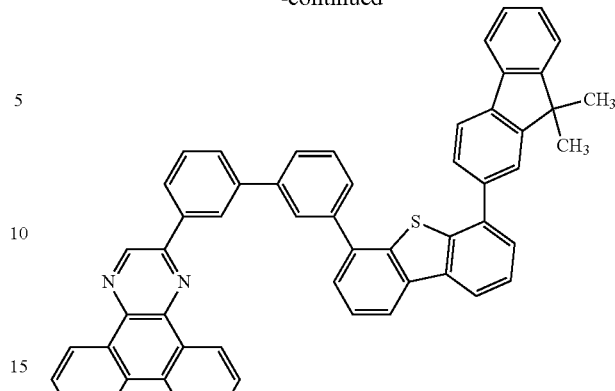

2mDBtBPDBq-VIII

Into a 200 mL three-neck flask were put 0.81 g (2.1 mmol) of 2-(3-bromophenyl)dibenzo[f,h]quinoxaline, 1.1 g (2.3 mmol) of 3-[6-(9,9-dimethylfluoren-2-yl)dibenzothiophen-4-yl]phenylboronic acid, and 0.17 g (0.55 mmol) of tri(ortho-tolyl)phosphine, and the air in the flask was replaced with nitrogen. To this mixture, 7.0 mL of toluene, 3.0 mL of ethanol, and 2.5 mL of an aqueous solution of potassium carbonate (2.0 mol/L) were added. This mixture was degassed by being stirred while the pressure was reduced. To this mixture was added 25 mg (0.11 mmol) of palladium(II) acetate, and the resulting mixture was stirred at 80° C. under a nitrogen stream for 12 hours. After the stirring, the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the resulting filtrate was purified by silica gel column chromatography (a developing solvent of hexane:toluene=9:1) to give a pale yellow solid. The obtained solid was recrystallized with ethyl acetate, so that 0.70 g of a pale yellow solid of a target substance was obtained in a yield of 44%.

By a train sublimation method, 0.70 g of the obtained pale yellow solid was purified. In the sublimation purification, the pale yellow solid was heated at 330° C. under a pressure of 10 Pa with a flow rate of an argon gas of 5.0 mL/min. After the sublimation purification, 0.56 g of a pale yellow glassy solid of a target substance was obtained at a collection rate of 80%.

This compound was identified as 2mDBtBPDBq-VIII, which was the target substance, by nuclear magnetic resonance (NMR) spectroscopy.

$^1$H NMR data of the obtained substance are as follows:
$^1$H NMR (DMSO-$d_6$, 500 MHz): δ=1.31 (s, 6H), 7.22-7.28 (m, 2H), 7.43 (dd, $J_1$=6.0 Hz, $J_2$=2.0 Hz, 1H), 7.63-7.88 (m, 15H), 7.96 (d, $J_1$=7.5 Hz, 2H), 8.28 (s, 1H), 8.47-8.52 (m, 3H), 8.78 (s, 1H), 8.86 (dd, $J_1$=8.5 Hz, $J_2$=3.5 Hz, 2H), 9.14 (dd, $J_1$=8.0 Hz, $J_2$=1.0 Hz, 1H), 9.28 (dd, $J_1$=8.0 Hz, $J_2$=1.0 Hz, 1H), 9.77 (s, 1H).

Figure 11A:
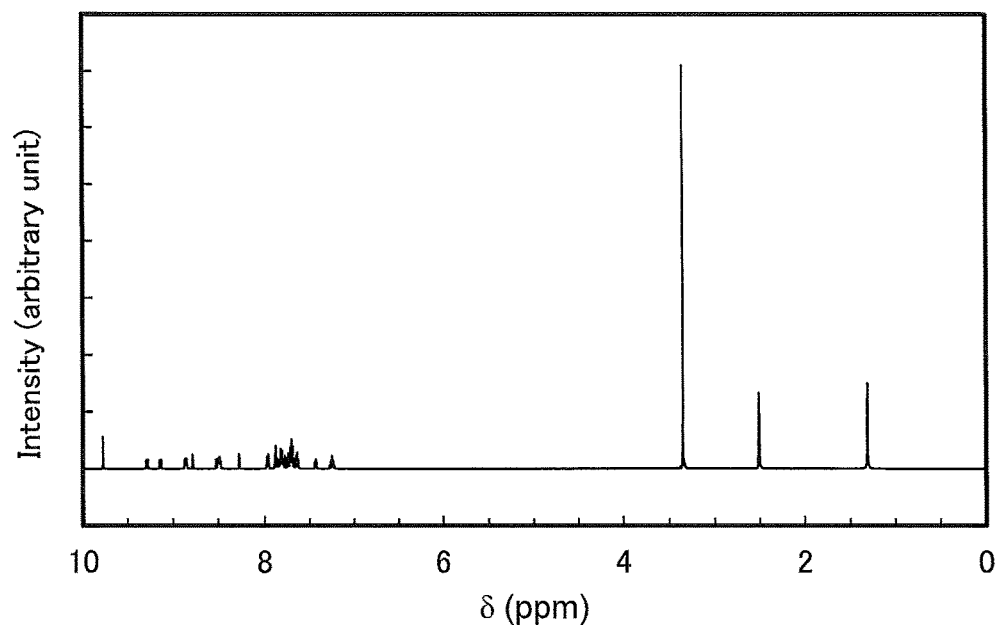
FIGS. 11A and 11B show $^1$H NMR charts of 2-(3-{3-[6-(9,9-dimethylfluoren-2-yl)dibenzothiophen-4-yl]phenyl}phenyl)dibenzo[f,h]quinoxaline (abbreviation: 2mDBtBPDBq-VIII).
Figure 11B:
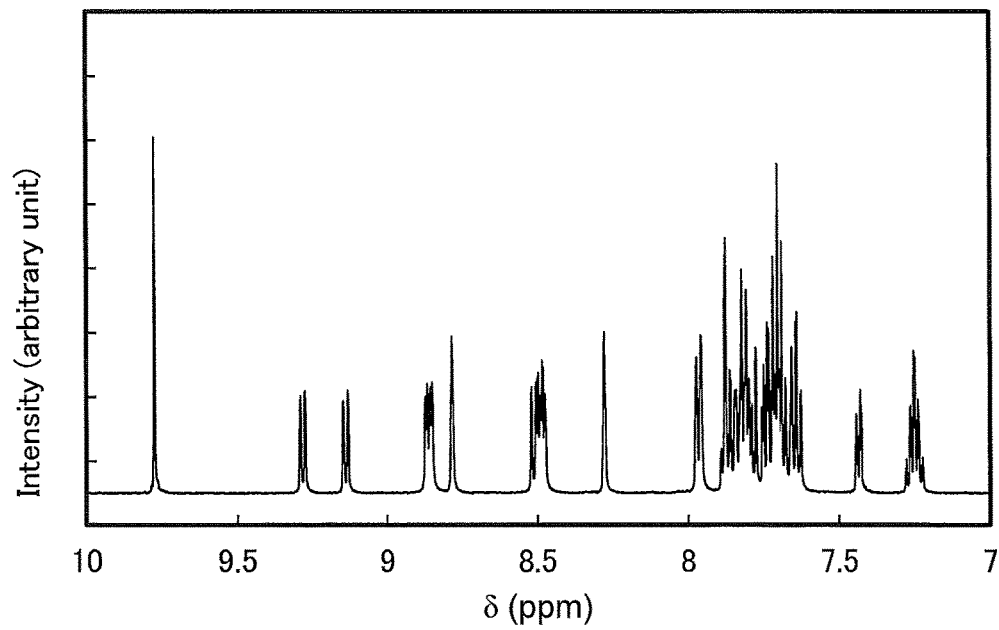

In addition, FIGS. 11A and 11B show $^1$H NMR charts. Note that FIG. 11B is a chart showing an enlarged part of FIG. 11A in the range of 7.00 ppm to 10.0 ppm. The charts reveal that 2mDBtBPDBq-VIII, which is a compound of one embodiment of the present invention represented by Structural Formula (112), was obtained.

Furthermore, 2mDBtBPDBq-VIII was analyzed by LC/MS. The conditions of the measurement were similar to those in Example 1.

Figure 12:
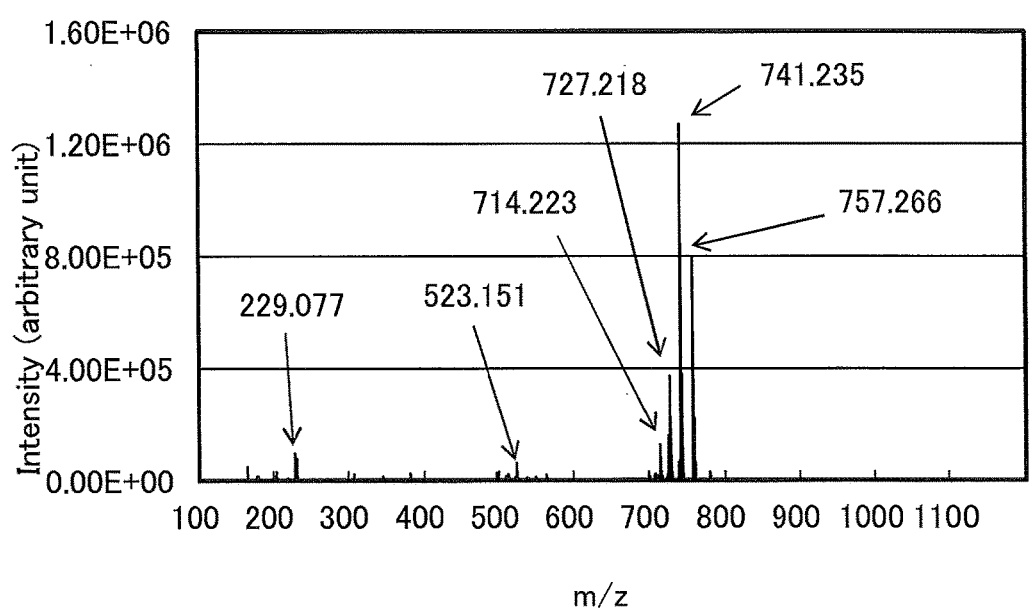
FIG. 12 shows results of LC/MS analysis of 2mDBtBP-DBq-VIII.

The measurement results are shown in FIG. 12. The results in FIG. 12 demonstrate that product ions of 2mDBt-BPDBq-VIII, which is a compound of one embodiment of the present invention represented by Structural Formula (112), are detected mainly around m/z=757, m/z=741, m/z=727, m/z=714, m/z=523, and m/z=229. Note that the results in FIG. 12 show characteristics derived from 2mDBt-BPDBq-VIII and thus can be regarded as important data for identifying 2mDBtBPDBq-VIII contained in a mixture.

When a C—C bond between a dibenzo[f,h]quinoxaline ring and a phenylene group is cut, electric charge remains on the dibenzo[f,h]quinoxaline ring side. The product ion detected around m/z=229 is useful data suggesting a state where the C—C bond between the dibenzo[f,h]quinoxaline ring and the phenylene group of the compound represented by Structural Formula (112) is cut. The product ions around m/z=727 and m/z=741 are respectively presumed to be a product ion formed by dissociation of two methyl groups from a dimethylfluorene ring and a product ion formed by dissociation of one methyl group from a dimethylfluorene ring. Thus, the measurement results suggest that 2mDBtB-PDBq-VIII, which is a compound of one embodiment of the present invention, includes a dibenzoquinoxaline ring and a dimethylfluorene ring.

TG-DTA was performed on 2mDBtBPDBq-VIII. The conditions of the measurement were similar to those in Example 1. It was found from thermogravimetry that the 5% weight loss temperature of 2mDBtBPDBq-VIII was 500° C. or higher. This indicates that 2mDBtBPDBq-VIII has high heat resistance.

Figure 13A:
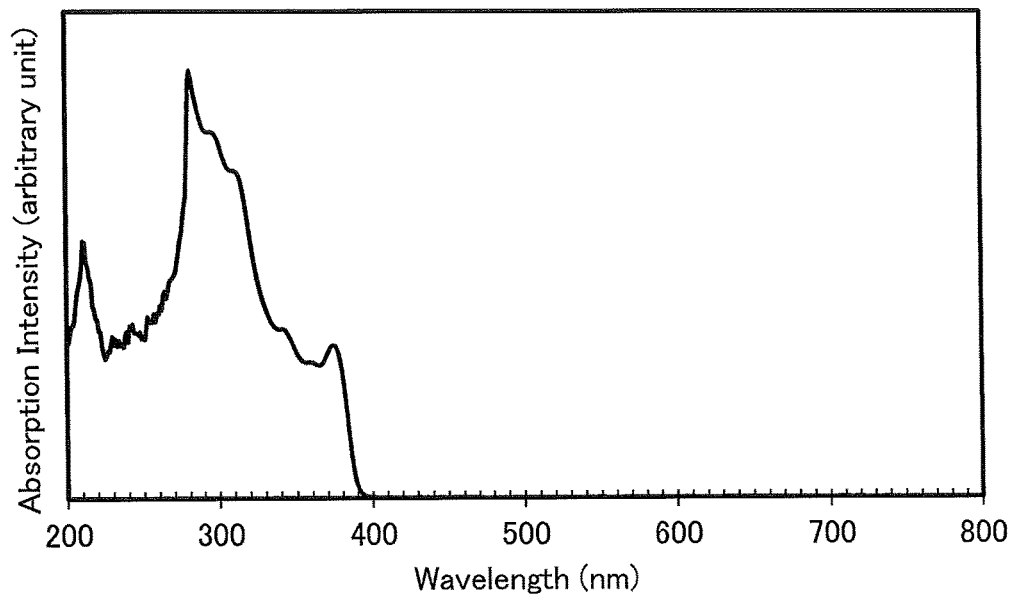
FIGS. 13A and 13B show an absorption spectrum and an emission spectrum of a toluene solution of 2mDBtBPDBq-VIII.
Figure 13B:
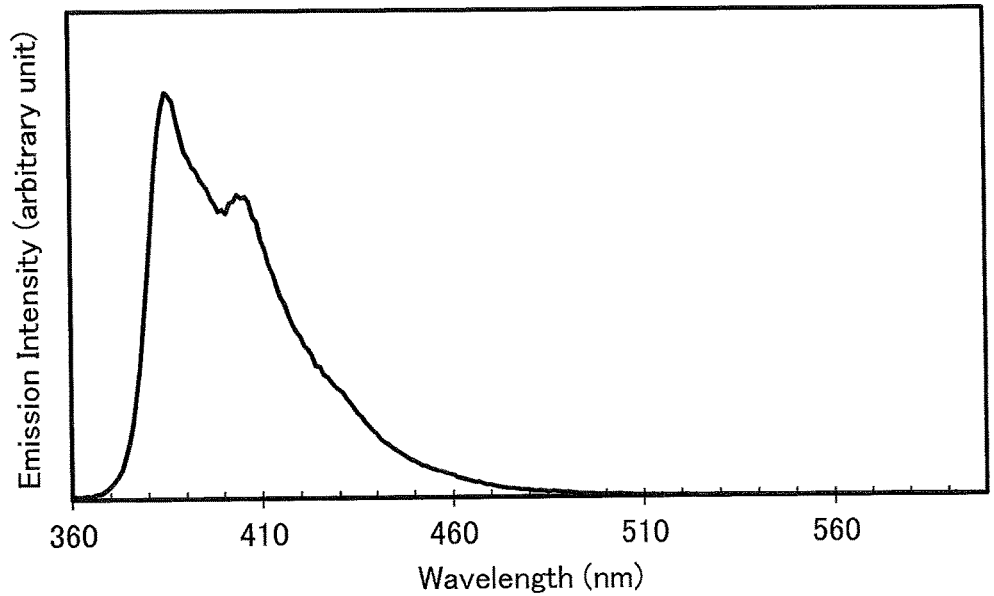
Figure 14A:
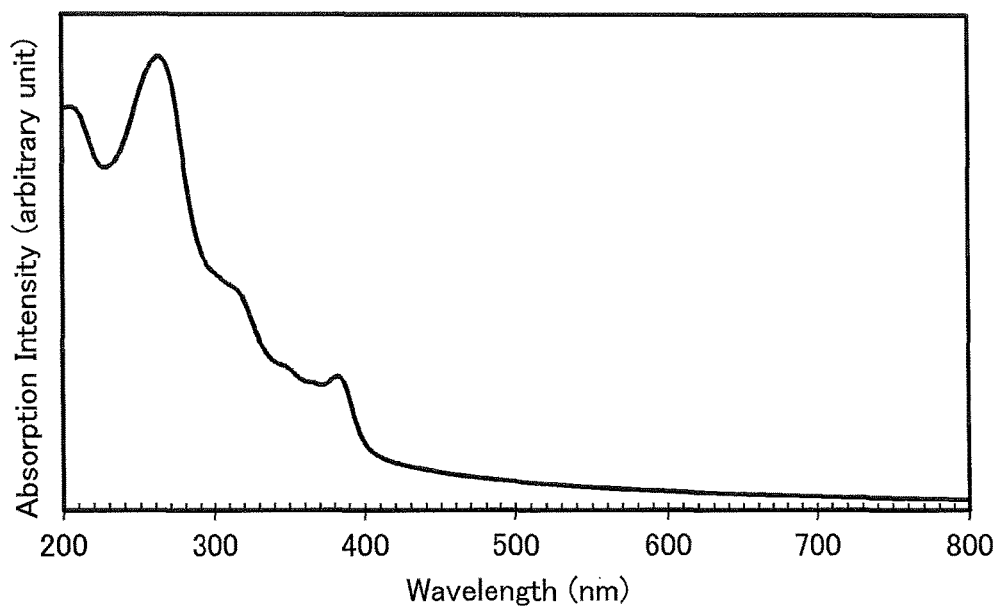
FIGS. 14A and 14B show an absorption spectrum and an emission spectrum of a thin film of 2mDBtBPDBq-VIII.
Figure 14B:
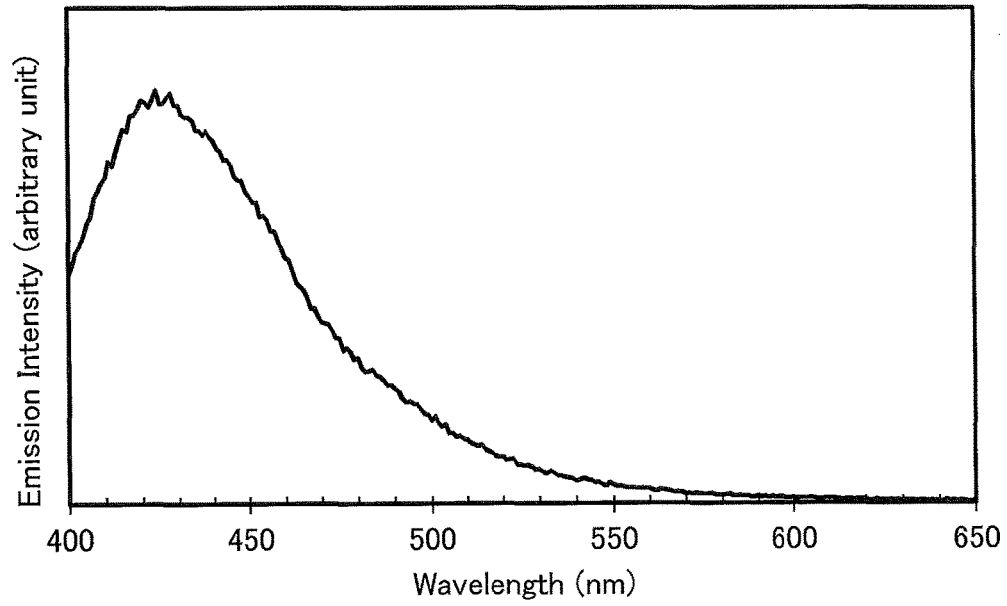

FIG. 13A shows an absorption spectrum of a toluene solution of 2mDBtBPDBq-VIII and FIG. 13B shows an emission spectrum thereof. FIG. 14A shows an absorption spectrum of a thin film of 2mDBtBPDBq-VIII and FIG. 14B shows an emission spectrum thereof. The conditions of the measurement were similar to those in Example 1. According to FIGS. 13A and 13B, the absorption peaks of the toluene solution of 2mDBtBPDBq-VIII are observed around 211 nm, 281 nm, 296 nm, 312 nm, 341 nm, and 374 nm, and the emission wavelength peaks are observed at 385 nm and 407 nm. According to FIGS. 14A and 14B, the absorption peaks of the thin film of 2mDBtBPDBq-VIII are observed around 207 nm, 263 nm, 300 nm, 316 nm, 348 nm, 366 nm, and 383 nm, and the emission wavelength peak is observed at 424 nm (excitation wavelength: 346 nm).

The ionization potential of 2mDBtBPDBq-VIII in a thin film state was measured by a photoelectron spectrometer (AC-3, manufactured by Riken Keiki, Co., Ltd.) in the air. The obtained value of the ionization potential was converted into a negative value, so that the HOMO level of 2mDBt-BPDBq-VIII was −6.31 eV. From the data of the absorption spectrum of the thin film in FIG. 14A, the absorption edge of 2mDBtBPDBq-VIII, which was obtained from Tauc plot with an assumption of direct transition, was 3.10 eV. Thus, the optical energy gap of 2mDBtBPDBq-VIII in the solid state was estimated at 3.10 eV; from the values of the HOMO level obtained above and this energy gap, the LUMO level of 2mDBtBPDBq-VIII can be estimated at −3.21 eV. This reveals that 2mDBtBPDBq-VIII in the solid state has an energy gap as wide as 3.10 eV.

Another example of a method for synthesizing 2mDBt-BPDBq-VIII is described.

Step 1: Synthesis of 4,4,5,5-Tetramethyl-2-[3-(dibenzo[f,h]quinoxalin-2-yl)phenyl]-1,3,2-dioxaborolane A synthesis scheme of Step 1 is shown in (E-1).

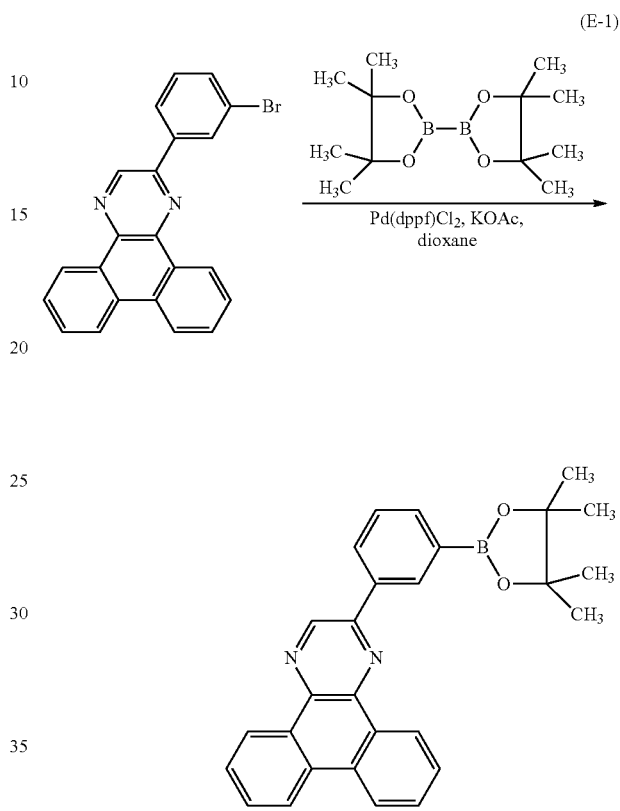

(E-1)

Into a 200 mL three-neck flask were put 5.0 g (13 mmol) of 2-(3-bromophenyl)dibenzo[f,h]quinoxaline, 3.3 g (13 mmol) of bis(pinacolato)diboron, and 3.8 g (39 mmol) of potassium acetate, and the air in the flask was replaced with nitrogen. Then, 65 mL of 1,4-dioxane was added to this mixture, and the resulting mixture was degassed by being stirred while the pressure was reduced. To this mixture, 0.48 g (0.65 mmol) of [1,1'-bis(diphenylphosphino)ferrocene] palladium(II) dichloride dichloromethane adduct was added and the mixture was stirred at 90° C. under a nitrogen stream for 2 hours. After the stirring, 40 mL of water was added to this mixture, and the resulting mixture was stirred at room temperature for 30 minutes. After the stirring, the aqueous layer of the mixture was subjected to extraction with ethyl acetate, and the solution of the extract and the organic layer were combined and washed with saturated brine. The organic layer was dried with magnesium sulfate, and this mixture was gravity-filtered. A black solid obtained by concentration of the resulting filtrate was dissolved in approximately 30 mL of hot toluene. This solution was filtered through Celite, alumina, and Florisil to give a brown solid. The solid was washed with toluene, whereby 4.9 g of a brown powder of a target substance was obtained in a yield of 87%.

Step 2: Synthesis of 2mDBtBPDBq-VIII

A synthesis scheme of Step 2 is shown in (E-2).

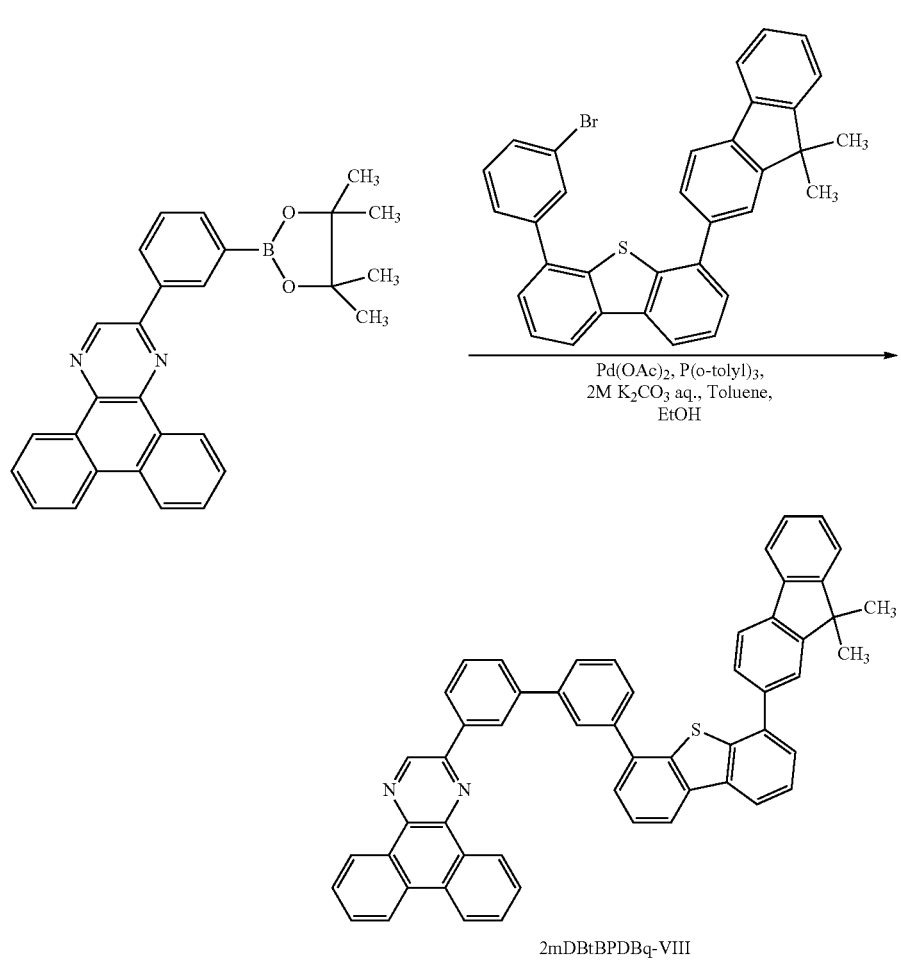

(E-2)

2mDBtBPDBq-VIII

Into a 200 mL three-neck flask were put 1.8 g (4.1 mmol) of 4,4,5,5-tetramethyl-2-[3-(dibenzo[f,h]quinoxalin-2-yl)phenyl]-1,3,2-dioxaborolane, 2.2 g (4.1 mmol) of 6-(3-bromophenyl)-4-(9,9-dimethylfluoren-2-yl)dibenzothiophene, and 0.30 g (1.0 mmol) of tri(ortho-tolyl)phosphine, and the air in the flask was replaced with nitrogen. To this mixture, 15 mL of toluene, 5.0 mL of ethanol, and 4.2 mL of an aqueous solution of potassium carbonate (2.0 mol/L) were added. This mixture was degassed by being stirred while the pressure was reduced. To this mixture was added 46 mg (0.20 mmol) of palladium(II) acetate, and the resulting mixture was stirred at 80° C. under a nitrogen stream for 5 hours. After the stirring, the aqueous layer of the mixture was subjected to extraction with toluene, and the solution of the extract and the organic layer were combined and washed with saturated brine. The organic layer was dried with magnesium sulfate, and this mixture was gravity-filtered. An oily substance obtained by concentration of the resulting filtrate was purified by silica gel column chromatography (a developing solvent of hexane:toluene=7:1) to give a white solid. The obtained solid was recrystallized with a mixed solvent of toluene and hexane, so that 2.4 g of a white solid of a target substance was obtained in a yield of 77%.

By a train sublimation method, 2.4 g of the obtained white solid was purified. In the sublimation purification, the white solid was heated at 325° C. under a pressure of 10 Pa with a flow rate of an argon gas of 5.0 mL/min. After the sublimation purification, 2.0 g of a pale yellow glassy solid of a target substance was obtained at a collection rate of 83%.

EXAMPLE 3

This example shows examination results of the solubility of the compounds which are embodiments of the present invention.

The compounds which are embodiments of the present invention and used in this example were 2mFDBtPDBq (sample 1) and 2mDBTBPDBq-VIII (sample 2). For the methods for synthesizing the compounds, Synthesis Examples 1 and 2 can be referred to. As comparative compounds, 2-[3'-(dibenzothiophen-4-yl)biphenyl-3-yl]dibenzo[f,h]quinoxaline (abbreviation: 2mDBTBPDBq-II) (comparative sample 3) and 2-[3-(dibenzothiophen-4-yl)phenyl]dibenzo[f,h]quinoxaline (abbreviation: 2mDBTP-DBq-II) (comparative sample 4) were used in this example. The purity of each compound was 99.9%. The chemical formulae of the compounds are shown below.

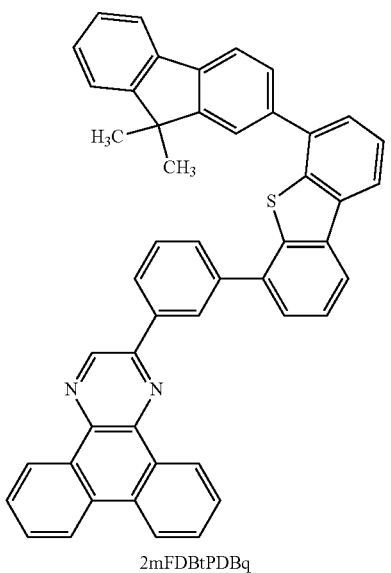

2mFDBtPDBq

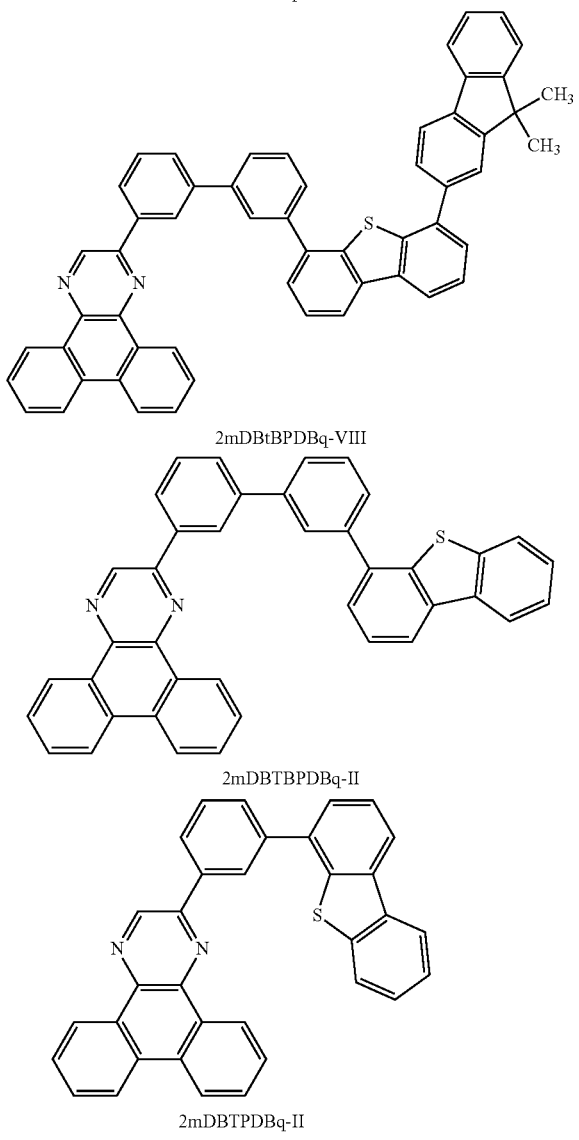

2mDBtBPDBq-VIII

2mDBTBPDBq-II

2mDBTPDBq-II

The solvents used in this example were the four kinds of solvents: toluene, chloroform, ethyl acetate, and acetone.

A method for examining the solubility of the compound of each sample is described. First, 10 mg of the compound was put into a small bottle and to this was added 1 mL of a solvent. Then, whether the compound was dissolved at room temperature or not was checked. When the compound was not dissolved at room temperature, ultrasonic wave irradiation and then heating using a dryer were performed, so that whether the compound was dissolved or not was checked.

When the compound was not dissolved after heating, the volume of the solvent was increased to 10 mL, so that whether the compound was dissolved at room temperature or not was checked. When the compound was not dissolved at room temperature, ultrasonic wave irradiation and then heating using a dryer were performed, so that whether the compound was dissolved or not was checked.

The examination results of the solubility are shown in Table 1.

TABLE 1

| | | Toluene | Chloroform | Ethyl acetate | Acetone |
|---|---|---|---|---|---|
| Sample 1 | 2mFDBtPDBq | ◉ | ◉ | ○ | ○ |
| Sample 2 | 2mDBtBPDBq-VIII | ◉ | ◉ | Δ | X |
| Comparative sample 3 | 2mDBTBPDBq-II | X | X | X | X |
| Comparative sample 4 | 2mDBTPDBq-II | ■ | Δ | X | X |

◉: dissolved at 10 mg/mL at room temperature
○: dissolved at 10 mg/mL when heated
●: dissolved at 10 mg/mL when heated but precipitated when returned to room temperature
Δ: dissolved at 10 mg/10 mL at room temperature
□: dissolved at 10 mg/10 mL when heated
■: dissolved at 10 mg/10 mL when heated but precipitated when returned to room temperature
X: not dissolved (leaving an undissolved residue)

The results in this example reveal that the compounds of embodiments of the present invention have higher solubility than the comparative compounds. In other words, the compound of one embodiment of the present invention which has a dibenzo[f,h]quinoxaline skeleton and a dibenzothiophene skeleton and in which a 9,9-dialkylfluorenyl group is bonded to the dibenzothiophene skeleton has much higher solubility than the comparative compounds which have the two skeletons and in which a 9,9-dialkylfluorenyl group is not bonded.

High solubility facilitates separation or purification (e.g., extraction, column chromatography, and recrystallization), which is performed by dissolving the compound in an organic solvent, so that impurities can be easily removed. In the case of the compound of one embodiment of the present invention, purification by sublimation is performed after a considerable reduction in the amount of impurities remaining after separation or purification by dissolving the compound in an organic solvent; thus, the compound can easily be highly purified. The number of times of performing sublimation purification for higher purity can be reduced. By using a compound from which impurities are sufficiently removed for a light-emitting element, initial deterioration is suppressed and the light-emitting element is made more reliable. In Examples below, fabrication of light-emitting elements including the compounds of embodiments of the present invention are described.

EXAMPLE 4

In this example, the light-emitting element of one embodiment of the present invention will be described.

Chemical formulae of materials used in this example are shown below. Note that the chemical formulae of the materials which are shown above are omitted.

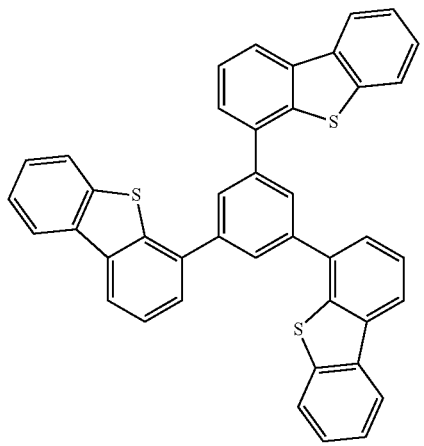

DBT3P-II

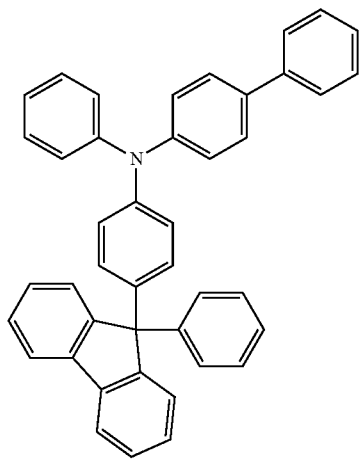

BPAFLP

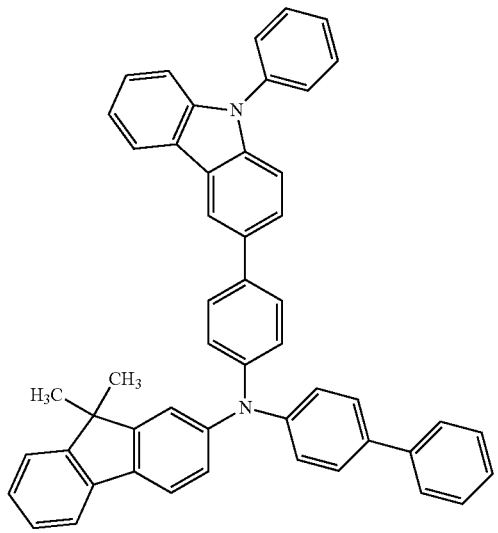

PCBBiF

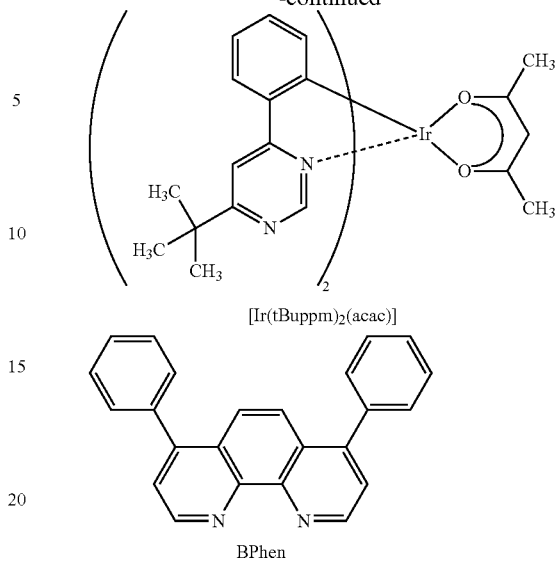

[Ir(tBuppm)$_2$(acac)]

BPhen

Figure 15:
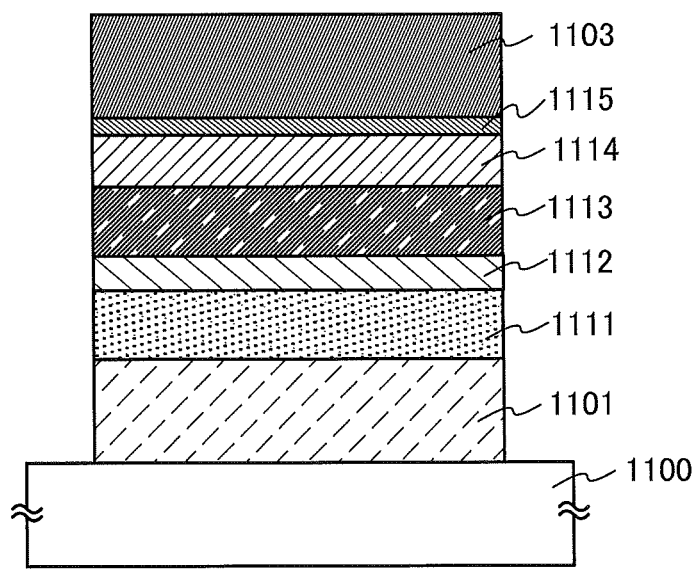
FIG. 15 illustrates light-emitting elements in Examples 4 to 9.

Methods for manufacturing a light-emitting element 1, a comparative light-emitting element 2, and a comparative light-emitting element 3 in this example will be described below. For the structure of each of the light-emitting elements in this example, FIG. 15 can be referred to.

(Light-emitting Element 1)

A film of indium tin oxide containing silicon (ITSO) was formed over a glass substrate 1100 by a sputtering method, so that a first electrode 1101 which functions as an anode was formed. The thickness thereof was 110 nm and the electrode area was 2 mm×2 mm.

Next, as pretreatment for forming the light-emitting element over the glass substrate 1100, UV-ozone treatment was performed for 370 seconds after washing of a surface of the glass substrate 1100 with water and baking that was performed at 200° C. for 1 hour.

After that, the glass substrate 1100 was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the glass substrate 1100 was cooled down for approximately 30 minutes.

Then, the glass substrate 1100 over which the first electrode 1101 was formed was fixed to a substrate holder provided in the vacuum evaporation apparatus so that the surface on which the first electrode 1101 was formed faced downward. The pressure in the vacuum evaporation apparatus was reduced to approximately $10^{-4}$ Pa. After that, over the first electrode 1101, 4,4′,4″-(1,3,5-benzenetriyl)tri (dibenzothiophene) (abbreviation: DBT3P-II) and molybdenum(VI) oxide were deposited by co-evaporation, so that a hole-injection layer 1111 was formed. The thickness of the hole-injection layer 1111 was set to 20 nm, and the weight ratio of DBT3P-II to molybdenum oxide was adjusted to 4:2 (=DBT3P-II: molybdenum oxide). Note that the co-evaporation method refers to an evaporation method in which evaporation is carried out from a plurality of evaporation sources at the same time in one treatment chamber.

Next, a film of 4-phenyl-4′-(9-phenylfluoren-9-yl)triphenylamine (abbreviation: BPAFLP) was formed to a thickness of 20 nm over the hole-injection layer 1111 to form a hole-transport layer 1112.

Furthermore, a light-emitting layer 1113 was formed over the hole-transport layer 1112 by co-evaporation of 2mFDBtPDBq, N-(1,1'-biphenyl-4-yl)-N-[4-(9-phenyl-9H-carbazol-3-yl)phenyl]-9,9-dimethyl-9H-fluoren-2-amine (abbreviation: PCBBiF), and (acetylacetonato)bis(6-tert-butyl-4-phenylpyrimidinato)iridium(III) (abbreviation: [Ir(tBuppm)$_2$(acac)]). Here, a 20-nm-thick layer which was formed with the weight ratio of 2mFDBtPDBq to PCBBiF to [Ir(tBuppm)$_2$(acac)] adjusted to 0.7:0.3:0.05 (=2mFDBtPDBq: PCBBiF: [Ir(tBuppm)$_2$(acac)]) and a 20-nm-thick layer which was formed with the weight ratio adjusted to 0.8:0.2:0.05 (=2mFDBtPDBq: PCBBiF: [Ir(tBuppm)$_2$(acac)]) were stacked.

Next, a film of 2mFDBtPDBq was formed to a thickness of 20 nm over the light-emitting layer 1113 and then a film of bathophenanthroline (abbreviation: BPhen) was formed to a thickness of 10 nm, so that an electron-transport layer 1114 was formed.

After that, over the electron-transport layer 1114, a film of lithium fluoride (LiF) was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 1 of this example was fabricated.

(Comparative Light-emitting Element 2)

Components of the comparative light-emitting element 2 other than the light-emitting layer 1113 and the electron-transport layer 1114 were formed in the same manners as those of the light-emitting element 1. Here, only the steps different from those in the method for fabricating the light-emitting element 1 are described.

The light-emitting layer 1113 of the comparative light-emitting element 2 was formed by co-evaporation of 2mDBTBPDBq-II, PCBBiF, and [Ir(tBuppm)$_2$(acac)]. Here, a 20-nm-thick layer which was formed with the weight ratio of 2mDBTBPDBq-II to PCBBiF to [Ir(tBuppm)$_2$(acac)] adjusted to 0.7:0.3:0.05 (=2mDBTBPDBq-II: PCBBiF: [Ir(tBuppm)$_2$(acac)]) and a 20-nm-thick layer which was formed with the weight ratio adjusted to 0.8:0.2:0.05 (=2mDBTBPDBq-II: PCBBiF: [Ir(tBuppm)$_2$(acac)]) were stacked.

The electron-transport layer 1114 of the comparative light-emitting element 2 was formed by depositing 2mDBTBPDBq-II to a thickness of 20 nm and further depositing BPhen to a thickness of 10 nm.

(Comparative Light-emitting Element 3) Components of the comparative light-emitting element 3 other than the light-emitting layer 1113 and the electron-transport layer 1114 were formed in the same manners as those of the light-emitting element 1. Here, only the steps different from those in the method for fabricating the light-emitting element 1 are described.

The light-emitting layer 1113 of the comparative light-emitting element 3 was formed by co-evaporation of 2mDBTPDBq-II, PCBBiF, and [Ir(tBuppm)$_2$(acac)]. Here, a 20-nm-thick layer which was formed with the weight ratio of 2mDBTPDBq-II to PCBBiF to [Ir(tBuppm)$_2$(acac)] adjusted to 0.7:0.3:0.05 (=2mDBTPDBq-II: PCBBiF: [Ir(tBuppm)$_2$(acac)]) and a 20-nm-thick layer which was formed with the weight ratio adjusted to 0.8:0.2:0.05 (=2mDBTPDBq-II: PCBBiF: [Ir(tBuppm)$_2$(acac)]) were stacked.

The electron-transport layer 1114 of the comparative light-emitting element 3 was formed by depositing 2mDBTPDBq-II to a thickness of 20 nm and further depositing BPhen to a thickness of 10 nm.

Note that in all the above evaporation steps, evaporation was performed by a resistance-heating method.

Table 2 shows the element structures of the light-emitting elements fabricated as described above in this example. Table 2 also shows element structures of a light-emitting element 1b, a comparative light-emitting element 2b, and a comparative light-emitting element 3b described in Example 5.

TABLE 2

| | First electrode | Hole-injection layer | Hole-transport layer | Light-emitting layer | | Electron-transport layer | Electron-injection layer | Second electrode |
|---|---|---|---|---|---|---|---|---|
| Light-emitting element 1 (1b) | ITSO 110 nm | DBT3P-II:MoO$_x$ (=4:2) 20 nm | BPAFLP 20 nm | 2mFDBtPDBq:PCBBiF:[Ir(tBuppm)$_2$(acac)] (=0.7:0.3:0.05) 20 nm | (=0.8:0.2:0.05) 20 nm | 2mFDBtPDBq 20 nm | BPhen 10 nm | LiF 1 nm | Al 200 nm |
| Comparative light-emitting element 2 (2b) | ITSO 110 nm | DBT3P-II:MoO$_x$ (=4:2) 20 nm | BPAFLP 20 nm | 2mDBTBPDBq-II:PCBBiF:[Ir(tBuppm)$_2$(acac)] (=0.7:0.3:0.05) 20 nm | (=0.8:0.2:0.05) 20 nm | 2mDBTBPDBq-II 20 nm | BPhen 10 nm | LiF 1 nm | Al 200 nm |
| Comparative light-emitting element 3 (3b) | ITSO 110 nm | DBT3P-II:MoO$_x$ (=4:2) 20 nm | BPAFLP 20 nm | 2mDBTPDBq-II:PCBBiF:[Ir(tBuppm)$_2$(acac)] (=0.7:0.3:0.05) 20 nm | (=0.8:0.2:0.05) 20 nm | 2mDBTPDBq-II 20 nm | BPhen 10 nm | LiF 1 nm | Al 200 nm |

The light-emitting elements of this example were each sealed with a glass substrate in a glove box under a nitrogen atmosphere so as not to be exposed to the air (specifically, a sealant was applied to surround the element, and at the time of sealing, UV treatment was performed and then heat treatment was performed at 80° C. for 1 hour). Then, the operation characteristics of the light-emitting elements were measured. Note that the measurement was carried out at room temperature (in an atmosphere kept at 25° C.).

Figure 16:
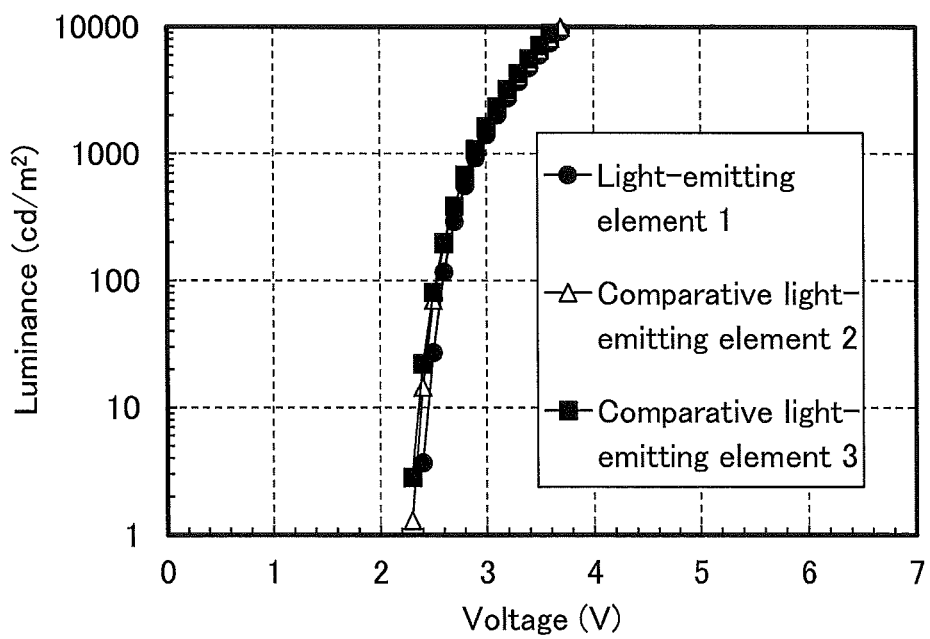
FIG. 16 is a graph showing voltage-luminance characteristics of light-emitting elements in Example 4.
Figure 17:
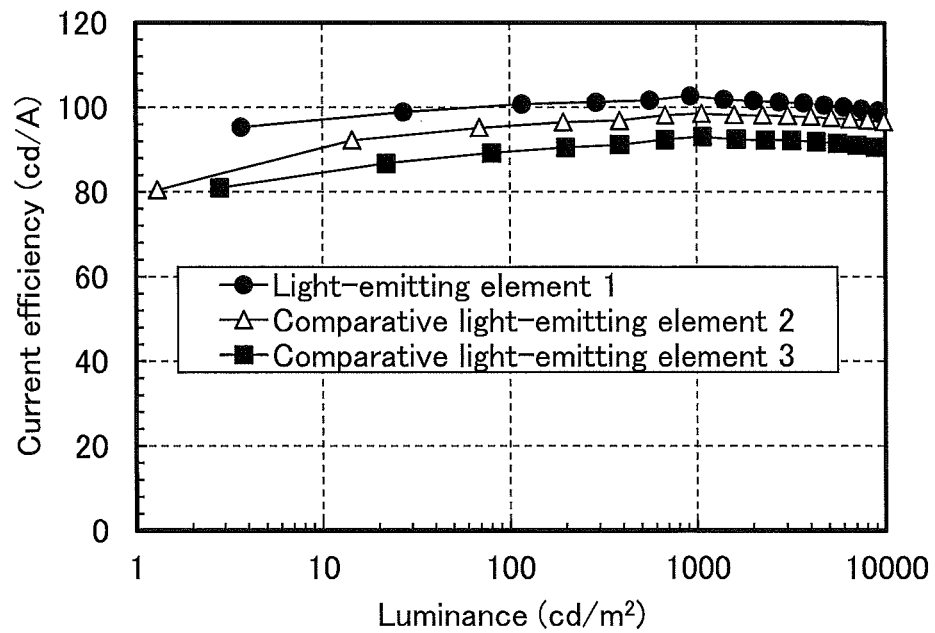
FIG. 17 is a graph showing luminance-current efficiency characteristics of light-emitting elements in Example 4.
Figure 18:
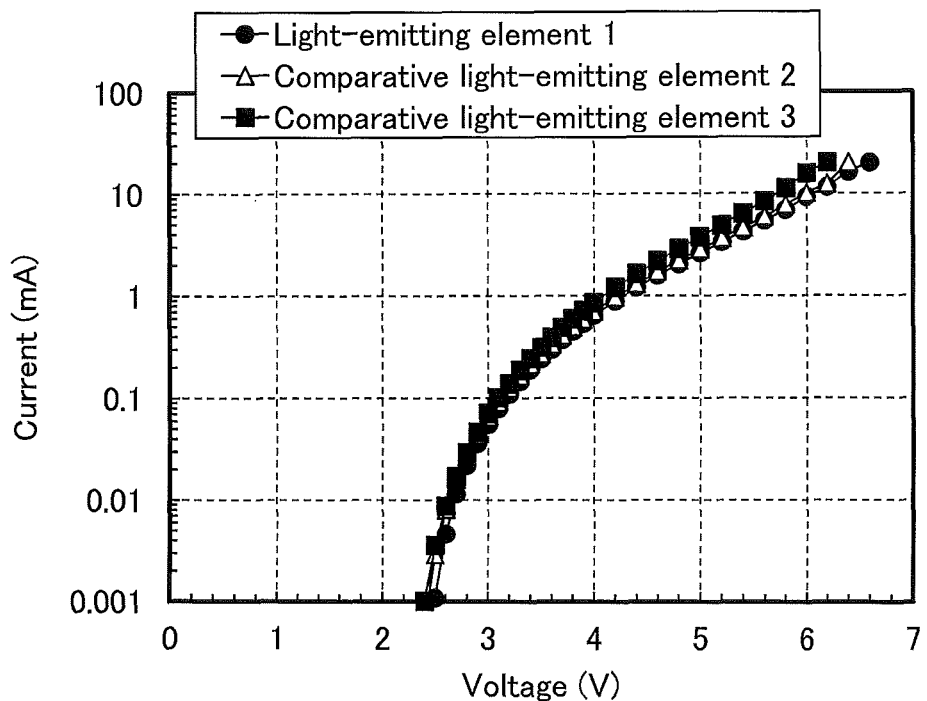
FIG. 18 is a graph showing voltage-current characteristics of light-emitting elements in Example 4.

FIG. 16 shows the voltage-luminance characteristics of the light-emitting elements of this example. In each of the graphs showing voltage-luminance characteristics in Examples, the horizontal axis indicates voltage (V) and the vertical axis indicates luminance (cd/m$^2$). FIG. 17 shows luminance-current efficiency characteristics. In each of the graphs showing luminance-current efficiency characteristics in Examples, the horizontal axis indicates luminance (cd/ m$^2$) and the vertical axis indicates current efficiency (cd/A). FIG. 18 shows voltage-current characteristics. In each of the graphs showing voltage-current characteristics in Examples, the horizontal axis indicates voltage (V) and the vertical axis indicates current (mA). Table 3 shows the voltage (V), current density (mA/cm$^2$), CIE chromaticity coordinates (x, y), current efficiency (cd/A), power efficiency (lm/W), and external quantum efficiency (%) of the light-emitting elements at a luminance of approximately 1000 cd/m$^2$.

solvent than 2mDBTBPDBq-II used in the comparative light-emitting element 2 and 2mDBTPDBq-II used in the comparative light-emitting element 3. A compound with high solubility can be easily purified and impurities thereof can be easily eliminated. The use of the compound of one embodiment of the present invention from which impurities are sufficiently removed probably allowed the light-emitting element to have suppressed initial deterioration and high reliability.

TABLE 3

|  | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 1 | 2.9 | 0.90 | 0.42 | 0.57 | 900 | 103 | 111 | 27 |
| Comparative light-emitting element 2 | 2.9 | 1.08 | 0.42 | 0.57 | 1100 | 99 | 107 | 26 |
| Comparative light-emitting element 3 | 2.9 | 1.16 | 0.42 | 0.57 | 1100 | 93 | 101 | 24 |

Figure 19:
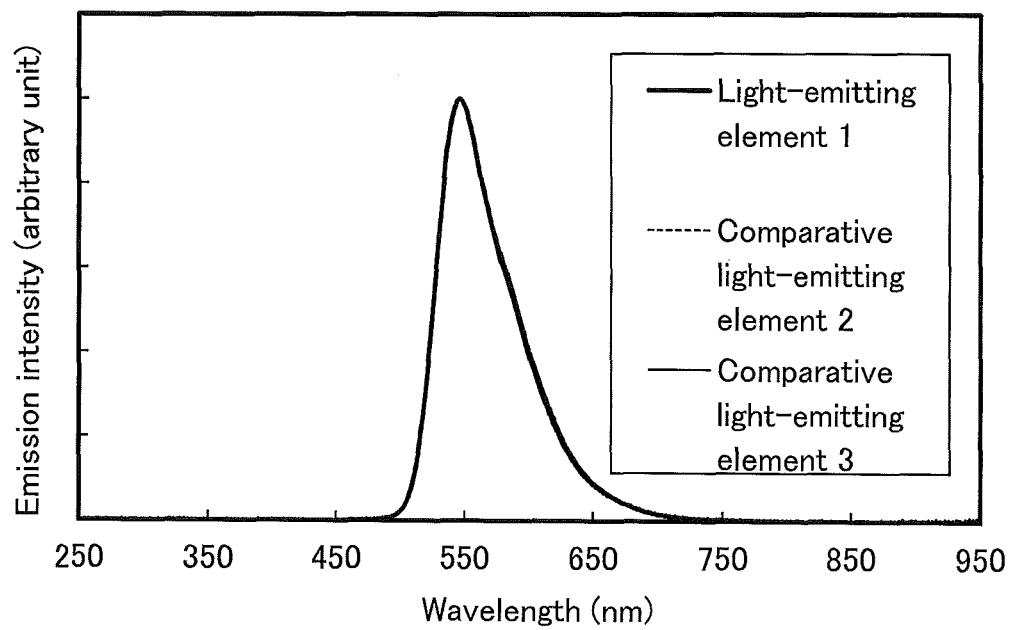
FIG. 19 is a graph showing emission spectra of light-emitting elements in Example 4.

The CIE chromaticity coordinates (x, y) at a luminance of approximately 1000 cd/m$^2$ of the light-emitting elements were (0.42, 0.57) and the light-emitting elements emitted yellowish green light. FIG. 19 shows emission spectra when a current at a current density of 2.5 mA/cm$^2$ was supplied to the light-emitting elements. In each of the graphs showing emission spectra in Examples, the horizontal axis indicates wavelength (nm) and the vertical axis indicates emission intensity (arbitrary unit). As shown in FIG. 19, the emission spectra of the light-emitting elements each have a peak at approximately 546 nm. These results show that yellowish green light emission originating from [Ir(tBuppm)$_2$(acac)] was provided from each of the light-emitting elements in this example.

The measurement results of the operation characteristics show that the light-emitting elements in this example each have high emission efficiency and a low drive voltage.

Figure 20:
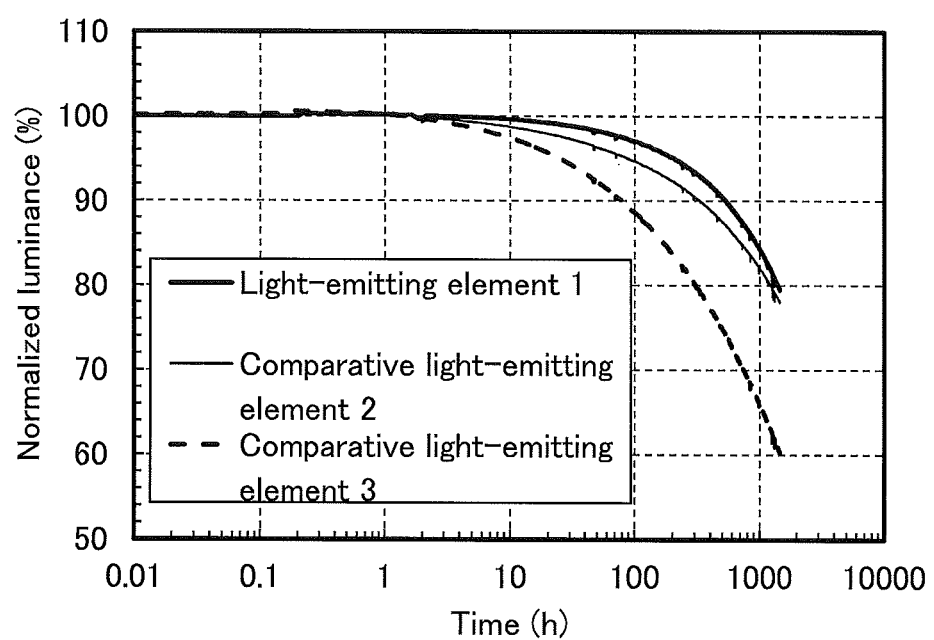
FIG. 20 shows results of reliability tests of light-emitting elements in Example 4.

Reliability tests of the light-emitting elements in this example were conducted. FIG. 20 shows results of the reliability tests. In each of the graphs showing reliability test results in Examples, the vertical axis indicates normalized luminance (%) with an initial luminance of 100% and the horizontal axis indicates driving time (h) of the element. In the reliability tests, which were conducted at room temperature, the light-emitting elements were each driven under the conditions where the initial luminance was set to 5000 cd/m$^2$ and the current density was constant. FIG. 20 shows that after 1500 hours elapsed, the light-emitting element 1 kept 80% of the initial luminance, the comparative light-emitting element 2 kept 78% of the initial luminance, and the comparative light-emitting element 3 kept 60% of the initial luminance. The results of the reliability tests show that the light-emitting element 1 has a longer lifetime than the comparative light-emitting element 2 and the comparative light-emitting element 3.

As described in Example 3, 2mFDBtPDBq used in the light-emitting element 1 has higher solubility in an organic

EXAMPLE 5

This example will show results of a preservation test of a fabricated light-emitting element of one embodiment of the present invention.

In this example, the light-emitting element 1*b*, the comparative light-emitting element 2*b*, and the comparative light-emitting element 3*b* were manufactured. The structure and manufacturing method of the light-emitting element 1*b* are the same as those of the light-emitting element 1 in Example 4. The structure and manufacturing method of the comparative light-emitting element 2*b* are the same as those of the comparative light-emitting element 2 in Example 4, and the structure and manufacturing method of the comparative light-emitting element 3*b* are the same as those of the comparative light-emitting element 3 in Example 4.

In this example, the light-emitting elements were each preserved in a thermostatic oven maintained at 100° C. for a predetermined time, and the operation characteristics were measured. Note that the operation characteristics were measured at room temperature (in an atmosphere kept at 25° C.) after the light-emitting elements were taken out of the thermostatic oven.

Figure 21:
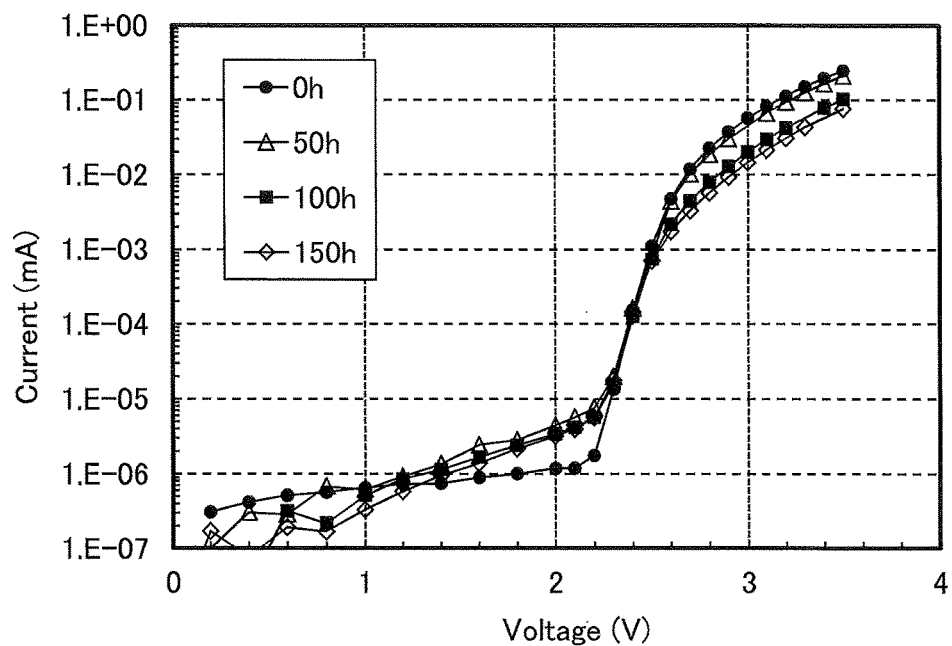
FIG. 21 is a graph showing voltage-current characteristics of a light-emitting element 1b.
Figure 22:
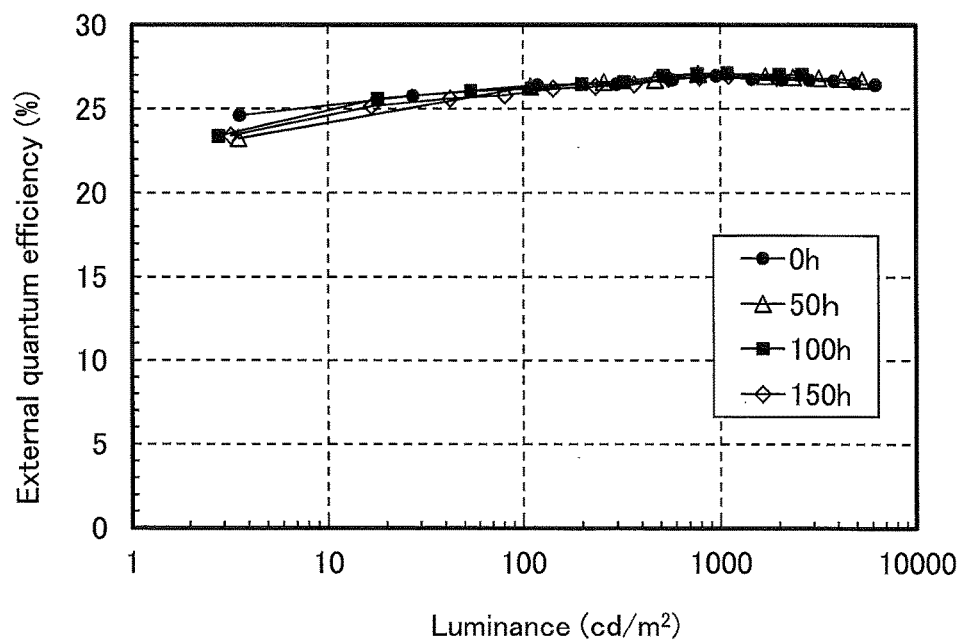
FIG. 22 is a graph showing luminance-external quantum efficiency characteristics of a light-emitting element 1b.

FIG. 21 shows the voltage-current characteristics of the light-emitting element 1*b* after preservation at 100° C. for 150 hours. FIG. 22 shows the luminance-external quantum efficiency characteristics of the light-emitting element 1*b* after preservation at 100° C. for 150 hours. In each of the graphs showing luminance-external quantum efficiency characteristics in Examples, the horizontal axis indicates luminance (cd/m$^2$) and the vertical axis indicates external quantum efficiency (%). Note that in each of FIGS. 21 and 22, the characteristics of the light-emitting element 1*b* measured before the preservation test, after 50-hour preservation, and after 100-hour preservation are also shown.

Figure 23:
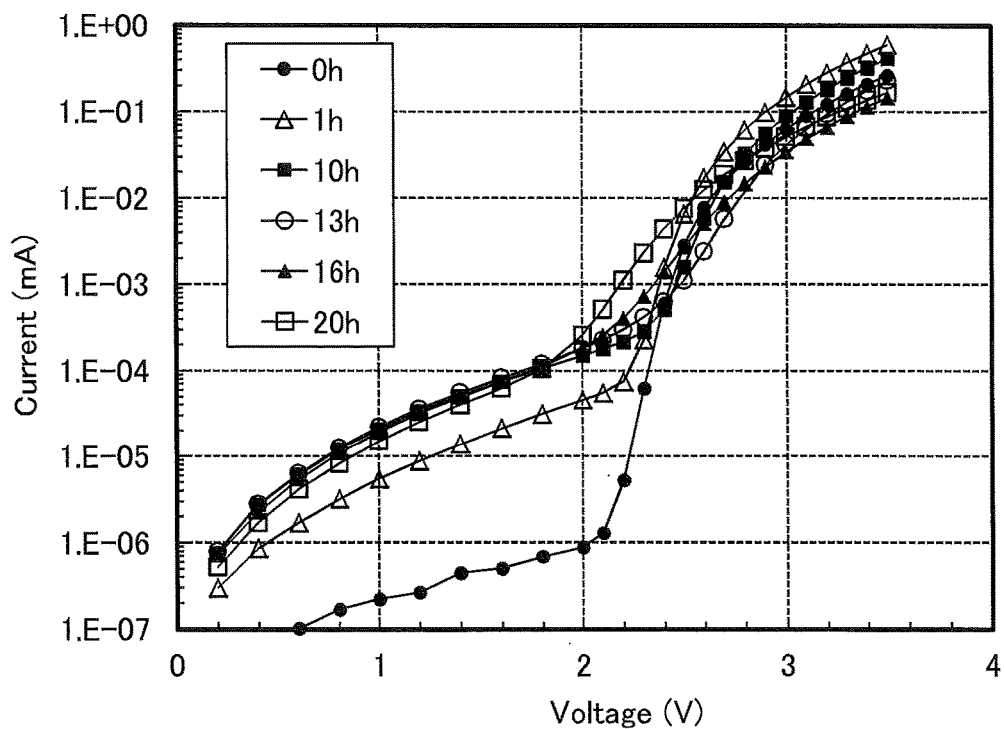
FIG. 23 is a graph showing voltage-current characteristics of a comparative light-emitting element 2b.
Figure 24:
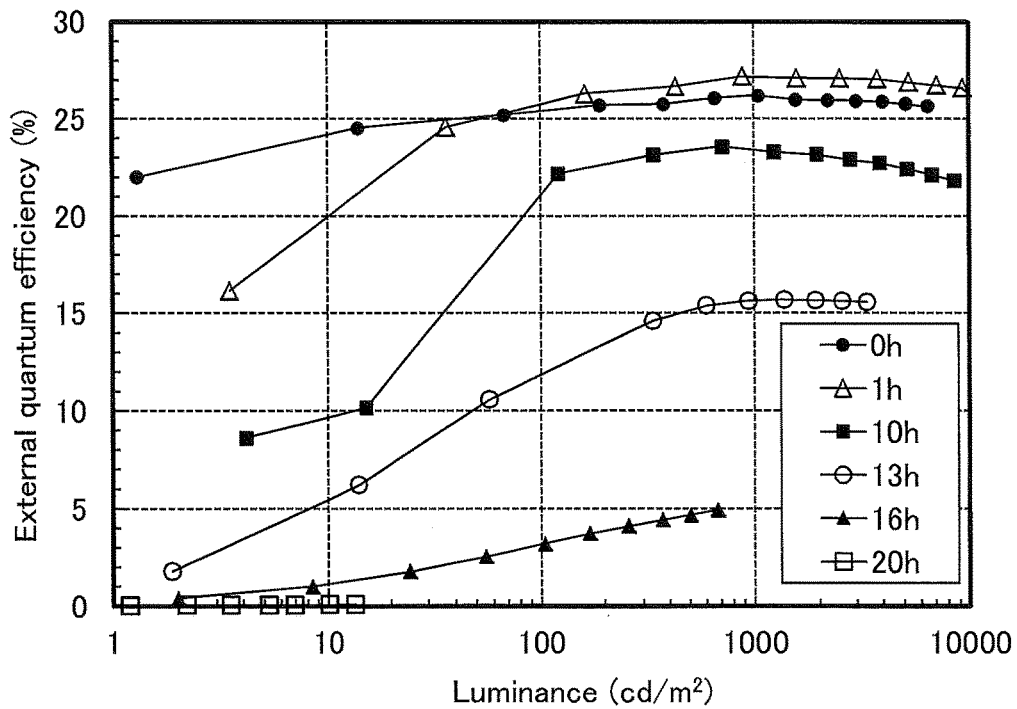
FIG. 24 is a graph showing luminance-external quantum efficiency characteristics of a comparative light-emitting element 2b.

FIGS. 23 and 24 respectively show the voltage-current characteristics and luminance-external quantum efficiency characteristics of the comparative light-emitting element 2*b* after preservation at 100° C. for 20 hours. Note that in each of FIGS. 23 and 24, the characteristics of the comparative light-emitting element 2b measured before the preservation test, after 1-hour preservation, after 10-hour preservation, after 13-hour preservation, and after 16-hour preservation are also shown.

Figure 25:
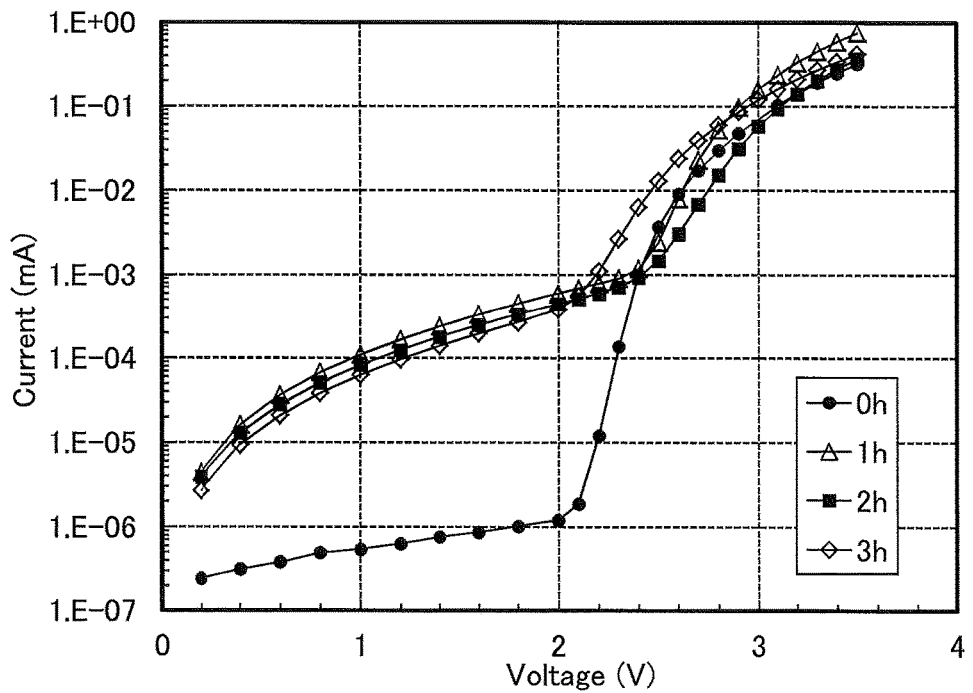
FIG. 25 is a graph showing voltage-current characteristics of a comparative light-emitting element 3b.
Figure 26:
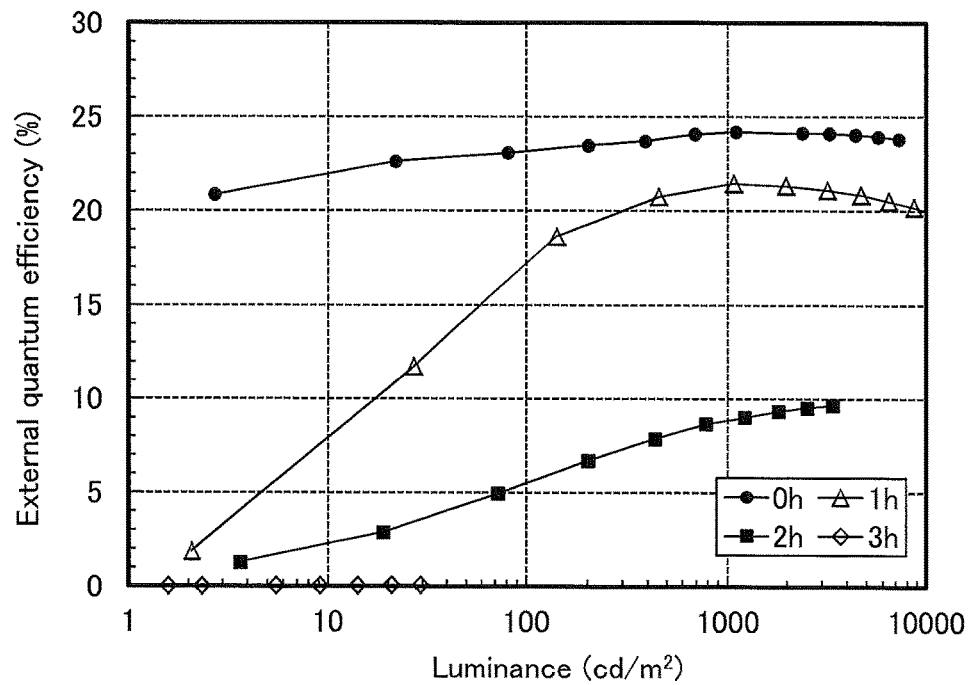
FIG. 26 is a graph showing luminance-external quantum efficiency characteristics of a comparative light-emitting element 3b.

FIGS. 25 and 26 respectively show the voltage-current characteristics and luminance-external quantum efficiency characteristics of the comparative light-emitting element 3b after preservation at 100° C. for 3 hours. Note that in each of FIGS. 25 and 26, the characteristics of the comparative light-emitting element 3b measured before the preservation test, after 1-hour preservation, and after 2-hour preservation are also shown.

From FIGS. 21 and 22, although preserved at 100° C. for 150 hours, the light-emitting element 1b had only a small change in voltage-current characteristics and luminance-external quantum efficiency characteristics and suffered little deterioration in element characteristics. In contrast, as can be seen from FIGS. 23 to 26, the comparative light-emitting elements 2b and 3b were considerably changed in voltage-current characteristics and luminance-external quantum efficiency characteristics and suffered deterioration in element characteristics as a result of the preservation at 100° C. It is also shown that the comparative light-emitting element 2b after the preservation at 100° C. for 20 hours and the comparative light-emitting element 3b after the preservation at 100° C. for 3 hours hardly emitted light.

Figure 27:
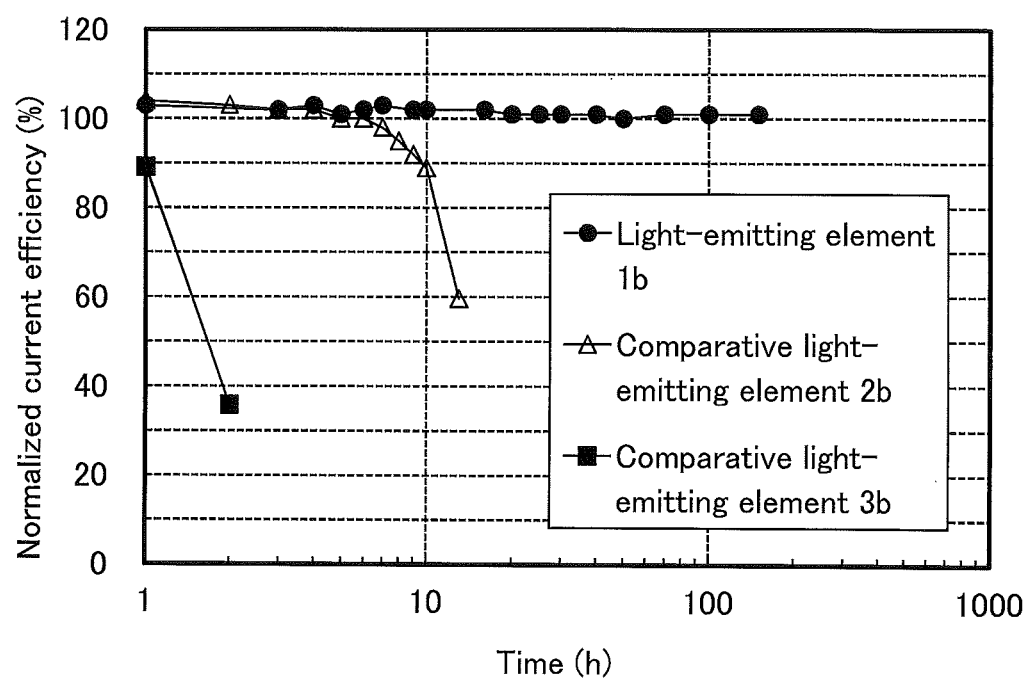
FIG. 27 shows results of preservation tests of light-emitting elements in Example 5.

FIG. 27 shows preservation test results in this example. In each of the graphs showing the preservation test results in Examples, the vertical axis indicates normalized current efficiency (%) where the current efficiency of the element at a luminance of 1000 cd/m² before the preservation test is 100%, and the horizontal axis indicates preservation time (h) at 100° C.

As can be seen from the measurement results, the current efficiency of the light-emitting element 1b was hardly changed even after preservation at 100° C. for 150 hours. In contrast, the current efficiencies of the comparative light-emitting elements 2b and 3b were greatly reduced, which suggests current leakage.

The above results show that in high-temperature preservation tests, behavior of the light-emitting element 1b that includes 2mFDBtPDBq with a 9,9-dialkylfluorenyl group is significantly different from behavior of the comparative light-emitting element 2b or 3b that includes 2mDBTBP-DBq-II or 2mDBTPDBq-II without a 9,9-dialkylfluorenyl group. In other words, the characteristics of the comparative light-emitting elements 2b and 3b considerably deteriorate while the characteristics of the light-emitting element 1b hardly deteriorate.

It was thus found that when including the compound of one embodiment of the present invention in which a dibenzothiophene skeleton has a 9,9-dialkylfluorenyl group as a substituent, a light-emitting element has higher heat resistance and a longer lifetime than when including a compound without a 9,9-dialkylfluorenyl group as a substituent.

EXAMPLE 6

In this example, the light-emitting element of one embodiment of the present invention will be described. A chemical formula of a material used in this example is shown below. Note that the chemical formulae of the materials which are shown above are omitted.

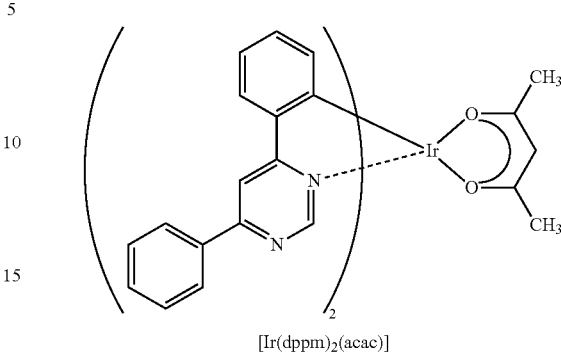

[Ir(dppm)₂(acac)]

Methods for manufacturing a light-emitting element 4 and a comparative light-emitting element 5 of this example will be described below. For the structure of each of the light-emitting elements in this example, FIG. 15 can be referred to.

(Light-emitting Element 4)

Components of the light-emitting element 4 other than the light-emitting layer 1113 were formed in the same manners as those of the light-emitting element 1. Here, only the steps different from those in the method for fabricating the light-emitting element 1 are described.

The light-emitting layer 1113 of the light-emitting element 4 was formed by co-evaporation of 2mFDBtPDBq, PCBBiF, and (acetylacetonato)bis(4,6-diphenylpyrimidinato)iridium(III) (abbreviation: [Ir(dppm)₂(acac)]). Here, a 20-nm-thick layer which was formed with the weight ratio of 2mFDBtPDBq to PCBBiF to [Ir(dppm)₂(acac)] adjusted to 0.7:0.3:0.05 (=2mFDBtPDBq: PCBBiF: [Ir(dppm)₂(acac)]) and a 20-nm-thick layer which was formed with the weight ratio adjusted to 0.8:0.2:0.05 (=2mFDBtPDBq: PCBBiF: [Ir(dppm)₂(acac)]) were stacked.

(Comparative Light-emitting Element 5)

Components of the comparative light-emitting element 5 other than the light-emitting layer 1113 and the electron-transport layer 1114 were formed in the same manners as those of the comparative light-emitting element 2. Here, only the steps different from those in the method for fabricating the comparative light-emitting element 2 are described.

The light-emitting layer 1113 of the comparative light-emitting element 5 was formed by co-evaporation of 2mDBTBPDBq-II, PCBBiF, and [Ir(dppm)₂(acac)]. Here, a 20-nm-thick layer which was formed with the weight ratio of 2mDBTBPDBq-II to PCBBiF to [Ir(dppm)₂(acac)] adjusted to 0.7:0.3:0.05 (=2mDBTBPDBq-II: PCBBiF: [Ir(dppm)₂(acac)]) and a 20-nm-thick layer which was formed with the weight ratio adjusted to 0.8:0.2:0.05 (=2mDBTBPDBq-II: PCBBiF: [Ir(dppm)₂(acac)]) were stacked.

Table 4 shows the element structures of the light-emitting elements fabricated as described above in this example.

TABLE 4

| | First electrode | Hole-injection layer | Hole-transport layer | Light-emitting layer | | Electron-transport layer | | Electron-injection layer | Second electrode |
|---|---|---|---|---|---|---|---|---|---|
| Light-emitting element 4 | ITSO 110 nm | DBT3P-II:MoO$_x$ (=4:2) 20 nm | BPAFLP 20 nm | 2mFDBtPDBq:PCBBiF:[Ir(dppm)$_2$(acac)] (=0.7:0.3:0.05) 20 nm | (=0.8:0.2:0.05) 20 nm | 2mFDBtPDBq 20 nm | BPhen 10 nm | LiF 1 nm | Al 200 nm |
| Comparative light-emitting element 5 | ITSO 110 nm | DBT3P-II:MoO$_x$ (=4:2) 20 nm | BPAFLP 20 nm | 2mDBTBPDBq-II:PCBBiF:[Ir(dppm)$_2$(acac)] (=0.7:0.3:0.05) 20 nm | (=0.8:0.2:0.05) 20 nm | 2mDBTBPDBq-II 20 nm | BPhen 10 nm | LiF 1 nm | Al 200 nm |

The light-emitting elements of this example were each sealed with a glass substrate in a glove box under a nitrogen atmosphere so as not to be exposed to the air (specifically, a sealant was applied to surround the element, and at the time of sealing, UV treatment was performed and then heat treatment was performed at 80° C. for 1 hour). Then, the operation characteristics of the light-emitting elements were measured. Note that the measurement was carried out at room temperature (in an atmosphere kept at 25° C.).

Figure 28:
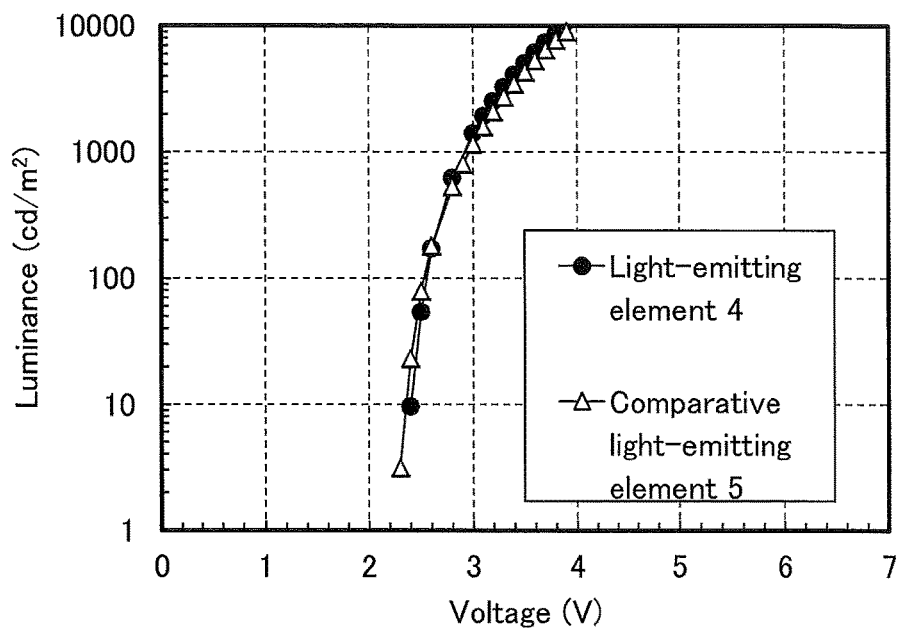
FIG. 28 is a graph showing voltage-luminance characteristics of light-emitting elements in Example 6.
Figure 29:
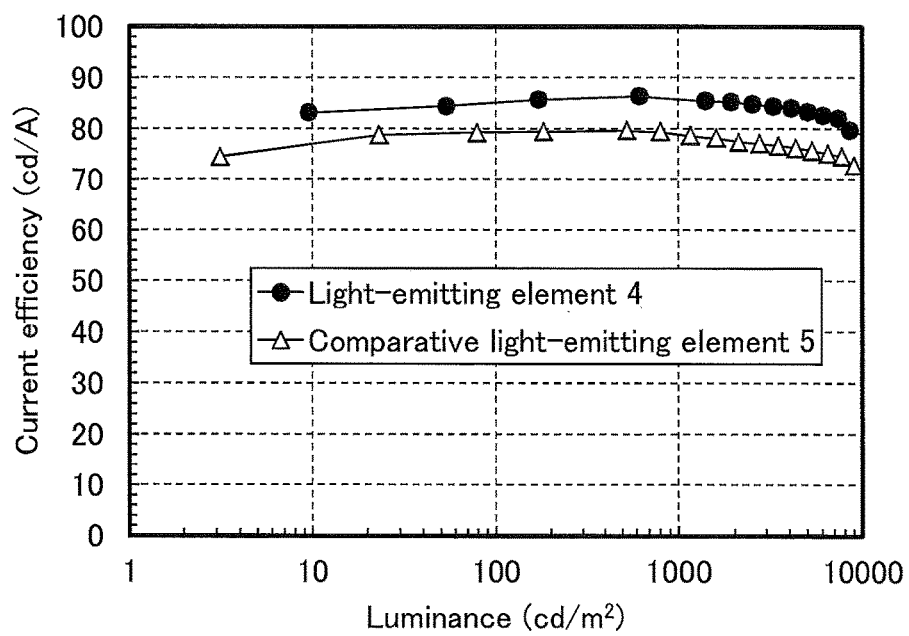
FIG. 29 is a graph showing luminance-current efficiency characteristics of light-emitting elements in Example 6.
Figure 30:
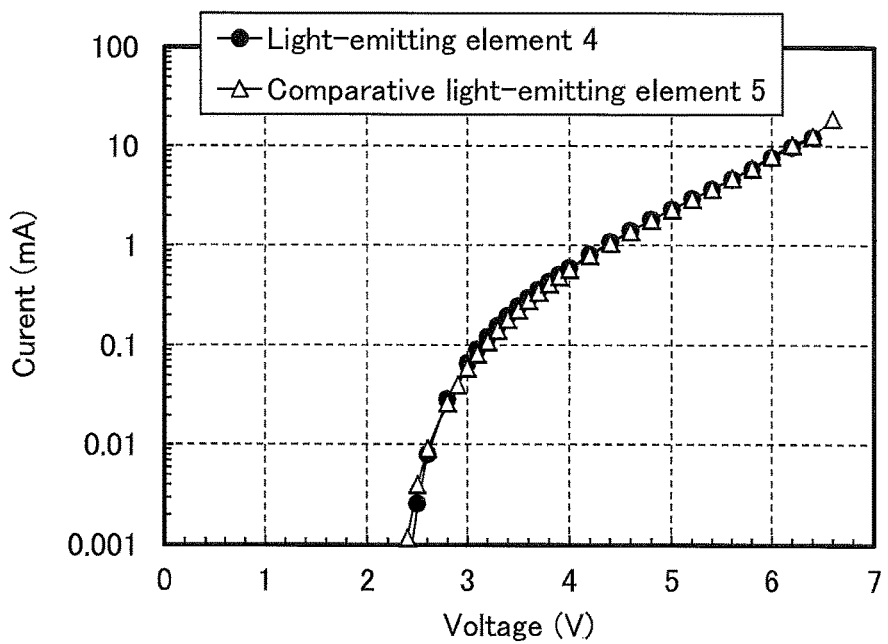
FIG. 30 is a graph showing voltage-current characteristics of light-emitting elements in Example 6.

FIG. 28 shows the voltage-luminance characteristics of the light-emitting elements of this example. FIG. 29 shows luminance-current efficiency characteristics. FIG. 30 shows voltage-current characteristics. Table 5 shows the voltage (V), current density (mA/cm$^2$), CIE chromaticity coordinates (x, y), current efficiency (cd/A), power efficiency (lm/W), and external quantum efficiency (%) of the light-emitting elements at a luminance of approximately 1000 cd/m$^2$.

TABLE 5

| | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
|---|---|---|---|---|---|---|---|---|
| Light-emitting element 4 | 2.9 | 1.1 | 0.55 | 0.45 | 1000 | 85 | 92 | 31 |
| Comparative light-emitting element 5 | 3.0 | 1.5 | 0.56 | 0.44 | 1200 | 79 | 82 | 30 |

Figure 31:
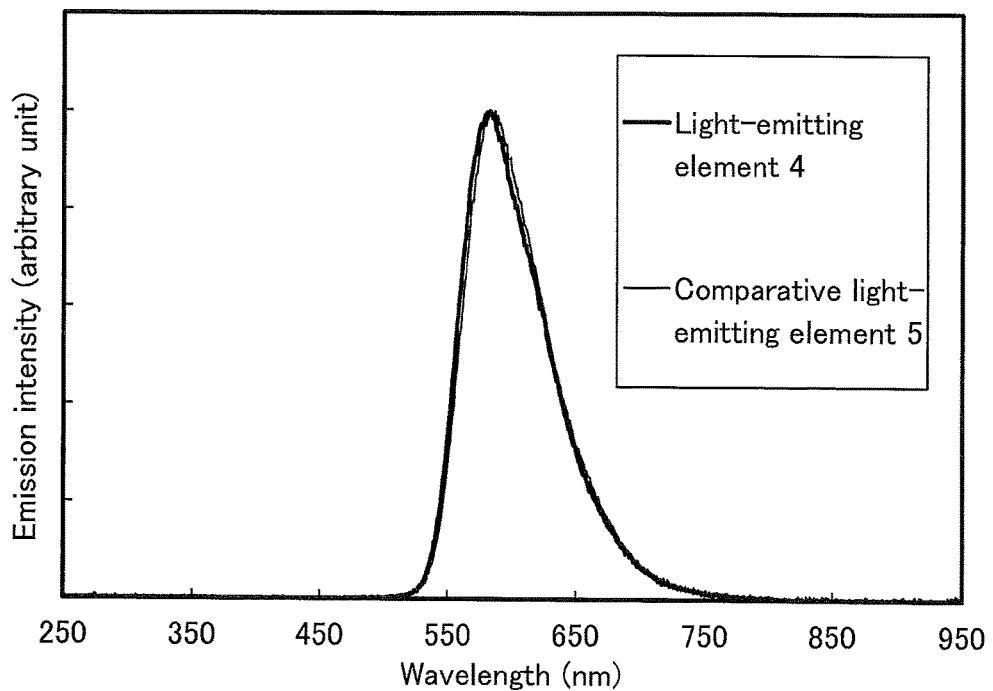
FIG. 31 is a graph showing emission spectra of light-emitting elements in Example 6.

The CIE chromaticity coordinates (x, y) at a luminance of 1000 cd/m$^2$ of the light-emitting element 4 were (0.55, 0.45), and those at a luminance of 1200 cd/m$^2$ of the comparative light-emitting element 5 were (0.56, 0.44). The light-emitting elements emitted orange light. FIG. 31 shows emission spectra when a current at a current density of 2.5 mA/cm$^2$ was supplied to the light-emitting elements. As shown in FIG. 31, the emission spectrum of the light-emitting element 4 has a peak at approximately 583 nm, and that of the comparative light-emitting element 5 has a peak at approximately 587 mm. These results show that orange light emission originating from [Ir(dppm)$_2$(acac)] was provided from each of the light-emitting elements in this example.

The measurement results of the operation characteristics show that the light-emitting elements in this example each have high emission efficiency and a low drive voltage.

Figure 32:
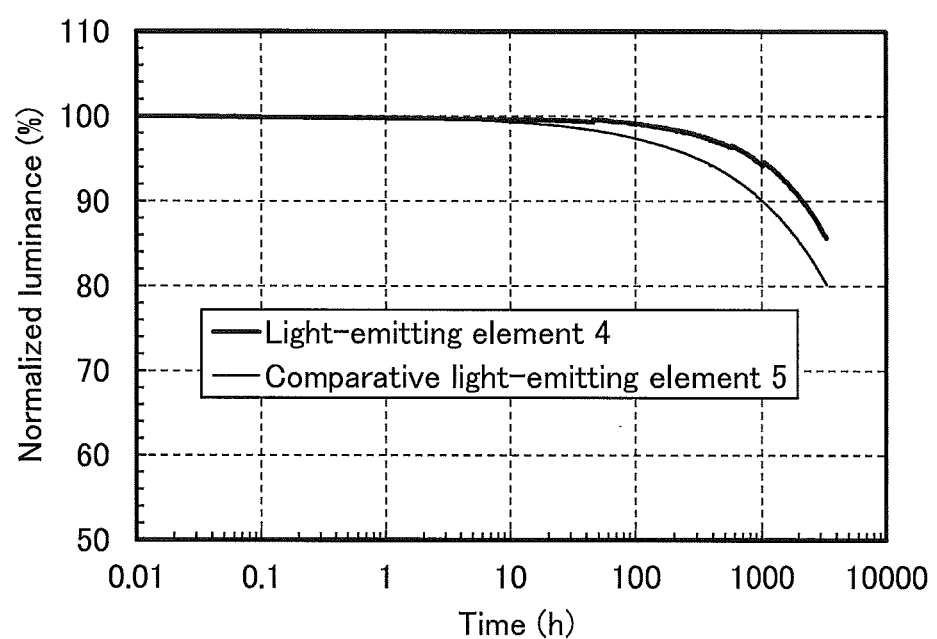
FIG. 32 shows results of reliability tests of light-emitting elements in Example 6.

Reliability tests of the light-emitting elements in this example were conducted. FIG. 32 shows results of the reliability tests. In the reliability tests, which were conducted at room temperature, the light-emitting elements were each driven under the conditions where the initial luminance was set to 5000 cd/m$^2$ and the current density was constant. FIG. 32 shows that after 3400 hours elapsed, the light-emitting element 4 kept 86% of the initial luminance, and the comparative light-emitting element 5 kept 80% of the initial luminance. The results of the reliability tests show that the light-emitting element 4 has a longer lifetime than the comparative light-emitting element 5.

As described in Example 3, 2mFDBtPDBq used in the light-emitting element 4 has higher solubility in an organic solvent than 2mDBTBPDBq-II used in the comparative light-emitting element 5. A compound with high solubility can be easily purified and impurities thereof can be easily eliminated. The use of the compound of one embodiment of the present invention from which impurities are sufficiently removed probably allowed the light-emitting element to have suppressed initial deterioration and high reliability.

EXAMPLE 7

In this example, the light-emitting element of one embodiment of the present invention will be described. A chemical formula of a material used in this example is shown below. Note that the chemical formulae of the materials which are shown above are omitted.

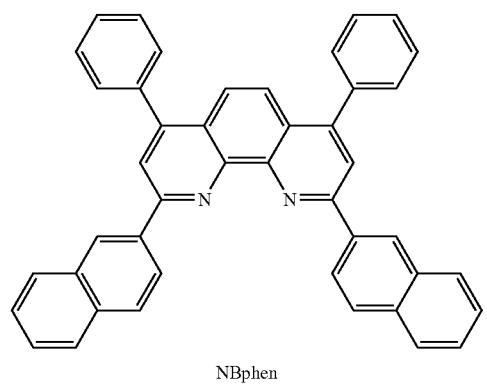 [SMILES: c1ccc(-c2cc(-c3ccc4ccccc4c3)nc3c2ccc2c(-c4ccccc4)cc(-c4ccc5ccccc5c4)nc23)cc1]

NBphen

A method for manufacturing a light-emitting element 6 in this example will be described below. For the structure of the light-emitting element in this example, FIG. 15 can be referred to.

(Light-emitting Element 6)

Components of the light-emitting element 6 other than the light-emitting layer 1113 and the electron-transport layer 1114 were formed in the same manners as those of the light-emitting element 1. Here, only the steps different from those in the method for fabricating the light-emitting element 1 are described.

The light-emitting layer 1113 of the light-emitting element 6 was formed by co-evaporation of 2mDBtBPDBq-VIII, PCBBiF, and [Ir(tBuppm)$_2$(acac)]. Here, a 20-nm-thick layer which was formed with the weight ratio of 2mDBtBPDBq-VIII to PCBBiF to [Ir(tBuppm)$_2$(acac)] adjusted to 0.7:0.3:0.05 (=2mDBtBPDBq-VIII: PCBBiF: [Ir(tBuppm)$_2$(acac)]) and a 20-nm-thick layer which was formed with the weight ratio adjusted to 0.8:0.2: 0.05 (=2mDBtBPDBq-VIII: PCBBiF: [Ir(tBuppm)$_2$(acac)]) were stacked.

The electron-transport layer 1114 of the light-emitting element 6 was formed by depositing 2mDBtBPDBq-VIII to a thickness of 20 nm and further depositing 2,9-di(2-naphthyl)-4,7-diphenyl-1,10-phenanthroline (abbreviation: NBphen) to a thickness of 10 nm.

Table 6 shows the element structure of the light-emitting element fabricated as described above in this example. Table 6 also shows an element structure of a light-emitting element 6b described in Example 8.

Figure 33:
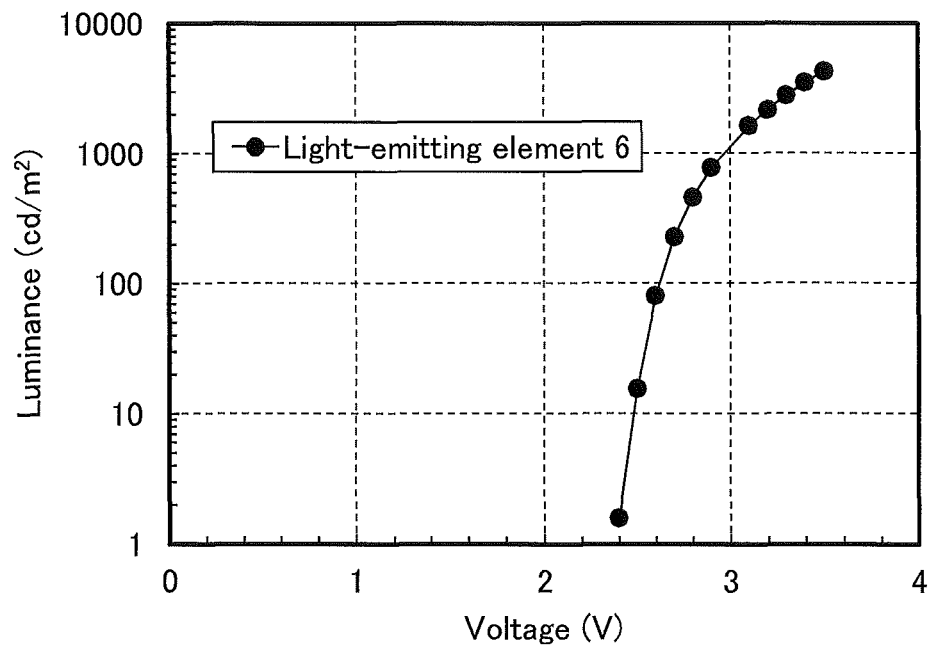
FIG. 33 is a graph showing voltage-luminance characteristics of a light-emitting element in Example 7.
Figure 34:
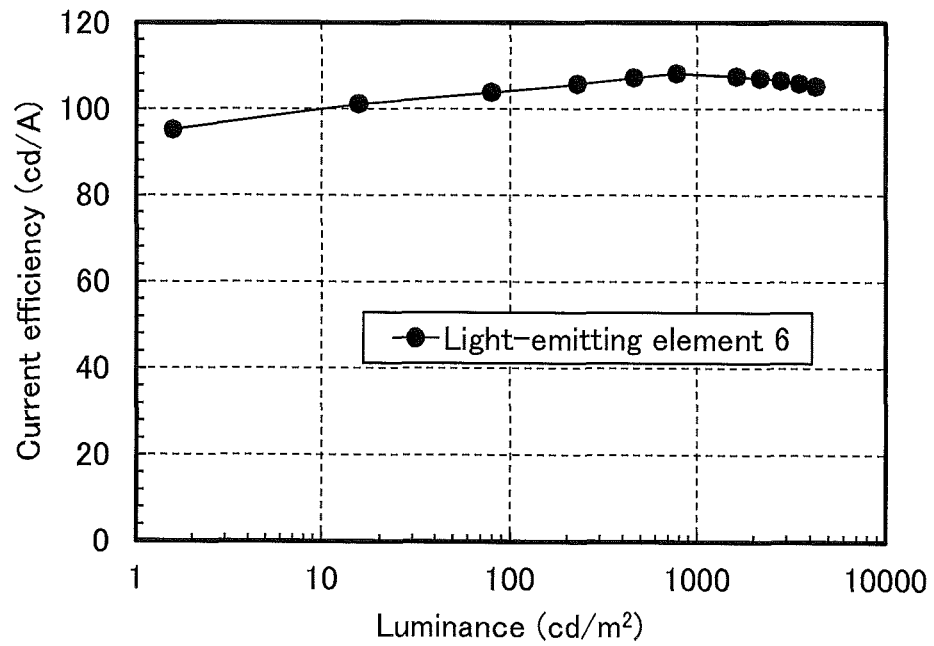
FIG. 34 is a graph showing luminance-current efficiency characteristics of a light-emitting element in Example 7.
Figure 35:
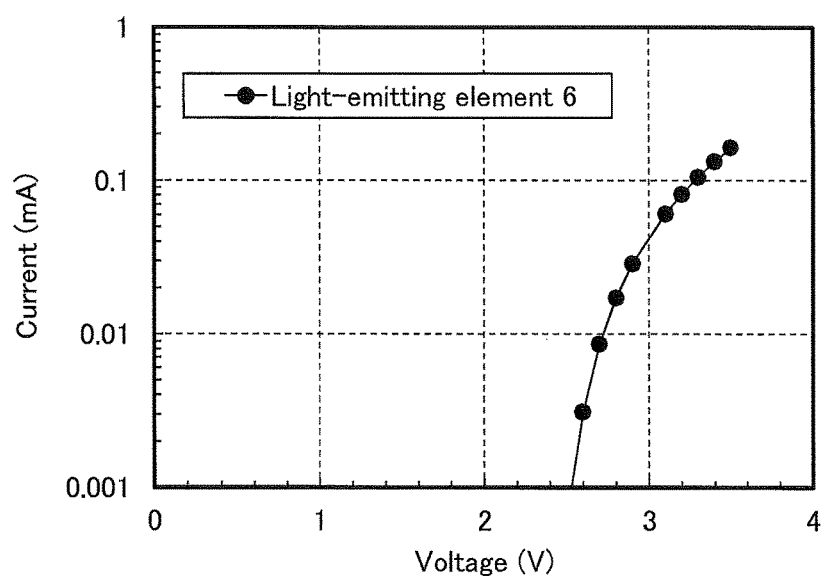
FIG. 35 is a graph showing voltage-current characteristics of a light-emitting element in Example 7.

FIG. 33 shows the voltage-luminance characteristics of the light-emitting element of this example. FIG. 34 shows luminance-current efficiency characteristics. FIG. 35 shows voltage-current characteristics. Table 7 shows the voltage (V), current density (mA/cm$^2$), CIE chromaticity coordinates (x, y), current efficiency (cd/A), power efficiency (lm/W), and external quantum efficiency (%) of the light-emitting element of this example at a luminance of 800 cd/m$^2$.

TABLE 7

|  | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 6 | 2.9 | 0.72 | 0.42 | 0.57 | 800 | 108 | 117 | 29 |

Figure 36:
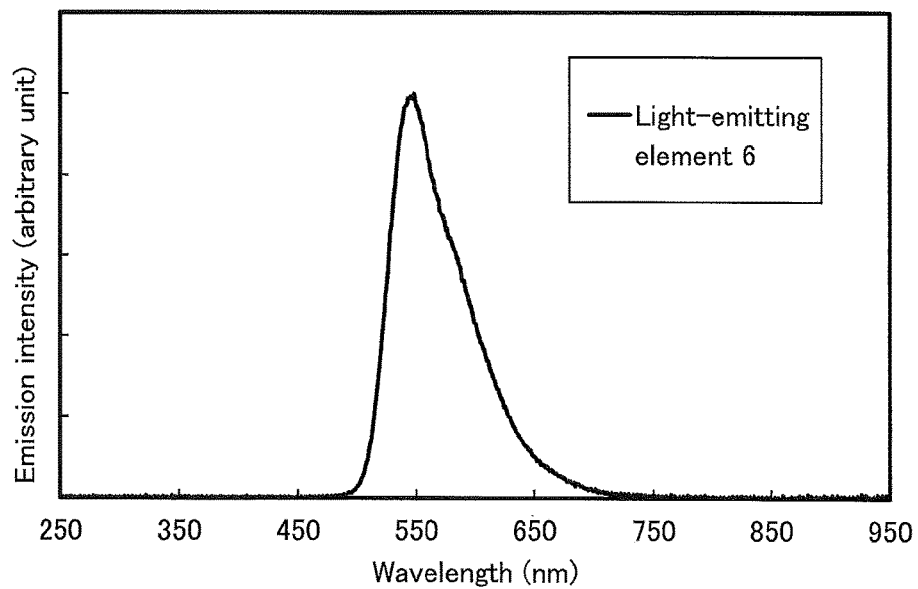
FIG. 36 is a graph showing an emission spectrum of a light-emitting element in Example 7.

The CIE chromaticity coordinates (x, y) at a luminance of 800 cd/m$^2$ of the light-emitting element 6 were (0.42, 0.57) and the light-emitting element emitted yellowish green light. FIG. 36 shows an emission spectrum when a current at a current density of 2.5 mA/cm$^2$ was supplied to the light-emitting element 6. As shown in FIG. 36, the emission spectrum of the light-emitting element 6 has a peak at approximately 548 nm. These results show that yellowish green light emission originating from [Ir(tBuppm)$_2$(acac)] was provided from the light-emitting element 6.

The measurement results of the operation characteristics show that the light-emitting element 6 has high emission efficiency and a low drive voltage.

In this example, it was found that a light-emitting element can have high emission efficiency and a low drive voltage by including the compound of one embodiment the present invention.

EXAMPLE 8

This example will show results of a heat-resistance test of a fabricated light-emitting element of one embodiment of the present invention.

TABLE 6

|  | First electrode | Hole-injection layer | Hole-transport layer | Light-emitting layer | | Electron-transport layer | | Electron-injection layer | Second electrode |
| --- | --- | --- | --- | --- | --- | --- | --- | --- | --- |
| Light-emitting element 6 (6b) | ITSO 110 nm | DBT3P-II:MoO$_x$ (= 4:2) 20 nm | BPAFLP 20 nm | 2mDBtBPDBq-VIII:PCBBiF:[Ir(tBuppm)$_2$(acac)] (=0.7:0.3:0.05) 20 nm | (=0.8:0.2:0.05) 20 nm | 2mDBtBPDBq-VIII 20 nm | NBphen 10 nm | LiF 1 nm | Al 200 nm |

The light-emitting element of this example was sealed with a glass substrate in a glove box under a nitrogen atmosphere so as not to be exposed to the air (specifically, a sealant was applied to surround the element, and at the time of sealing, UV treatment was performed and then heat treatment was performed at 80° C. for 1 hour). Then, the operation characteristics of the light-emitting element were measured. Note that the measurement was carried out at room temperature (in an atmosphere kept at 25° C.).

In this example, the light-emitting element 6b and a comparative light-emitting element 7b were manufactured.

The structure and manufacturing method of the light-emitting element 6b are the same as those of the light-emitting element 6 in Example 7.

(Comparative Light-emitting Element 7b)

Components of the comparative light-emitting element 7b other than the light-emitting layer 1113 and the electron-transport layer 1114 were formed in the same manners as those of the light-emitting element 1. Here, only the steps different from those in the method for fabricating the light-emitting element 1 are described.

The light-emitting layer 1113 of the comparative light-emitting element 7b was formed by co-evaporation of 2mDBTBPDBq-II, PCBBiF, and [Ir(tBuppm)$_2$(acac)]. Here, a 20-nm-thick layer which was formed with the weight ratio of 2mDBTBPDBq-II to PCBBiF to [Ir(tBuppm)$_2$(acac)] adjusted to 0.7:0.3:0.05 (=2mDBTBPDBq-II: PCBBiF: [Ir(tBuppm)$_2$(acac)]) and a 20-nm-thick layer which was formed with the weight ratio adjusted to 0.8:0.2:0.05 (=2mDBTBPDBq-II: PCBBiF: [Ir(tBuppm)$_2$(acac)]) were stacked.

The electron-transport layer 1114 of the comparative light-emitting element 7b was formed by depositing 2mDBTBPDBq-II to a thickness of 20 nm and further depositing NBphen to a thickness of 10 nm.

Table 8 shows an element structure of the comparative light-emitting element 7b.

TABLE 8

| | First electrode | Hole-injection layer | Hole-transport layer | Light-emitting layer | | Electron-transport layer | Electron-injection layer | Second electrode |
|---|---|---|---|---|---|---|---|---|
| Comparative light-emitting element 7b | ITSO 110 nm | DBT3P-II:MoO$_x$ (=4:2) 20 nm | BPAFLP 20 nm | 2mDBTBPDBq-II:PCBBiF:[Ir(tBuppm)$_2$(acac)] (=0.7:0.3:0.05) 20 nm | (=0.8:0.2:0.05) 20 nm | 2mDBTBPDBq-II 20 nm   NBphen 10 nm | LiF 1 nm | Al 200 nm |

In this example, the light-emitting elements were each preserved in a thermostatic oven maintained at 100° C. for a predetermined time, and the operation characteristics were measured. Note that the operation characteristics were measured at room temperature (in an atmosphere kept at 25° C.) after the light-emitting elements were taken out of the thermostatic oven.

Figure 37:
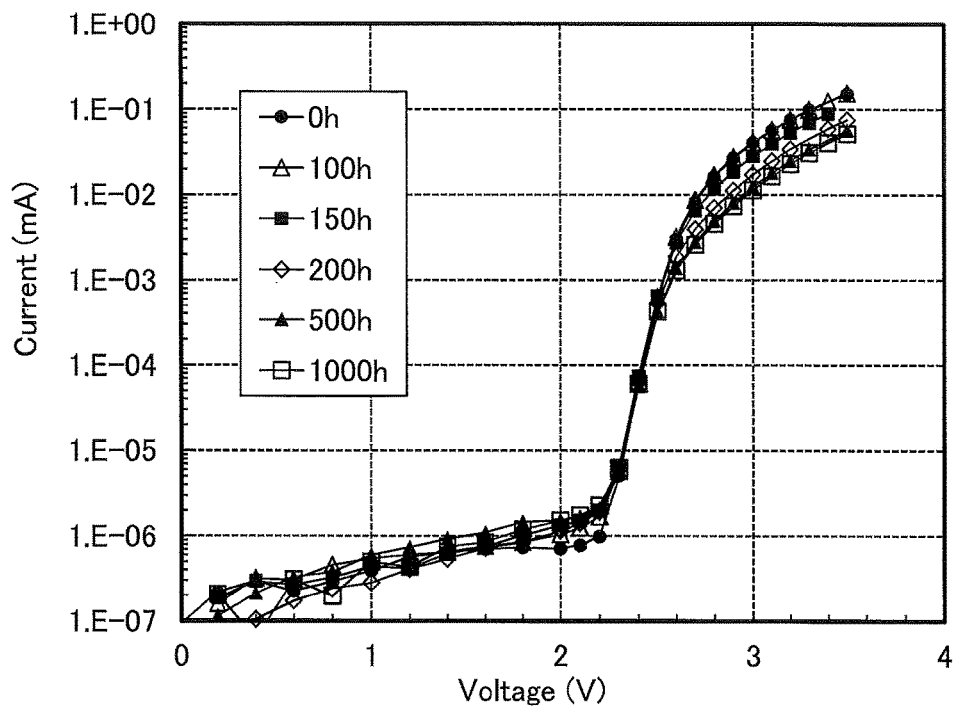
FIG. 37 is a graph showing voltage-current characteristics of a light-emitting element 6b.
Figure 38:
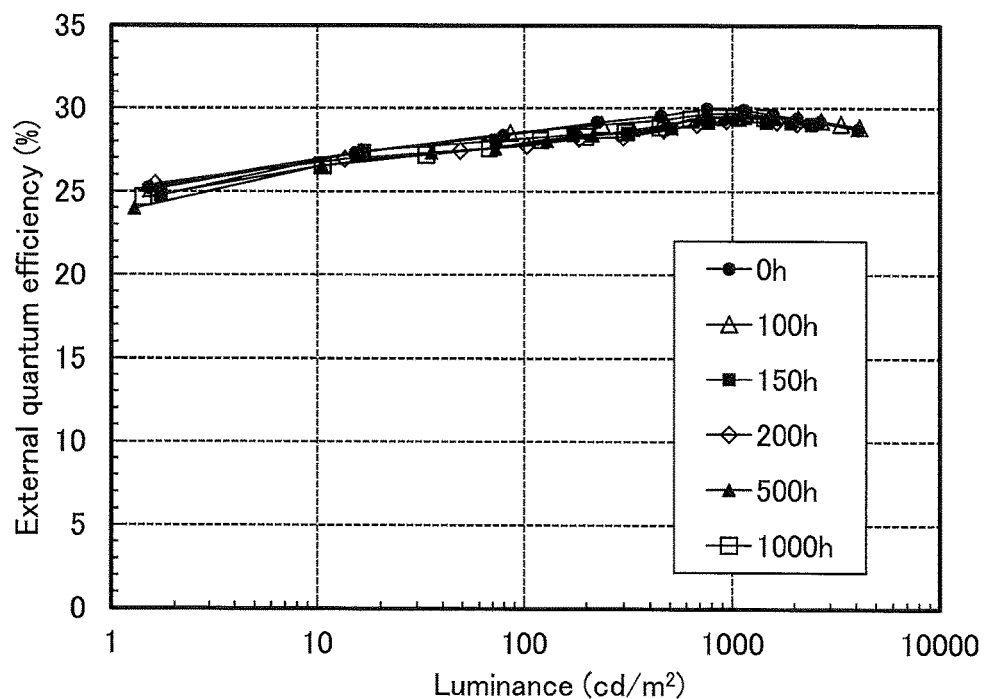
FIG. 38 is a graph showing luminance-external quantum efficiency characteristics of a light-emitting element 6b.

FIGS. 37 and 38 respectively show the voltage-current characteristics and luminance-external quantum efficiency characteristics of the light-emitting element 6b after preservation at 100° C. for 1000 hours. Note that in each of FIGS. 37 and 38, the characteristics of the light-emitting element 6b measured before the preservation test, after 100-hour preservation, after 150-hour preservation, after 200-hour preservation, and after 500-hour preservation are also shown.

Figure 39:
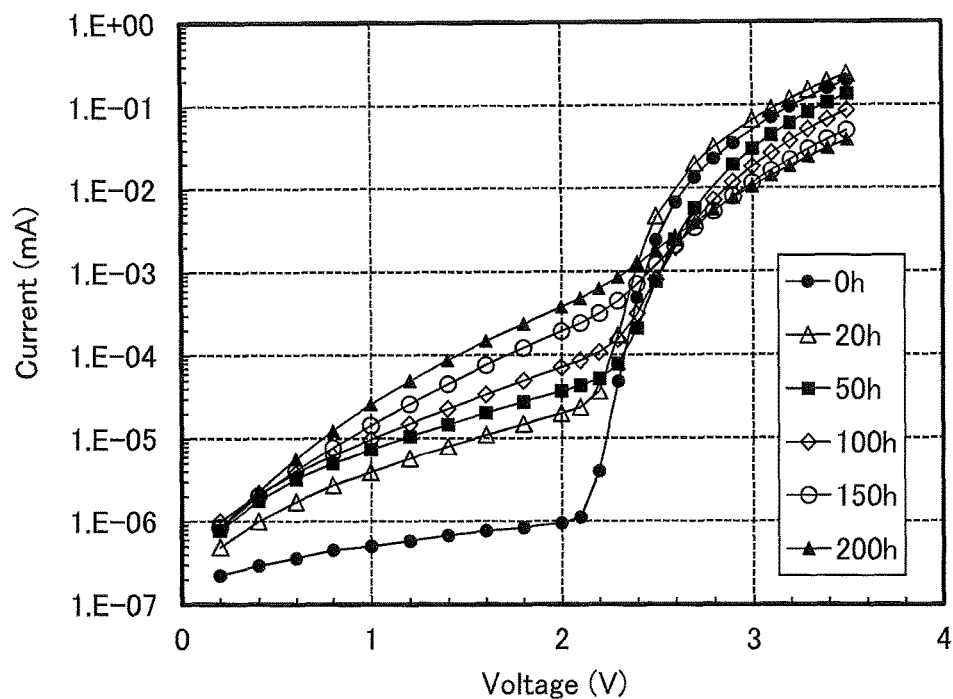
FIG. 39 is a graph showing voltage-current characteristics of a comparative light-emitting element 7b.
Figure 40:
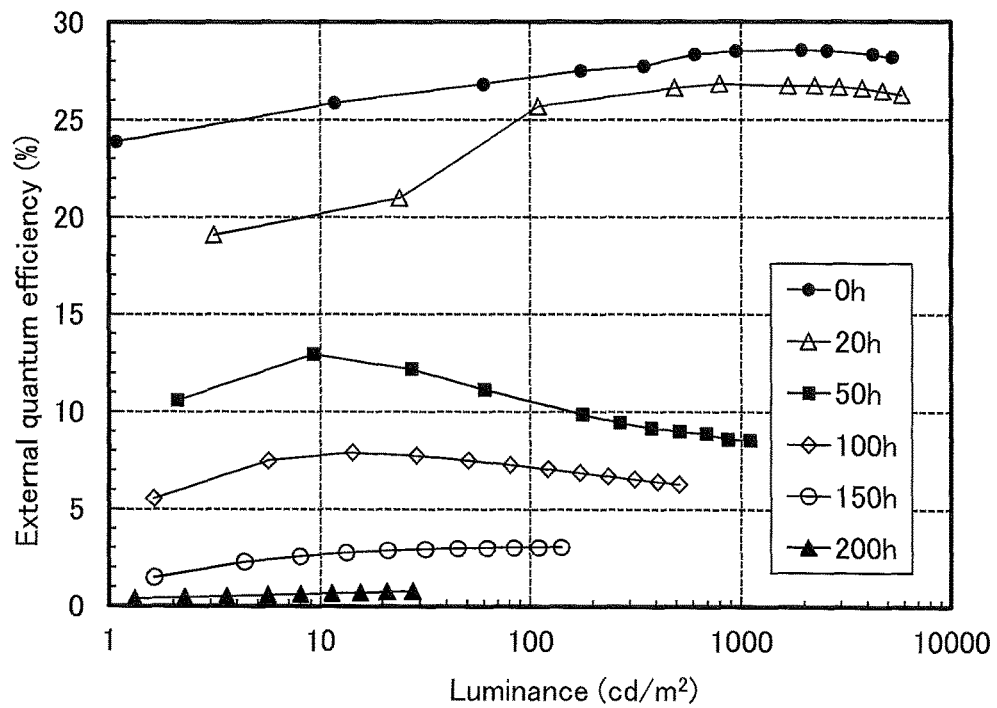
FIG. 40 is a graph showing luminance-external quantum efficiency characteristics of a comparative light-emitting element 7b.

FIGS. 39 and 40 respectively show the voltage-current characteristics and luminance-external quantum efficiency characteristics of the comparative light-emitting element 7b after preservation at 100° C. for 200 hours. Note that in each of FIGS. 39 and 40, the characteristics of the comparative light-emitting element 7b measured before the preservation test, after 20-hour preservation, after 50-hour preservation, after 100-hour preservation, and after 150-hour preservation are also shown.

From FIGS. 37 and 38, although preserved at 100° C. for 1000 hours, the light-emitting element 6b had only a small change in voltage-current characteristics and luminance-external quantum efficiency characteristics and suffered little deterioration in element characteristics. In contrast, as can be seen from FIGS. 39 and 40, the comparative light-emitting element 7b was considerably changed in voltage-current characteristics and luminance-external quantum efficiency characteristics and suffered deterioration in element characteristics as a result of the preservation at 100° C. It is also shown that the comparative light-emitting element 7b after the preservation at 100° C. for 200 hours hardly emitted light.

Figure 41:
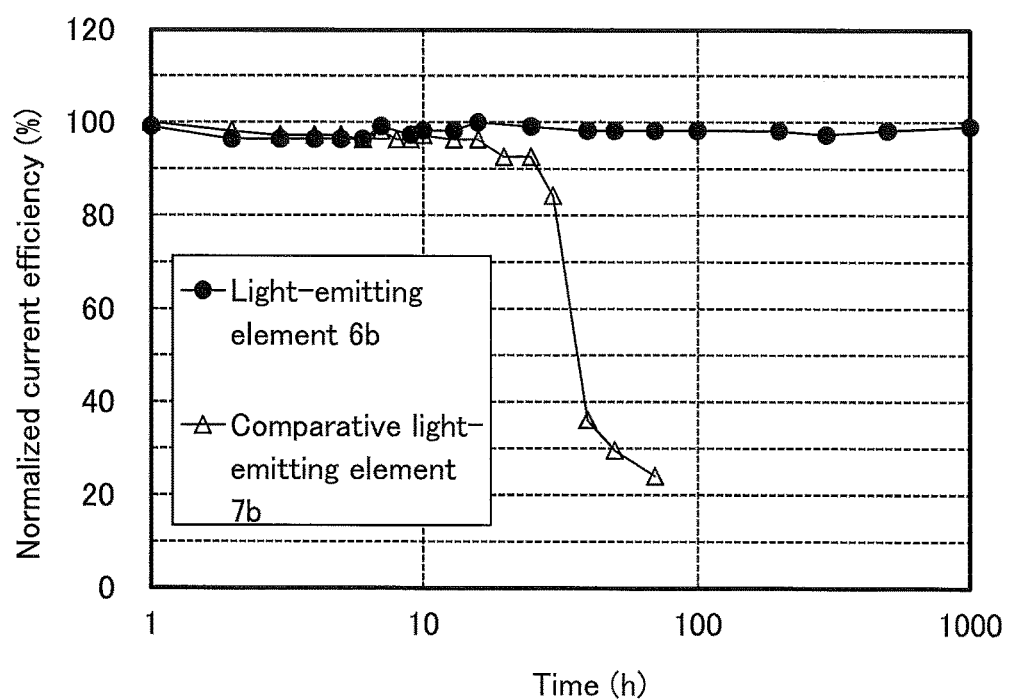
FIG. 41 shows results of preservation tests of light-emitting elements in Example 8.

FIG. 41 shows preservation test results in this example. As can be seen from the measurement results, the current efficiency of the light-emitting element 6b was hardly changed even after preservation at 100° C. for 1000 hours. In contrast, the current efficiency of the comparative light-emitting element 7b was greatly reduced, which suggests current leakage.

The above results show that in high-temperature preservation tests, behavior of the light-emitting element 6b that includes 2mDBtBPDBq-VIII with a 9,9-dialkylfluorenyl group is significantly different from behavior of the comparative light-emitting element 7b that includes 2mDBTB-PDBq-II without a 9,9-dialkylfluorenyl group. In other words, the characteristics of the comparative light-emitting element 7b considerably deteriorate while the characteristics of the light-emitting element 6b hardly deteriorate.

It was thus found that when including the compound of one embodiment of the present invention in which a dibenzothiophene skeleton has a 9,9-dialkylfluorenyl group as a substituent, a light-emitting element has higher heat resistance and a longer lifetime than when including a compound without a 9,9-dialkylfluorenyl group as a substituent.

EXAMPLE 9

In this example, the light-emitting element of one embodiment of the present invention will be described. Because the materials used in this example are already shown, the chemical formulae thereof are omitted here.

A method for manufacturing a light-emitting element 8 in this example will be described below. For the structure of the light-emitting element in this example, FIG. 15 can be referred to.

(Light-emitting Element 8)

Components of the light-emitting element 8 other than the light-emitting layer 1113 were formed in the same manners as those of the light-emitting element 6. Here, only the steps different from those in the method for fabricating the light-emitting element 6 are described.

The light-emitting layer 1113 of the light-emitting element 8 was formed by co-evaporation of 2mDBtBPDBq-VIII, PCBBiF, and [Ir(dppm)$_2$(acac)]. Here, a 20-nm-thick layer which was formed with the weight ratio of 2mDBtB-PDBq-VIII to PCBBiF to [Ir(dppm)$_2$(acac)] adjusted to 0.7:0.3:0.05 (=2mDBtBPDBq-VIII: PCBBiF: [Ir(dppm)$_2$(acac)]) and a 20-nm-thick layer which was formed with the weight ratio adjusted to 0.8:0.2:0.05 (=2mDBtBPDBq-VIII: PCBBiF: [Ir(dppm)$_2$(acac)]) were stacked.

Table 9 shows the element structure of the light-emitting element fabricated as described above in this example.

TABLE 9

| | First electrode | Hole-injection layer | Hole-transport layer | Light-emitting layer | | Electron-transport layer | Electron-injection layer | Second electrode |
|---|---|---|---|---|---|---|---|---|
| Light-emitting element 8 | ITSO 110 nm | DBT3P-II:MoO$_x$ (=4:2) 20 nm | BPAFLP 20 nm | 2mDBtBPDBq-VIII:PCBBiF:[Ir(dppm)$_2$(acac)] (=0.7:0.3:0.05) 20 nm | (=0.8:0.2:0.05) 20 nm | 2mDBtBPDBq-VIII 20 nm | NBphen 10 nm | LiF 1 nm | Al 200 nm |

The light-emitting element of this example was sealed with a glass substrate in a glove box under a nitrogen atmosphere so as not to be exposed to the air (specifically, a sealant was applied to surround the element, and at the time of sealing, UV treatment was performed and then heat treatment was performed at 80° C. for 1 hour). Then, the operation characteristics of the light-emitting element were measured. Note that the measurement was carried out at room temperature (in an atmosphere kept at 25° C.).

Figure 42:
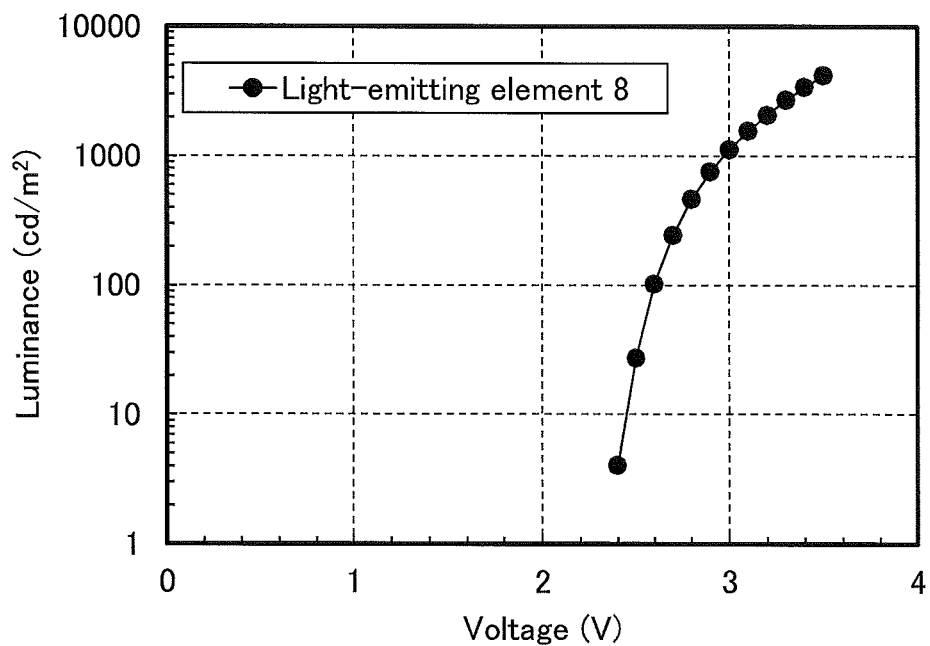
FIG. 42 is a graph showing voltage-luminance characteristics of a light-emitting element in Example 9.
Figure 43:
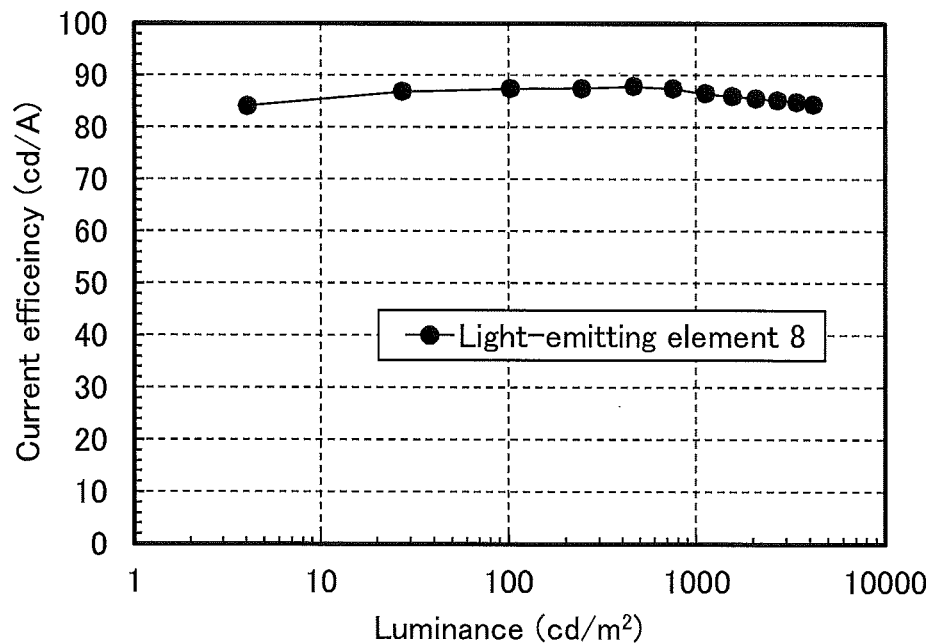
FIG. 43 is a graph showing luminance-current efficiency characteristics of a light-emitting element in Example 9.
Figure 44:
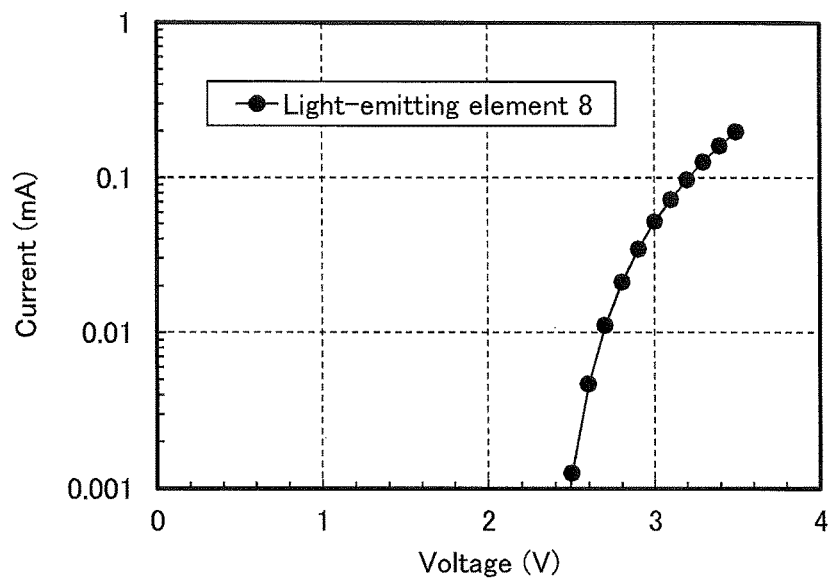
FIG. 44 is a graph showing voltage-current characteristics of a light-emitting element in Example 9.

FIG. 42 shows the voltage-luminance characteristics of the light-emitting element of this example. FIG. 43 shows luminance-current efficiency characteristics. FIG. 44 shows voltage-current characteristics. Table 10 shows the voltage (V), current density (mA/cm$^2$), CIE chromaticity coordinates (x, y), current efficiency (cd/A), power efficiency (lm/W), and external quantum efficiency (%) of the light-emitting element of this example at a luminance of 1100 cd/m$^2$.

TABLE 10

| | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
|---|---|---|---|---|---|---|---|---|
| Light-emitting element 8 | 3.0 | 1.30 | 0.55 | 0.45 | 1100 | 87 | 91 | 32 |

Figure 45:
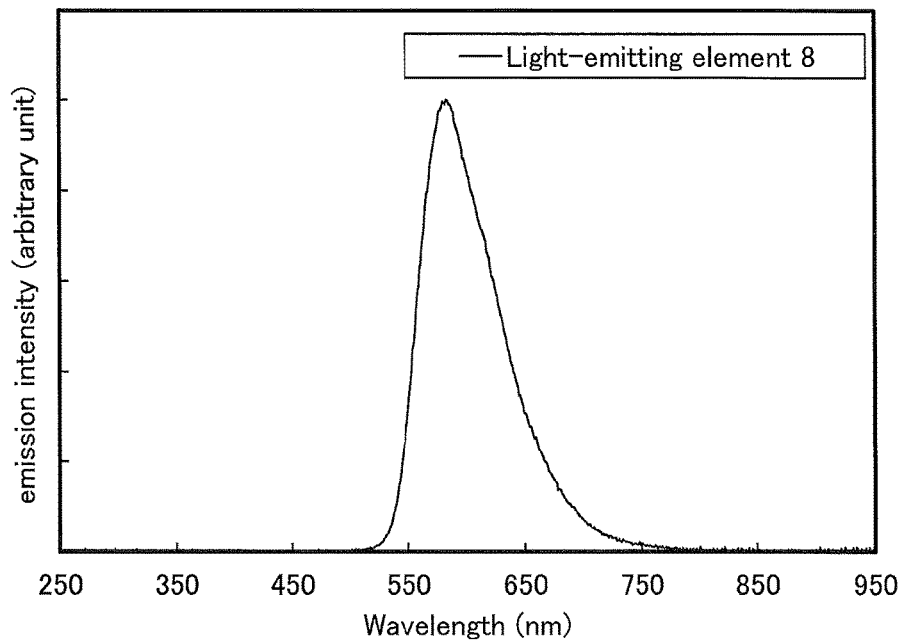
FIG. 45 is a graph showing an emission spectrum of a light-emitting element in Example 9.

The CIE chromaticity coordinates (x, y) at a luminance of 1100 cd/m$^2$ of the light-emitting element 8 were (0.55, 0.45) and the light-emitting element emitted orange light. FIG. 45 shows an emission spectrum when a current at a current density of 2.5 mA/cm$^2$ was supplied to the light-emitting element 8. As shown in FIG. 45, the emission spectrum of the light-emitting element 8 has a peak at approximately 583 nm. These results show that orange light emission originating from [Ir(dppm)$_2$(acac)] was provided from the light-emitting element 8.

The measurement results of the operation characteristics show that the light-emitting element 8 has high emission efficiency and a low drive voltage.

In this example, it was found that a light-emitting element can have high emission efficiency and a low drive voltage by including the compound of one embodiment the present invention.

This application is based on Japanese Patent Application serial no. 2014-091164 filed with the Japan Patent Office on Apr. 25, 2014, the entire contents of which are hereby incorporated by reference.

What is claimed is:

1. A compound represented by Formula (G0):

E-Ar-A-X  (G0), wherein:

A represents any one of a substituted or unsubstituted dibenzothiophenylene group and a substituted or unsubstituted dibenzofuranylene group;

X represents an unsubstituted fluorenyl group or a fluorenyl group substituted by one or more of an alkyl group having 1 to 6 carbon atoms, a phenyl group, and a naphthyl group;

E represents a substituted or unsubstituted dibenzo[f,h]quinoxalinyl group; and

Ar represents a substituted or unsubstituted arylene group having 6 to 30 carbon atoms.

2. The compound according to claim 1, wherein the compound is represented by Formula (G1):

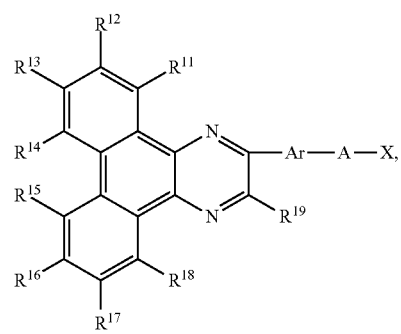

(G1)

and wherein each of $R^{11}$ to $R^{19}$ independently represents any one of hydrogen, an alkyl group having 1 to 6 carbon atoms, and a substituted or unsubstituted aryl group having 6 to 13 carbon atoms.

3. A compound represented by Formula (G2):

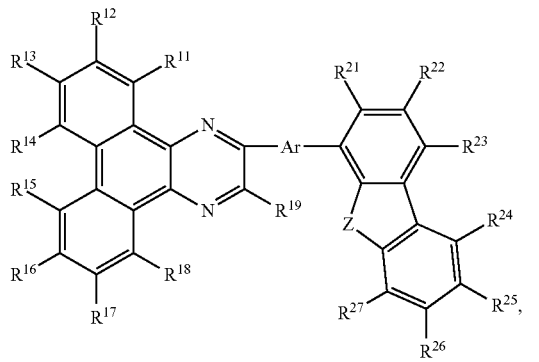

(G2)

wherein:
Z represents any one of oxygen and sulfur;
each of $R^{11}$ to $R^{19}$ independently represents any one of hydrogen, an alkyl group having 1 to 4 carbon atoms, and a substituted or unsubstituted aryl group having 6 to 13 carbon atoms;
at least one of $R^{21}$ to $R^{27}$ represents an unsubstituted fluorenyl group or a fluorenyl group substituted by one or more of an alkyl group having 1 to 6 carbon atoms, a phenyl group, and a naphthyl group;
each of the others of $R^{21}$ to $R^{27}$ independently represents any one of hydrogen, an alkyl group having 1 to 6 carbon atoms, and a substituted or unsubstituted aryl group having 6 to 13 carbon atoms; and
Ar represents a substituted or unsubstituted arylene group having 6 to 30 carbon atoms.

4. The compound according to claim 3, wherein the compound is represented by Formula (G3):

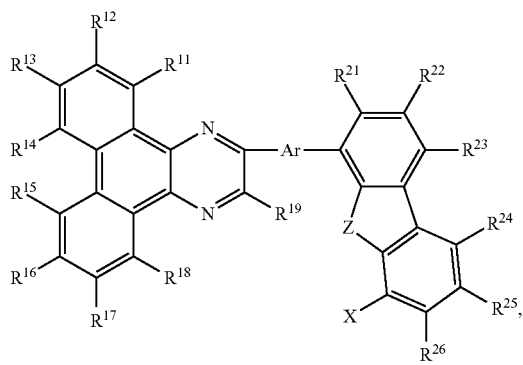

(G3)

wherein X represents the unsubstituted fluorenyl group or the substituted fluorenyl group, and
wherein each of $R^{21}$ to $R^{26}$ independently represents any one of hydrogen, an alkyl group having 1 to 6 carbon atoms, and a substituted or unsubstituted aryl group having 6 to 13 carbon atoms.

5. The compound according to claim 4, wherein X represents a substituted or unsubstituted 9,9-dialkylfluorenyl group.

6. The compound according to claim 3, wherein Ar represents one of a substituted or unsubstituted phenylene group and a substituted or unsubstituted biphenyldiyl group.

7. A light-emitting element comprising, between a pair of electrodes, a layer containing a light-emitting organic compound,
wherein the layer contains the compound according to claim 3.

8. A light-emitting element comprising, between a pair of electrodes, a layer containing a light-emitting organic compound,
wherein the layer contains a light-emitting substance and the compound according to claim 3.

9. A light-emitting device comprising:
the light-emitting element according to claim 7; and
a transistor or a substrate.

10. An electronic device comprising:
the light-emitting device according to claim 9; and
a microphone, a speaker, or an external connection terminal.

11. A lighting device comprising:
the light-emitting device according to claim 9; and
a support, a housing, or a cover.

12. A compound represented by Formula (G4):

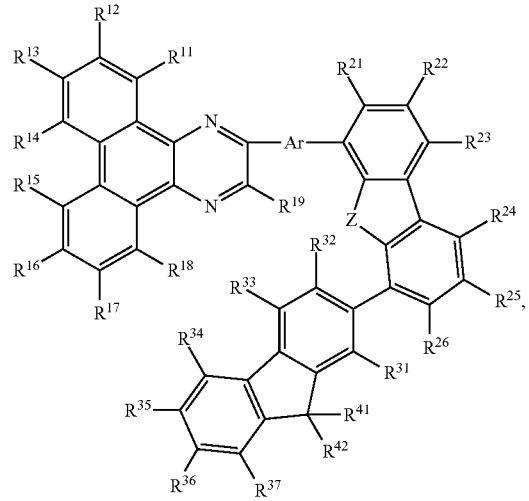

(G4)

wherein:
Z represents any one of oxygen and sulfur;
each of $R^{11}$ to $R^{19}$, $R^{21}$ to $R^{26}$, and $R^{31}$ to $R^{37}$ independently represents any one of hydrogen, an alkyl group having 1 to 6 carbon atoms, and a substituted or unsubstituted aryl group having 6 to 13 carbon atoms;
each of $R^{41}$ and $R^{42}$ independently represents any one of hydrogen and an alkyl group having 1 to 6 carbon atoms; and
Ar represents a substituted or unsubstituted arylene group having 6 to 30 carbon atoms.

13. The compound according to claim 12, wherein $R^{41}$ and $R^{42}$ each represent a methyl group.

14. The compound according to claim 12, wherein Ar represents one of a substituted or unsubstituted phenylene group and a substituted or unsubstituted biphenyldiyl group.

15. A light-emitting element comprising, between a pair of electrodes, a layer containing a light-emitting organic compound,
wherein the layer contains the compound according to claim 12.

16. A light-emitting element comprising, between a pair of electrodes, a layer containing a light-emitting organic compound,
wherein the layer contains a light-emitting substance and the compound according to claim 12.

17. A light-emitting device comprising:
the light-emitting element according to claim 15; and
a transistor or a substrate.

18. An electronic device comprising:
the light-emitting device according to claim 17; and
a microphone, a speaker, or an external connection terminal.

19. A lighting device comprising:
the light-emitting device according to claim 17; and
a support, a housing, or a cover.

20. The compound according to claim 12, wherein the compound is represented by Formula (100) or (112)
(100)
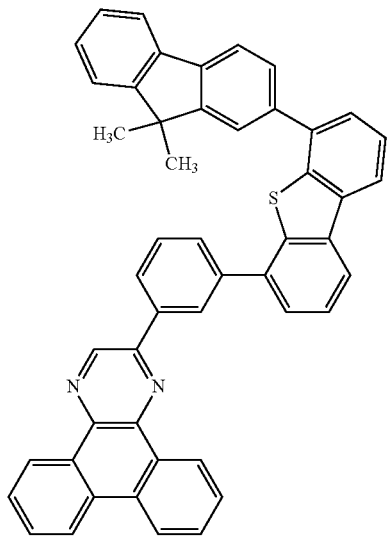
(112)
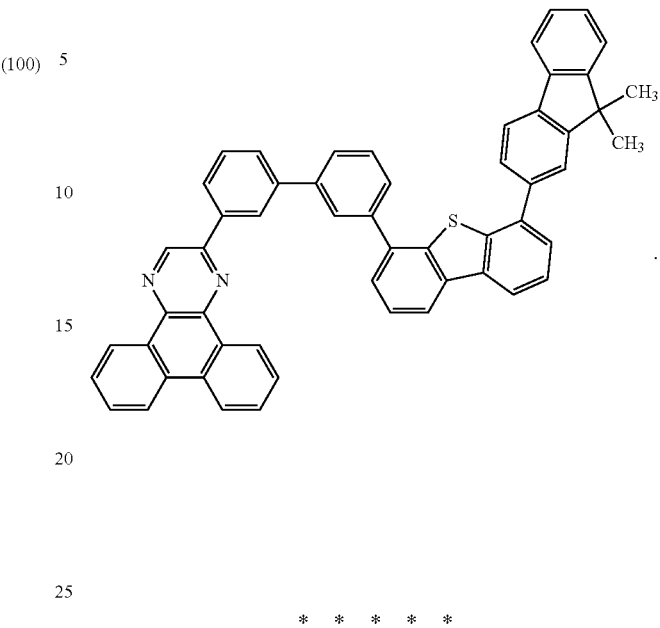
* * * * *